(12) United States Patent
Boll et al.

(10) Patent No.: US 11,819,259 B2
(45) Date of Patent: Nov. 21, 2023

(54) METHODS AND APPARATUS FOR CONTROLLED RF TREATMENTS AND RF GENERATOR SYSTEM

(71) Applicant: Cynosure, LLC, Westford, MA (US)

(72) Inventors: James Boll, Auburndale, MA (US); Richard Shaun Welches, Townsend, MA (US); Daniel Masse, Windham, NH (US); Samuel Bruce, Malden, MA (US); Jeffrey Simon, Medford, MA (US); Ali Shajii, Weston, MA (US); David Sonnenshein, Dorchester, MA (US); Robert D. McCarthy, Maynard, MA (US); Rafael Armando Sierra, Gulfport, FL (US)

(73) Assignee: Cynosure, Inc., Westford, MA (US)

( * ) Notice: Subject to any disclaimer, the term of this patent is extended or adjusted under 35 U.S.C. 154(b) by 527 days.

(21) Appl. No.: 16/269,314

(22) Filed: Feb. 6, 2019

(65) Prior Publication Data

US 2019/0239939 A1    Aug. 8, 2019

Related U.S. Application Data

(60) Provisional application No. 62/771,294, filed on Nov. 26, 2018, provisional application No. 62/627,611, filed on Feb. 7, 2018.

(51) Int. Cl.
*A61B 18/00* (2006.01)
*A61B 18/08* (2006.01)
(Continued)

(52) U.S. Cl.
CPC ........ *A61B 18/1233* (2013.01); *A61B 18/082* (2013.01); *A61B 18/14* (2013.01);
(Continued)

(58) Field of Classification Search
CPC ........... A61B 2018/00636; A61B 2018/00678; A61B 2018/00642; A61B 2018/00648;
(Continued)

(56) References Cited

U.S. PATENT DOCUMENTS 236,203 A    1/1881   Campbell
1,916,722 A  6/1931   Ende
(Continued)

FOREIGN PATENT DOCUMENTS

CN    1697631     11/2005
CN    101610736   12/2009
(Continued)

OTHER PUBLICATIONS

Examination Report in Australian Application No. 2019217623, dated Mar. 10, 2021, 4 pages.
(Continued)

*Primary Examiner* — Michael F Peffley
*Assistant Examiner* — Nicholas S Borsch
(74) *Attorney, Agent, or Firm* — Ganz Pollard, LLC

(57) ABSTRACT

Electrosurgical systems and components thereof configured to deliver RF energy to a target site of a human or other animal patient with selectable RF energy delivery profiles, temperature sensors and controls, and/or electrodes configured to more uniformly or effectively delivery energy to target tissue.

26 Claims, 28 Drawing Sheets

(51) Int. Cl.
*A61B 18/12* (2006.01)
*A61B 18/14* (2006.01)

(52) U.S. Cl.
CPC .............. *A61B 2018/00083* (2013.01); *A61B 2018/00095* (2013.01); *A61B 2018/00101* (2013.01); *A61B 2018/00452* (2013.01); *A61B 2018/00666* (2013.01); *A61B 2018/00678* (2013.01); *A61B 2018/00702* (2013.01); *A61B 2018/00726* (2013.01); *A61B 2018/00732* (2013.01); *A61B 2018/00761* (2013.01); *A61B 2018/00791* (2013.01); *A61B 2018/00815* (2013.01); *A61B 2018/00821* (2013.01); *A61B 2018/128* (2013.01); *A61B 2018/147* (2013.01)

(58) Field of Classification Search
CPC ........... A61B 2018/00702; A61B 2018/00708; A61B 2018/00732; A61B 2018/00797; A61B 2018/00791; A61B 2018/00815; A61B 2018/00821; A61B 18/1233; A61B 18/082; A61B 18/14; A61B 2018/00083; A61B 2018/00095; A61B 2018/00101; A61B 2018/00452; A61B 2018/00666; A61B 2018/00726; A61B 2018/00761; A61B 2018/128; A61B 2018/147; A61B 2018/00922; A61B 2018/00958
See application file for complete search history.

(56) References Cited

U.S. PATENT DOCUMENTS

| | | |
|---|---|---|
| 1,943,543 A | 6/1931 | Mcfadden |
| 1,881,250 A | 10/1932 | Tomlinson |
| 1,942,543 A | 1/1934 | Forman |
| 1,945,327 A | 1/1934 | Morse |
| 1,983,669 A | 12/1934 | Kimble |
| 2,102,270 A | 12/1937 | Hyams |
| 2,888,928 A | 4/1957 | Wright |
| 3,058,470 A | 10/1962 | Seeliger et al. |
| 3,532,095 A | 10/1970 | Miller et al. |
| 3,730,188 A | 5/1973 | Ellman |
| 3,799,168 A | 3/1974 | Peters |
| 3,825,004 A | 7/1974 | Durden |
| 3,825,044 A | 7/1974 | Lidikay et al. |
| 3,858,586 A | 1/1975 | Lessen |
| 3,879,947 A | 4/1975 | Gaiser |
| 3,916,909 A | 11/1975 | Kletschka et al. |
| 3,920,022 A | 11/1975 | Pastor |
| D246,053 S | 10/1977 | Staub et al. |
| 4,051,855 A | 10/1977 | Schneiderman |
| 4,071,028 A | 1/1978 | Perkins |
| 4,103,688 A | 8/1978 | Edwards |
| 4,108,182 A | 8/1978 | Hartman et al. |
| 4,123,673 A | 10/1978 | Gonser |
| 4,137,919 A | 2/1979 | Farin et al. |
| 4,148,321 A | 4/1979 | Wyss et al. |
| 4,148,324 A | 4/1979 | Muller et al. |
| 4,171,700 A | 10/1979 | Farin |
| 4,188,927 A | 2/1980 | Harris |
| 4,221,222 A | 9/1980 | Detsch |
| 4,185,927 A | 10/1980 | Uttech |
| 4,246,902 A | 1/1981 | Martinez |
| 4,271,891 A | 1/1981 | Pommier |
| 4,269,174 A | 5/1981 | Adair |
| 4,271,837 A | 6/1981 | Schuler |
| 4,289,132 A | 9/1981 | Rieman |
| 4,312,364 A | 1/1982 | Convert et al. |
| 4,314,560 A | 2/1982 | Helfgott et al. |
| D263,872 S | 4/1982 | Rakocy et al. |
| 4,334,539 A | 4/1982 | Childs et al. |
| 4,346,416 A | 8/1982 | Riggle et al. |
| 4,378,801 A | 4/1983 | Oosten |
| 4,438,766 A | 3/1984 | Bowers |
| 4,463,759 A | 8/1984 | Garito et al. |
| 4,473,075 A | 9/1984 | Rexroth |
| 4,476,862 A | 10/1984 | Pao |
| 4,492,231 A | 1/1985 | Auth |
| 4,517,975 A | 5/1985 | Garito et al. |
| 4,541,440 A | 9/1985 | Parsonnet |
| 4,548,207 A | 10/1985 | Reimels |
| 4,550,727 A | 11/1985 | Rexroth |
| D281,721 S | 12/1985 | Scanlan et al. |
| 4,557,272 A | 12/1985 | Carr |
| 4,565,200 A | 1/1986 | Cosman |
| 4,658,815 A | 4/1987 | Farin et al. |
| 4,658,819 A | 4/1987 | Harris et al. |
| 4,658,820 A | 4/1987 | Klicek |
| 4,688,569 A | 8/1987 | Rabinowitz |
| 4,701,193 A | 10/1987 | Robertson et al. |
| 4,706,667 A | 11/1987 | Roos |
| 4,711,239 A | 12/1987 | Sorochenko et al. |
| 4,712,544 A | 12/1987 | Ensslin |
| 4,716,897 A | 1/1988 | Noguchi et al. |
| 4,754,754 A | 7/1988 | Garito et al. |
| 4,821,717 A | 4/1989 | Wehrli |
| 4,827,927 A | 5/1989 | Newton |
| 4,834,095 A | 5/1989 | Miller |
| 4,886,060 A | 12/1989 | Wiksell |
| 4,892,105 A | 1/1990 | Prass |
| 4,931,047 A | 6/1990 | Broadwin et al. |
| 4,936,281 A | 6/1990 | Stasz |
| 4,962,766 A | 10/1990 | Herzon |
| 4,986,839 A | 1/1991 | Wertz et al. |
| 5,035,695 A | 7/1991 | Weber, Jr. et al. |
| D320,271 S | 9/1991 | Jones |
| 5,047,026 A | 9/1991 | Rydell |
| 5,047,029 A | 9/1991 | Aebi et al. |
| D320,856 S | 10/1991 | Scheller |
| D321,056 S | 10/1991 | Chambers |
| 5,067,953 A | 11/1991 | Feucht |
| D322,483 S | 12/1991 | Kishimoto |
| D322,676 S | 12/1991 | Chambers |
| 5,078,716 A | 1/1992 | Doll |
| 5,098,430 A | 3/1992 | Fleenor |
| 5,125,058 A | 6/1992 | Tenerz et al. |
| 5,127,460 A | 7/1992 | Abadi et al. |
| D329,718 S | 9/1992 | Sulik |
| 5,160,334 A | 11/1992 | Billings et al. |
| 5,186,714 A | 2/1993 | Boudreault et al. |
| 5,195,959 A | 3/1993 | Smith |
| 5,196,007 A | 3/1993 | Ellman et al. |
| 5,217,458 A | 6/1993 | Parins |
| 5,224,947 A | 7/1993 | Cooper et al. |
| 5,226,939 A | 7/1993 | Nicolas et al. |
| 5,243,812 A | 9/1993 | Strobel et al. |
| 5,246,440 A | 9/1993 | Van Noord |
| 5,261,905 A | 11/1993 | Doresey, III |
| 5,267,994 A | 12/1993 | Gentelia et al. |
| 5,267,998 A | 12/1993 | Hagen |
| 5,275,151 A | 1/1994 | Shockey et al. |
| 5,281,218 A | 1/1994 | Imran |
| 5,290,283 A | 3/1994 | Suda |
| 5,304,183 A | 4/1994 | Gourlay et al. |
| D346,866 S | 5/1994 | Lotuaco |
| 5,318,563 A | 6/1994 | Malis |
| 5,324,288 A | 6/1994 | Billings et al. |
| 5,325,288 A | 6/1994 | Satou |
| 5,336,218 A | 8/1994 | Linhares |
| 5,342,349 A | 8/1994 | Kaufman |
| 5,342,356 A | 8/1994 | Ellman et al. |
| D351,227 S | 10/1994 | Patton et al. |
| D352,350 S | 11/1994 | Rambo et al. |
| 5,360,428 A | 11/1994 | Hutchinson, Jr. |
| 5,364,393 A | 11/1994 | Auth et al. |
| 5,368,560 A | 11/1994 | Rambo et al. |
| 5,371,188 A | 12/1994 | Heinemann et al. |
| 5,374,188 A | 12/1994 | Frank et al. |
| 5,380,245 A | 1/1995 | Reiterman et al. |
| 5,383,923 A | 1/1995 | Webster, Jr. |
| 5,396,893 A | 3/1995 | Oberg et al. |
| 5,403,311 A | 4/1995 | Abele et al. |
| 5,413,574 A | 5/1995 | Fugo |

(56) References Cited

U.S. PATENT DOCUMENTS

| | | |
|---|---|---|
| 5,423,779 A | 6/1995 | Yeh |
| 5,437,664 A | 8/1995 | Cohen |
| 5,441,499 A | 8/1995 | Fritzsch |
| 5,456,248 A | 10/1995 | Holian et al. |
| 5,456,683 A | 10/1995 | Fritzsch et al. |
| 5,458,597 A | 10/1995 | Edwards et al. |
| 5,465,248 A | 11/1995 | Fuji |
| 5,478,303 A | 12/1995 | Foley-nolan et al. |
| 5,505,728 A | 4/1996 | Ellman et al. |
| 5,514,131 A | 5/1996 | Edwards et al. |
| 5,562,503 A | 10/1996 | Ellman et al. |
| 5,571,101 A | 11/1996 | Ellman et al. |
| D376,423 S | 12/1996 | Monea |
| 5,594,686 A | 1/1997 | Hazen et al. |
| 5,599,347 A | 2/1997 | Hart et al. |
| 5,613,966 A | 3/1997 | Makower et al. |
| 5,620,441 A | 4/1997 | Gref et al. |
| 5,636,733 A | 6/1997 | Marchwiak |
| D382,342 S | 8/1997 | Rosen |
| 5,662,680 A | 9/1997 | Desai |
| 5,679,401 A | 10/1997 | Bawden |
| 5,683,387 A | 11/1997 | Garito et al. |
| 5,685,878 A | 11/1997 | Falwell et al. |
| D388,170 S | 12/1997 | Sjostrom |
| 5,709,675 A | 1/1998 | Williams |
| 5,713,942 A | 2/1998 | Stern et al. |
| D393,067 S | 3/1998 | Geary et al. |
| 5,733,282 A | 3/1998 | Ellman et al. |
| D393,715 S | 4/1998 | Strickland |
| 5,735,846 A * | 4/1998 | Panescu .............. A61B 18/12 606/41 |
| 5,741,250 A | 4/1998 | Garito et al. |
| 5,746,746 A | 5/1998 | Garito et al. |
| 5,755,716 A | 5/1998 | Garito et al. |
| 5,766,171 A | 6/1998 | Silvestrini |
| 5,769,702 A | 6/1998 | Hanson |
| 5,807,392 A | 9/1998 | Eggers |
| 5,814,044 A | 9/1998 | Hooven |
| 5,833,689 A | 11/1998 | Long |
| 5,836,897 A | 11/1998 | Sakurai et al. |
| D402,030 S | 12/1998 | Roberts et al. |
| 5,871,524 A | 2/1999 | Knowlton |
| 5,891,142 A | 4/1999 | Eggers |
| D409,335 S | 5/1999 | Slater |
| 5,916,158 A | 6/1999 | Webster, Jr. |
| 5,924,206 A | 7/1999 | Cote et al. |
| 5,925,039 A | 7/1999 | Landingham |
| 5,948,009 A | 9/1999 | Tu |
| 5,954,686 A | 9/1999 | Garito et al. |
| 5,984,918 A | 11/1999 | Garito et al. |
| 5,991,650 A * | 11/1999 | Swanson .............. A61L 31/145 606/41 |
| 5,993,447 A | 11/1999 | Blewett et al. |
| D417,371 S | 12/1999 | Searle et al. |
| 5,997,533 A | 12/1999 | Kuhns |
| 5,997,733 A | 12/1999 | Wilbur et al. |
| 6,001,077 A | 12/1999 | Ellman et al. |
| 6,006,755 A | 12/1999 | Edwards |
| 6,010,500 A | 1/2000 | Sherman et al. |
| D422,024 S | 3/2000 | Andrews et al. |
| 6,039,734 A | 3/2000 | Goble |
| 6,044,846 A | 4/2000 | Edwards |
| 6,050,993 A | 4/2000 | Tu et al. |
| 6,059,734 A | 5/2000 | Yoon |
| 6,063,085 A | 5/2000 | Tay et al. |
| 6,068,628 A | 5/2000 | Fanton et al. |
| 6,080,152 A | 6/2000 | Nardella et al. |
| D428,146 S | 7/2000 | Svanberg et al. |
| 6,093,186 A | 7/2000 | Goble |
| 6,102,046 A | 8/2000 | Weinstein et al. |
| 6,113,596 A | 9/2000 | Hooven et al. |
| 6,123,702 A * | 9/2000 | Swanson .............. A61B 18/1206 606/49 |
| D431,972 S | 10/2000 | Naft et al. |
| 6,156,032 A | 12/2000 | Lennox |
| 6,159,194 A | 12/2000 | Eggers et al. |
| 6,203,762 B1 | 3/2001 | Skalla et al. |
| 6,206,842 B1 | 3/2001 | Tu et al. |
| D441,007 S | 4/2001 | Simons et al. |
| 6,214,003 B1 | 4/2001 | Morgan et al. |
| 6,228,078 B1 | 5/2001 | Eggers et al. |
| 6,228,084 B1 | 5/2001 | Kirwan, Jr. |
| 6,231,571 B1 | 5/2001 | Ellman et al. |
| 6,235,027 B1 | 5/2001 | Herzon |
| 6,238,388 B1 | 5/2001 | Ellman et al. |
| 6,238,394 B1 | 5/2001 | Garito et al. |
| 6,245,068 B1 | 6/2001 | Olson et al. |
| 6,251,110 B1 | 6/2001 | Wampler |
| 6,280,441 B1 | 8/2001 | Ryan |
| 6,296,637 B1 | 10/2001 | Thorne et al. |
| 6,312,428 B1 | 11/2001 | Eggers et al. |
| D453,222 S | 1/2002 | Garito et al. |
| 6,348,051 B1 | 2/2002 | Farin et al. |
| 6,355,032 B1 | 3/2002 | Hovda et al. |
| 6,368,324 B1 | 4/2002 | Dinger et al. |
| 6,387,092 B1 | 5/2002 | Burnside et al. |
| 6,387,093 B1 | 5/2002 | Ellman et al. |
| 6,395,001 B1 | 5/2002 | Ellman et al. |
| 6,402,742 B1 | 6/2002 | Blewett et al. |
| 6,409,726 B1 | 6/2002 | Ellman et al. |
| 6,413,255 B1 * | 7/2002 | Stern .............. A61B 18/14 606/41 |
| 6,416,512 B1 | 7/2002 | Ellman et al. |
| 6,417,532 B2 | 7/2002 | Tsunoda et al. |
| 6,432,105 B1 | 8/2002 | Ellman et al. |
| 6,447,509 B1 | 9/2002 | Bonnet et al. |
| 6,461,352 B2 | 10/2002 | Morgan et al. |
| 6,506,267 B1 | 1/2003 | Fujiyasu et al. |
| 6,517,532 B1 | 2/2003 | Altshuler et al. |
| 6,530,924 B1 | 3/2003 | Ellman et al. |
| 6,540,745 B1 | 4/2003 | Fairbourn et al. |
| 6,544,210 B1 | 4/2003 | Trudel et al. |
| 6,546,935 B2 | 4/2003 | Hooven |
| 6,562,032 B1 | 5/2003 | Ellman et al. |
| 6,562,036 B1 | 5/2003 | Ellman et al. |
| 6,565,561 B1 | 5/2003 | Goble et al. |
| 6,572,613 B1 | 6/2003 | Ellman et al. |
| 6,582,427 B1 | 6/2003 | Goble et al. |
| 6,585,791 B1 | 7/2003 | Garito et al. |
| 6,592,580 B1 | 7/2003 | Stockert |
| 6,605,080 B1 | 8/2003 | Altshuler et al. |
| 6,607,528 B1 | 8/2003 | Quick et al. |
| 6,613,047 B2 | 9/2003 | Edwards |
| 6,613,048 B2 | 9/2003 | Mulier et al. |
| D481,841 S | 11/2003 | Hsu |
| 6,652,514 B2 | 11/2003 | Ellman et al. |
| 6,663,620 B2 | 12/2003 | Altshuler et al. |
| 6,673,072 B1 | 1/2004 | Garito et al. |
| 6,679,881 B1 | 1/2004 | Bybee |
| 6,689,071 B2 | 2/2004 | Burbank et al. |
| 6,694,707 B2 | 2/2004 | Lehner et al. |
| 6,730,323 B1 | 5/2004 | Murley et al. |
| 6,749,608 B2 | 6/2004 | Garito et al. |
| 6,759,624 B2 | 7/2004 | Kumar et al. |
| 6,766,202 B2 | 7/2004 | Underwood et al. |
| 6,767,348 B2 | 7/2004 | Nakada et al. |
| D494,270 S | 8/2004 | Reschke |
| 6,802,842 B2 | 10/2004 | Ellman et al. |
| D500,168 S | 12/2004 | Ho |
| 6,830,569 B2 | 12/2004 | Thompson et al. |
| D500,854 S | 1/2005 | Eichel |
| 6,837,884 B2 | 1/2005 | Woloszko |
| 6,892,580 B2 | 5/2005 | Pankey et al. |
| 6,920,883 B2 | 7/2005 | Bessette et al. |
| 6,926,717 B1 | 8/2005 | Garito et al. |
| D510,138 S | 9/2005 | Kim |
| D510,158 S | 9/2005 | Cheung |
| 6,974,451 B2 | 12/2005 | Altshuler et al. |
| 6,976,985 B2 | 12/2005 | Altshuler et al. |
| 6,994,707 B2 | 2/2006 | Ellman et al. |
| 7,070,604 B1 | 7/2006 | Garito et al. |
| 7,090,649 B2 | 8/2006 | Kang |
| 7,094,231 B1 | 8/2006 | Ellman et al. |
| D533,943 S | 12/2006 | Chen |

(56) References Cited

U.S. PATENT DOCUMENTS

| | | |
|---|---|---|
| 7,147,634 B2 | 12/2006 | Nesbitt |
| D535,397 S | 1/2007 | Chen |
| 7,156,844 B2 | 1/2007 | Reschke et al. |
| 7,160,295 B1 | 1/2007 | Garito et al. |
| 7,163,336 B2 | 1/2007 | Blakeley, III |
| D538,936 S | 3/2007 | Böhmel et al. |
| D548,843 S | 8/2007 | Kertz |
| 7,258,689 B2 | 8/2007 | Salvo |
| 7,276,058 B2 | 10/2007 | Altshuler et al. |
| D555,803 S | 11/2007 | Garito et al. |
| 7,351,252 B2 | 4/2008 | Altshuler et al. |
| 7,422,586 B2 | 9/2008 | Morris et al. |
| 7,427,289 B2 | 9/2008 | Sierra et al. |
| 7,473,251 B2 | 1/2009 | Knowlton et al. |
| 7,479,140 B2 | 1/2009 | Ellman et al. |
| 7,507,232 B1 | 3/2009 | Garito et al. |
| D591,365 S | 4/2009 | Pasko et al. |
| 7,572,251 B1 | 8/2009 | Davison et al. |
| D601,803 S | 10/2009 | Reishus et al. |
| D609,817 S | 2/2010 | Piller et al. |
| D612,510 S | 3/2010 | Byle |
| 7,674,261 B2 | 3/2010 | Garito et al. |
| 7,749,218 B2 | 7/2010 | Pellegrino et al. |
| 7,763,016 B2 | 7/2010 | Altshuler et al. |
| D625,412 S | 10/2010 | Garito et al. |
| D628,304 S | 11/2010 | Aulwes et al. |
| 7,828,794 B2 | 11/2010 | Sartor |
| 7,875,026 B1 | 1/2011 | Garito et al. |
| 7,879,032 B1 | 2/2011 | Garito et al. |
| 7,879,033 B2 | 2/2011 | Sartor et al. |
| 7,935,110 B1 | 5/2011 | Garito et al. |
| 7,947,037 B1 | 5/2011 | Garito et al. |
| 7,955,327 B2 | 6/2011 | Sartor et al. |
| 7,959,633 B2 | 6/2011 | Sartor et al. |
| 7,975,702 B2 | 7/2011 | Cho et al. |
| 8,002,768 B1 | 8/2011 | Altshuler et al. |
| 8,016,824 B2 | 9/2011 | Buchman, II et al. |
| D646,487 S | 10/2011 | Leppla et al. |
| D652,524 S | 1/2012 | Messner |
| 8,100,898 B2 | 1/2012 | Gregg |
| 8,100,902 B2 | 1/2012 | Sartor |
| 8,113,209 B2 | 2/2012 | Masotti et al. |
| 8,128,622 B2 | 3/2012 | Podhajsky et al. |
| 8,162,937 B2 | 4/2012 | Cunningham et al. |
| D660,448 S | 5/2012 | Lum et al. |
| 8,172,835 B2 | 5/2012 | Leyh et al. |
| 8,190,243 B2 | 5/2012 | Welches et al. |
| 8,231,620 B2 | 7/2012 | Mathonnet |
| 8,235,987 B2 | 8/2012 | Craig |
| 8,251,989 B1 | 8/2012 | Newton et al. |
| 8,317,782 B1 | 11/2012 | Ellman et al. |
| 8,321,031 B1 | 11/2012 | Ellman et al. |
| 8,359,104 B2 | 1/2013 | Epstein et al. |
| D675,829 S | 2/2013 | Jakubow |
| D679,502 S | 4/2013 | Itano et al. |
| 8,449,540 B2 | 5/2013 | Sartor et al. |
| 8,454,591 B2 | 6/2013 | Leyh et al. |
| 8,460,289 B2 | 6/2013 | Sartor |
| 8,506,565 B2 | 8/2013 | Decarlo |
| 8,540,705 B2 | 9/2013 | Mehta |
| 8,591,509 B2 | 11/2013 | Fry et al. |
| 8,597,292 B2 | 12/2013 | Kerr |
| 8,608,737 B2 | 12/2013 | Mehta et al. |
| 8,632,536 B2 | 1/2014 | Kerr et al. |
| 8,636,733 B2 | 1/2014 | Heard |
| D698,921 S | 2/2014 | Koennecke et al. |
| 8,663,128 B2 | 3/2014 | Paz et al. |
| 8,663,216 B2 | 3/2014 | Davison et al. |
| 8,663,218 B2 | 3/2014 | Heard et al. |
| 8,663,219 B2 | 3/2014 | Heard et al. |
| 8,668,688 B2 | 3/2014 | Rusin |
| D713,150 S | 9/2014 | Maurin et al. |
| 8,845,630 B2 | 9/2014 | Mehta et al. |
| 8,915,948 B2 | 12/2014 | Altshuler et al. |
| 8,945,124 B2 | 2/2015 | Craig |
| 8,961,511 B2 | 2/2015 | Parmer |
| 8,998,891 B2 | 4/2015 | Garito et al. |
| D728,242 S | 5/2015 | Kim et al. |
| D732,164 S | 6/2015 | Woloszko et al. |
| D733,290 S | 6/2015 | Burton et al. |
| D736,462 S | 8/2015 | Hendler et al. |
| 9,132,058 B2 | 9/2015 | Imboden et al. |
| D742,647 S | 11/2015 | Hosier et al. |
| 9,271,785 B2 | 3/2016 | Parmer et al. |
| D757,953 S | 5/2016 | Philips |
| 9,345,531 B2 | 5/2016 | Furnish et al. |
| 9,415,235 B2 | 8/2016 | Galen et al. |
| D767,897 S | 10/2016 | Hosler et al. |
| D773,676 S | 12/2016 | Gufler |
| D793,186 S | 8/2017 | Tinius |
| D805,781 S | 12/2017 | Szymanski et al. |
| D809,139 S | 1/2018 | Marsot et al. |
| D821,759 S | 7/2018 | Szymanski et al. |
| D823,478 S | 7/2018 | Park |
| D830,700 S | 10/2018 | Xue |
| D831,905 S | 10/2018 | Benacquisto et al. |
| D835,845 S | 12/2018 | Graves et al. |
| 10,143,831 B2 | 12/2018 | Juergens et al. |
| D837,395 S | 1/2019 | Gan |
| D839,601 S | 2/2019 | Fang |
| D840,547 S | 2/2019 | Harle et al. |
| D842,491 S | 3/2019 | Fleming et al. |
| D848,677 S | 5/2019 | Thalmann |
| D860,441 S | 9/2019 | Spycher et al. |
| D863,574 S | 10/2019 | Yan et al. |
| D863,580 S | 10/2019 | Lee |
| D864,407 S | 10/2019 | Zhou |
| D870,294 S | 12/2019 | Bechtel et al. |
| D870,304 S | 12/2019 | Du |
| 10,492,849 B2 | 12/2019 | Juergens et al. |
| 10,518,097 B2 | 12/2019 | Grez |
| D873,569 S | 1/2020 | Nichols |
| D883,675 S | 5/2020 | Wong et al. |
| D884,203 S | 5/2020 | Segev |
| D892,322 S | 8/2020 | Yang |
| D901,034 S | 11/2020 | Zhang et al. |
| D902,403 S | 11/2020 | Marsot et al. |
| D905,237 S | 12/2020 | Knieriem et al. |
| D905,238 S | 12/2020 | Englert et al. |
| D905,239 S | 12/2020 | Englert et al. |
| D913,483 S | 3/2021 | Boschetti Sacco |
| D919,814 S | 5/2021 | Zikria et al. |
| D969,317 S | 11/2022 | Sun et al. |
| D975,275 S | 1/2023 | Ueda et al. |
| D979,751 S | 2/2023 | Harvey et al. |
| 2001/0018606 A1 | 8/2001 | Ingle et al. |
| 2002/0029036 A1 | 3/2002 | Goble et al. |
| 2002/0032439 A1 | 3/2002 | Hareyama |
| 2002/0077626 A1 | 6/2002 | Ellman et al. |
| 2002/0115991 A1 | 8/2002 | Edwards |
| 2002/0133149 A1 | 9/2002 | Bessette et al. |
| 2002/0188284 A1 | 12/2002 | To et al. |
| 2003/0009165 A1 | 1/2003 | Edwards et al. |
| 2003/0050634 A1 | 3/2003 | Ellman et al. |
| 2003/0216727 A1 | 3/2003 | Long |
| 2003/0112204 A1 | 6/2003 | Pettersen |
| 2003/0130653 A1* | 7/2003 | Sixto, Jr. ............ A61B 18/1482 606/45 |
| 2003/0130711 A1 | 7/2003 | Pearson et al. |
| 2003/0139741 A1 | 7/2003 | Goble et al. |
| 2003/0139753 A1 | 7/2003 | Wang et al. |
| 2003/0153906 A1 | 8/2003 | Sharkey et al. |
| 2003/0158545 A1 | 8/2003 | Hovda et al. |
| 2003/0159700 A1 | 8/2003 | Laufer et al. |
| 2003/0163178 A1 | 8/2003 | Davison et al. |
| 2003/0216725 A1 | 11/2003 | Woloszko et al. |
| 2003/0216728 A1 | 11/2003 | Stern et al. |
| 2003/0233037 A1* | 12/2003 | Bencini ............ A61B 18/1492 600/374 |
| 2003/0236487 A1 | 12/2003 | Knowlton |
| 2004/0002705 A1 | 1/2004 | Knowlton et al. |
| 2004/0006339 A1 | 1/2004 | Underwood et al. |
| 2004/0024433 A1 | 2/2004 | Roy et al. |
| 2004/0030329 A1 | 2/2004 | Hagg |

(56) References Cited

U.S. PATENT DOCUMENTS

| | | |
|---|---|---|
| 2004/0049251 A1 | 3/2004 | Knowlton |
| 2004/0054365 A1 | 3/2004 | Goble |
| 2004/0064175 A1 | 4/2004 | Lessar et al. |
| 2004/0111087 A1 | 6/2004 | Stern et al. |
| 2004/0116979 A1 | 6/2004 | Truckai et al. |
| 2004/0167516 A1 | 8/2004 | Cucin |
| 2004/0181213 A1 | 9/2004 | Gondo |
| 2004/0186535 A1 | 9/2004 | Knowlton |
| 2004/0210214 A1 | 10/2004 | Knowlton |
| 2004/0236203 A1 | 11/2004 | Salvo |
| 2005/0004564 A1 | 1/2005 | Wham et al. |
| 2005/0027235 A1 | 2/2005 | Knudsen et al. |
| 2005/0059889 A1 | 3/2005 | Mayer |
| 2005/0090816 A1 | 4/2005 | Mcclurken et al. |
| 2005/0137662 A1 | 6/2005 | Morris et al. |
| 2005/0154385 A1 | 7/2005 | Heim et al. |
| 2005/0256524 A1 | 11/2005 | Long et al. |
| 2005/0267465 A1 | 12/2005 | Hillier et al. |
| 2006/0009757 A1 | 1/2006 | Long |
| 2006/0009763 A1 | 1/2006 | Goble et al. |
| 2006/0052847 A1 | 3/2006 | Davenport et al. |
| 2006/0173518 A1 | 8/2006 | Kreindel |
| 2006/0259102 A1 | 11/2006 | Slatkine |
| 2007/0005053 A1 | 1/2007 | Dando |
| 2007/0055226 A1 | 3/2007 | Garito et al. |
| 2007/0083247 A1 | 4/2007 | Wyeth et al. |
| 2007/0088413 A1 | 4/2007 | Weber et al. |
| 2007/0093804 A1 | 4/2007 | Kaveckis et al. |
| 2007/0093805 A1 | 4/2007 | Auth et al. |
| 2007/0106349 A1 | 5/2007 | Kami et al. |
| 2007/0112342 A1 | 5/2007 | Pearson et al. |
| 2007/0161981 A1 | 7/2007 | Sanders et al. |
| 2007/0213700 A1 | 9/2007 | Davison et al. |
| 2007/0213792 A1 | 9/2007 | Yaroslavsky et al. |
| 2007/0233191 A1 | 10/2007 | Parmer |
| 2007/0282318 A1 | 12/2007 | Spooner et al. |
| 2008/0004678 A1 | 1/2008 | Kreindel |
| 2008/0009849 A1* | 1/2008 | Goble ............ A61B 18/12 606/34 |
| 2008/0051777 A1 | 2/2008 | Haemmerich |
| 2008/0058796 A1 | 3/2008 | O'brien et al. |
| 2008/0091184 A1 | 4/2008 | Knopp et al. |
| 2008/0091185 A1 | 4/2008 | Mcgill et al. |
| 2008/0119846 A1 | 5/2008 | Rioux |
| 2008/0125775 A1 | 5/2008 | Morris |
| 2008/0183251 A1 | 7/2008 | Azar et al. |
| 2008/0262490 A1 | 10/2008 | Williams et al. |
| 2008/0312651 A1 | 12/2008 | Pope et al. |
| 2009/0012511 A1 | 1/2009 | Welches et al. |
| 2009/0018531 A1 | 1/2009 | Welches et al. |
| 2009/0024192 A1* | 1/2009 | Mulholland ....... A61B 18/1477 607/99 |
| 2009/0036958 A1 | 2/2009 | Mehta |
| 2009/0054956 A1 | 2/2009 | Sierra et al. |
| 2009/0062786 A1 | 3/2009 | Garito et al. |
| 2009/0093864 A1 | 4/2009 | Anderson et al. |
| 2009/0112204 A1 | 4/2009 | Aronow et al. |
| 2009/0112205 A1 | 4/2009 | Mcgill et al. |
| 2009/0138011 A1 | 5/2009 | Epstein |
| 2009/0171341 A1 | 7/2009 | Pope et al. |
| 2009/0248004 A1 | 10/2009 | Altshuler et al. |
| 2009/0248022 A1 | 10/2009 | Falkenstein et al. |
| 2009/0306647 A1 | 12/2009 | Leyh et al. |
| 2009/0306648 A1 | 12/2009 | Podhajsky et al. |
| 2010/0023008 A1 | 1/2010 | Heard et al. |
| 2010/0030107 A1 | 2/2010 | Hancock |
| 2010/0030212 A1 | 2/2010 | Aramayo |
| 2010/0045427 A1 | 2/2010 | Boone, III et al. |
| 2010/0049178 A1 | 2/2010 | Deem et al. |
| 2010/0114088 A1 | 5/2010 | Buchman, II et al. |
| 2010/0211060 A1 | 8/2010 | Baron et al. |
| 2010/0217254 A1 | 8/2010 | Mehta |
| 2010/0228243 A1 | 9/2010 | Mehta |
| 2010/0228244 A1 | 9/2010 | Hancock et al. |
| 2010/0241116 A1 | 9/2010 | Benamou et al. |
| 2010/0249772 A1 | 9/2010 | Mehta et al. |
| 2010/0262135 A1 | 10/2010 | Berube |
| 2010/0312233 A1 | 12/2010 | Furnish et al. |
| 2011/0046523 A1 | 2/2011 | Altshuler et al. |
| 2011/0066145 A1* | 3/2011 | Epstein ............ A61B 18/14 606/33 |
| 2011/0087215 A1 | 4/2011 | Aldridge et al. |
| 2011/0087216 A1 | 4/2011 | Aldridge et al. |
| 2011/0144729 A1 | 6/2011 | Weber |
| 2011/0178584 A1 | 7/2011 | Parmer et al. |
| 2011/0218464 A1 | 9/2011 | Iger |
| 2011/0238056 A1 | 9/2011 | Koss et al. |
| 2011/0276046 A1 | 11/2011 | Heimbecher et al. |
| 2012/0002512 A1 | 1/2012 | Matsuzaki |
| 2012/0022504 A1 | 1/2012 | Epshtein et al. |
| 2012/0022510 A1 | 1/2012 | Welches et al. |
| 2012/0095461 A1 | 4/2012 | Herscher et al. |
| 2012/0191072 A1 | 7/2012 | Hancock |
| 2012/0265193 A1 | 10/2012 | Lischinsky et al. |
| 2012/0265196 A1 | 10/2012 | Turner et al. |
| 2013/0006239 A1 | 1/2013 | Pikramenos et al. |
| 2013/0245727 A1 | 9/2013 | Kothare et al. |
| 2013/0245728 A1 | 9/2013 | Galen et al. |
| 2013/0274841 A1 | 10/2013 | Eckhous et al. |
| 2013/0296835 A1 | 11/2013 | Sierra et al. |
| 2014/0025033 A1 | 1/2014 | Mirkov et al. |
| 2014/0182335 A1 | 7/2014 | Lee et al. |
| 2014/0276768 A1 | 9/2014 | Juergens et al. |
| 2015/0005759 A1 | 1/2015 | Welches et al. |
| 2015/0025526 A1* | 1/2015 | Hua ............... A61B 18/1492 606/34 |
| 2015/0094914 A1 | 4/2015 | Abreu |
| 2015/0196351 A1* | 7/2015 | Stone ............ A61N 1/28 606/41 |
| 2015/0297908 A1 | 10/2015 | Alinsod et al. |
| 2015/0327926 A1 | 11/2015 | Parmer |
| 2016/0135876 A1 | 5/2016 | Parmer et al. |
| 2016/0256701 A1 | 9/2016 | Furnish et al. |
| 2016/0263387 A1 | 9/2016 | Alinsod et al. |
| 2016/0263388 A1 | 9/2016 | Alinsod et al. |
| 2016/0263389 A1 | 9/2016 | Alinsod et al. |
| 2016/0296278 A1 | 10/2016 | Galen et al. |
| 2017/0071651 A1 | 3/2017 | Allan et al. |
| 2017/0182334 A1 | 6/2017 | Altshuler et al. |
| 2017/0182335 A1 | 6/2017 | Altshuler et al. |
| 2017/0333249 A1 | 11/2017 | Herchman, Jr. et al. |
| 2018/0001103 A9 | 1/2018 | Alinsod et al. |

FOREIGN PATENT DOCUMENTS

| | | |
|---|---|---|
| CN | 101905059 | 12/2010 |
| DE | 2011035 | 10/1970 |
| DE | 3627221 | 2/1988 |
| DE | 9102778 | 5/1991 |
| DE | 4423216 | 8/1995 |
| DE | 19850663 | 3/2001 |
| DE | 10138235 | 1/2003 |
| EP | 0368532 | 5/1990 |
| EP | 0423757 | 4/1991 |
| EP | 0480639 | 4/1992 |
| EP | 0332308 | 9/1998 |
| EP | 1707147 | 10/2006 |
| EP | 2258296 | 12/2010 |
| EP | 2742891 | 6/2014 |
| EP | 2790603 | 10/2014 |
| EP | 2967711 | 1/2016 |
| GB | 154881 | 9/1985 |
| GB | 490788 | 11/2012 |
| HK | 20154360005 | 6/2020 |
| JP | S60180394 | 9/1985 |
| JP | S63317073 | 12/1988 |
| JP | H0795985 | 4/1995 |
| JP | H07124101 | 5/1995 |
| JP | H08168495 | 7/1996 |
| JP | 2006-271968 | 10/2006 |
| JP | 2001523513 | 11/2011 |
| JP | 2012254312 | 12/2012 |
| KR | 10-2017-0035486 | 3/2017 |
| KR | 20170035486 | 3/2017 |

(56) References Cited

FOREIGN PATENT DOCUMENTS

| KR | 101757131 | 7/2017 |
|---|---|---|
| WO | 9426228 | 11/1994 |
| WO | 1996022742 | 8/1996 |
| WO | 9634569 | 11/1996 |
| WO | 1996039088 | 12/1996 |
| WO | 1997015238 | 5/1997 |
| WO | 1998016162 | 4/1998 |
| WO | 9838932 | 9/1998 |
| WO | 1999026546 | 6/1999 |
| WO | 2003103522 | 12/2003 |
| WO | 2004090939 | 10/2004 |
| WO | 2008012827 | 1/2008 |
| WO | 2008112931 | 9/2008 |
| WO | 2009031995 | 3/2009 |
| WO | 2009053117 | 4/2009 |
| WO | 2012052986 | 4/2012 |
| WO | 2013090528 | 6/2013 |
| WO | 2014145148 | 9/2014 |

OTHER PUBLICATIONS

Office Action in Canadian Application No. 3,089,137, dated Aug. 11, 2021, 3 pages.
Non-Final Office Action for U.S. Appl. No. 14/214,627, dated Apr. 10, 2019, 19 pages.
Final Office Action for U.S. Appl. No. 14/214,627, dated Sep. 21, 2018, 24 pages.
Non-Final Office Action for U.S. Appl. No. 14/214,627, dated May 25, 2018, 23 pages.
Final Office Action for U.S. Appl. No. 14/214,627, dated Oct. 31, 2018, 26 pages.
Non-Final Office Action for U.S. Appl. No. 14/214,627, dated Jul. 14, 2017, 22 pages.
Final Office Action for U.S. Appl. No. 14/214,627, dated Mar. 8, 2017, 21 pages.
Non-Final Office Action for U.S. Appl. No. 14/214,627, dated Aug. 19, 2016, 16 pages.
Extended European Search Report dated Nov. 4, 2016 in European Application No. 14762910.9.
Brunelle et al., A Bipolar Electrode for Vascular Electrocoagulation with Alternating Current. Radiology, vol. 137, No. 1, pp. 239 240, Oct. 1980.
Kushikata, et al., (2005). 'Is topical anesthesia useful in noninvasive skin tightening using radiofrequency?' J. Dermatologic Surgery 2005; 31:526-533. (8 page total).
Fritz, et al. (2004). 'Radiofrequency treatment for middle and lower face laxity'. Arch Facial Plastic Surgery 2004; 6:370-373. (4 pages total).
Fritzpatrick, et al. (2003). 'Multicenter study of noninvasive radiofrequency for periorbital tissue tightening'. Lasers in Surgery and Medicine 2003; 33:232-242. (11 page total).
Maximum Power Transfer Theorem-Electronics Hub. http://www.electronicshub.org/maximum-power-transfer-therein/. Accessed Thu Oct. 26, 2017.
Maximum Power Transfer Theorem in DC Theory, http://www.electronics-tutorials.ws/dccircuits/dcp_9.html. Accessed Oct. 31, 2019.
Zelickson, Brian D., et al., "Histological and Ultrastructural Evaluation of the Effects of Radiofrequency-Based Nonablative Dermal Remodeling Device," Arch Dermatol, 2004, pp. 204-209, vol. 140, American Medical Association, United States.
Hantash, Basil M., et al., "Bipolar Fractional Radiofrequency Treatment Induces Neoelastogenesis and Neocollagenesis," Lasers in Surgery and Medicine, 2009, pp. 1-9, vol. 41, Wiley-Liss, Inc., United States.
Gonzalez-Suarez, Ana, et al., "Thermal and Elastic Response of Subcutaneous Tissue With Different Fibrous Septa Architectures to RF Heating: Numerical Study," Lasers in Surgery and Medicine, Oct. 4, 2015, pp. 183-195, vol. 47, Wiley Periodicals, Inc., United States.

Kist, David, et al., "Ultrastructural Evaluation of Multiple Pass Low Energy Versus Single Pass High Energy Radio-Frequency Treatment," Lasers in Surgery and Medicine, Jan. 5, 2006, pp. 150-154, vol. 38, Wiley-Liss, Inc., United States.
The Effect of Heat on Collagen and Neocollagenesis, Ultherapy.com, Jul. 20, 2011, 78 pages, available from http://www.ultherapy.com/uploads/document/professional/Effects-of-Temperature-on-Collagen.pdf. (last accessed May 9, 2018).
Abraham, Manoj T., et al. "Monopolar Radiofrequency Skin Tightening," Facial Plastic Surgery Clinics of North America, 2007, pp. 169-177, vol. 15, Elsevier Inc.
Sadick, Neil, "Tissue Tightening Technologies: Fact or Fiction," Aesthetic Surgery Journal, Dec. 11, 2007, pp. 180-188, vol. 28 No. 2, Sage Publications, United States.
Lauback, Hans J., et al., "Intense Focused Ultrasound: Evaluation of a New Treatment Modality for Precise Microcoagulation within the Skin," American Society for Dermatologic Surgery, Inc., May 2008, pp. 727-734, vol. 34, Blackwell Publishing, United States.
Third Examination Report in Australian Application No. 2019217623, dated Sep. 21, 2021, 4 pages.
Extended European Search Report in European U.S. Appl. No. 19/750,304, dated Oct. 21, 2021, 6 pages.
White, W. Matthew, et al., "Selective Transcutaneous Delivery of Energy to Porcine Soft Tissues Using Intense Ultrasound (IUS)," Lasers in Surgery and Medicine, Dec. 27, 2008, pp. 67-75, vol. 40, Wiley-Liss, Inc., United States.
Hayashi, Kei, et al., "The Effect of Thermal Heating on the Length and Histologic Properties of the Glenohumeral Joint Capsule," The American Journal of Sports Medicine, 1997, pp. 107-112, vol. 25 No. 1, Sage Publications, United States.
Vangsness Jr., C. Thomas, et al., "Collagen Shortening: An Experimental Approach with Heat," Clinical Orthopedics and Related Research, Mar. 24, 1997, pp. 267-271, vol. 337, Lippincott-Raven Publishers.
Lin, Sung-Jan, et al., "Monitoring the Thermally Induced Structural Transitions of Collagen by Use of Second-Harmonic Generation Microscopy," Optics Letters, Mar. 15, 2005, pp. 622-624, vol. 30 No. 6, Optical Society of America.
Paul, Malcolm, et al., "Three-Dimensional Radiofrequency Tissue Tightening: A Proposed Mechanism and Applications for Body Contouring," Aesth Plastic Surgery, Jul. 6, 2010, pp. 87-95, vol. 35., Springer.
Hayashi, Kei, et al., "Effect of Nonablative Laser Energy on the Joint Capsule: An in Vivo Rabbit Study Using a Holmium: YAG Laser," Lasers in Surgery and Medicine, Feb. 21, 1997, pp. 164-171, vol. 20, Wiley-Liss, Inc., United States.
Invitation to Pay Additional Fees for PCT Application No. PCT/US2017/040585, dated Oct. 13, 2017, 23 pages.
International Search Report and Written Opinion for PCT Application No. PCT/US2017/040585, dated Dec. 6, 2017, 24 pages.
Third Party Submission in PCT Application No. PCT/US2017/040585, filed Jan. 29, 2018, 30 pages.
Third Party Submission in U.S. Appl. No. 15/640,710, filed Feb. 7, 2018, 58 pages.
International Search Report and Written Opinion of the International Searching Authority in PCT/US14/29862 dated Oct. 23, 2014.
Non-Final Office Action for U.S. Appl. No. 14/205,021, dated Jul. 28, 2016.
Chinese-language Office Action (with English-language translation provided) dated Jul. 12, 2012, issued by China's State Intellectual Property Office in Chinese Application No. 201010201340.2, 4 pages.
European Search Report for European U.S. Appl. No. 10/164,893, dated Oct. 11, 2010, 6 pages.
European Search Report dated Jan. 23, 2009 for European Patent application No. 08252879.5; 9 pages.
Office Action for Japanese Application No. 2008-218931, dated Feb. 5, 2013, 4 pages.
Notice of Reasons for Refusal for Japanese Application No. 2008-218931, dated Aug. 5, 2013, 6 pages.
European Search Report for European Application No. 10176756.4, dated Dec. 28, 2010, 5 pages.

(56) References Cited

OTHER PUBLICATIONS

European Search Report for European U.S. Appl. No. 99303449, dated Oct. 6, 1999, 3 pages.
Extended European Search Report dated Nov. 8, 2016 in European Patent Application No. 14768330.4.
International Search Report and Written Opinion for PCT Application No. PCT/US2014/029862, dated Oct. 23, 2014.
Examination Report in Australian Application No. 2019217623, dated Oct. 27, 2020, 5 pages.
International Search Report and Written Opinion in PCT Application No. PCT/US2019/016883, dated Jun. 24, 2019, 12 pages.
Office Action in Canadian Application No. 3089137, dated Jun. 2, 2022, 4 pages.
Notice of Allowance in U.S. Appl. No. 16/684,937, dated May 20, 2022, 11 pages.
Ex parte Quayle Action for U.S. Appl. No. 29/698,791, dated Jun. 7, 2022, 7 pages.
Non-Final Office Action in U.S. Appl. No. 16/684,937, dated Mar. 2, 2022, 8 pages.
Restriction Requirement for U.S. Appl. No. 29/698,791, dated Mar. 29, 2022, 11 pages.
Office Action in Korean Application No. 10-2020-7025344, dated Mar. 29, 2022, 10 pages.
Office Action in Chinese Application No. 2019800125366, dated Jan. 28, 2023, 6 pages.
Notice of Allowance in Korean Application No. 10-2020-7025344, dated Nov. 25, 2022, 5 pages.
First Examination Report in Australian Application No. 2021245265, dated Nov. 1, 2022, 4 pages.
Australian Office Action for Australian Application No. 2021245265, dated Mar. 28, 2023, 4 pages.
Office Action in Canadian Application No. 3089137, dated Mar. 15, 2023, 3 pages.
Third Examination Report in Australian Application No. 2021245265, dated Jun. 16, 2023, 5 pages.

* cited by examiner

METHODS AND APPARATUS FOR CONTROLLED RF TREATMENTS AND RF GENERATOR SYSTEM

BACKGROUND

The subject matter disclosed herein (referred to as the "disclosure") generally pertains to electrosurgical systems, such as, for example, electrosurgical devices and related electrical circuitry and methods. More particularly, but not exclusively, this disclosure relates, in part, to electrosurgical systems and components thereof configured to deliver radio-frequency (RF) energy to a target site of a human or other animal patient with selectable RF energy delivery profiles, temperature sensors and controls, and/or electrodes configured to more uniformly or effectively deliver energy to target tissue. In some respects, this disclosure pertains to electrosurgical methods and systems for providing electrosurgical treatments.

U.S. Publication No. 2013/0006239, which is hereby incorporated by reference herein in its entirety, for all purposes, is commonly owned with this application and discloses a representative, known electrosurgical system, as seen in FIG. 34 of the instant application. The electrosurgical system includes a control unit 34 and an electrosurgical device 10. In this embodiment, the electrosurgical device 10 (sometimes referred to as a "handpiece") includes a housing 12, e.g., for containing circuitry, and an energizable electrode 18 configured to treat a target site on or in a patient's body. The housing 12 can be configured as a graspable component of the handpiece, as shown for example in FIG. 34. In other instances, the graspable portion of the handpiece may be spaced from a circuit-containing housing.

The control unit 34 is configured to provide power to the electrosurgical device 10 for energizing the electrode. The control unit 34 can be configured to provide energy having a selected combination of waveform and frequency. Some control units 34 are configured to provide RF energy to the electrosurgical device 10.

As FIG. 34 shows, a cable 32 can extend between an electrical connector 33 on the control unit 34 and an electrical connector 31 on the electrosurgical device to electrically couple one or more conductive elements on or within the device 10 to one or more corresponding conductive elements of the controller 34. Some known control units provide three output terminals, with one of the terminals being an energizable terminal for conveying therapeutic energy, e.g., RF energy, to an energizable element of a handpiece. Such a control unit 34 is usually configured to energize the energizable terminal when a circuit between the two remaining output terminals is completed, as through the closing of a user actuatable switch 14.

Some known electrosurgical control units, such as control units are described, for example, in U.S. Pat. No. 6,652,514, which is hereby incorporated by reference herein by reference in its entirety, provides a three-wire output connector for powering and controlling electrosurgical handpieces. Conventional control units can generate, for example, one or more radio-frequency (RF) modulated waveforms, including, for one non-limiting example, at a frequency of about 4 mega-Hertz (MHz), which can be delivered to a target site by way of an electrosurgical handpiece having an energizable electrode defining an active surface.

The active surface of an electrosurgical system can be configured for ablative and/or non-ablative electrosurgery, depending on the physical configuration of the active surface and applied-power parameters. As used herein, an ablative procedure is one where the electrode and power settings result in cutting, coagulation, vaporization or other such traumatic disruption to the integrity of treated tissue, and a non-ablative procedure is one where such cutting, coagulation, vaporization or other such traumatic disruption to the integrity of treated tissue does not result.

SUMMARY

Principles disclosed herein overcome many problems in the prior art and address one or more of the aforementioned as well as other needs. This disclosure generally, but not exclusively, pertains to certain aspects of electrosurgical systems, devices, and methods. And they include, without limitation, the following innovative concepts:

Blend Mode—Adjustability of Waveform

Certain embodiments of the inventive subject matter are directed to two or more adjustable power sources each having independent switches to independently feed into an RF amplifier. Where solely cut mode is desired, only one of the power sources is employed. Where solely coagulation mode is desired, only the other of the power sources is employed. Where a blend of cut and coagulation is desired, both of the two adjustable power sources having independent switches are employed.

This concept advantageously enables excellent control over the wave form achieved in each mode, especially where blend is employed. This provides excellent control of the hemostatic effect on the tissue such that a small amount of coagulative effect might be desired on a surface and a larger amount of coagulative effect might be desired on internal organs/tissues. The reduction of coagulative effect is useful on the surface tissue because it provides less thermal damage adjacent to the cut and in this way, there can be balance between bleeding and undesirable scarring related to coagulative effects on tissue caused by excessive coagulation.

This concept advantageously enables the ability to control and to transition from cut to blend to coagulation and enables, in some embodiments, a single electrosurgical tip to be employed to make the initial cut through the skin surface in cut mode and to cut internal tissue layers with some coagulation to prevent unnecessary bleeding (in blend mode) and/or to solely coagulate tissue in coagulation mode. This can avoid multiple instruments being employed and, in some embodiments, instead a single electrosurgical tip may be employed during a procedure.

Temperature Sensor Encased in a Conductive Container (e.g., Mushroom Cap and Stem)

Certain embodiments of the inventive subject matter are directed to a temperature sensor assembly wherein the temperature measurement response time is fast, e.g., less than 1 second τ. In one possible embodiment, the assembly includes encasement of a temperature sensor in a highly thermally conductive container that has minimal thermal mass, and where the majority of the surface area of the temperature sensor that is encased is in good thermal contact with the conductive material. A tip portion of the container contacts the surface of a patient's tissue to enable the temperature sensor to measure the surface temperature of the tissue via its good thermal contact with the conductive encasement.

This concept advantageously enables the conductive container and temperature sensor assembly to be thermally isolated from adjacent material having a thermal mass. In this way, cross talk is avoided, the fidelity of the temperature feedback signal is ensured, and a response time of the temperature sensor is reduced.

This concept advantageously enables the portion of the conductive container in contact with the surface of the tissue to be exaggerated such that it has a larger surface area than the surface area of the tip of the temperature sensor.

This concept advantageously enables the portion of the conductive container in contact with the surface of the tissue to be tailored (e.g., smoothed such that what contacts the tissue surface lacks sharp edges) to comfortably contact the patient's tissue surface when the device is moved across the subject's tissue surface (e.g., skin surface).

Capacitive Probe

Certain embodiments of the inventive subject matter are directed to capacitive electrode configurations, where high frequency RF (e.g., 3-30 MHz, or 4 MHz) is emitted, that reduce dielectric losses within a capacitive electrode. The reduced dielectric losses accordingly reduce electrode heating and associated power loss to the electrode, which allows more energy to penetrate into the patient. In one possible embodiment, a metal or otherwise conductive inner probe body has an exterior surface covered with a dielectric coating. The dielectric coating is employed to enable the treatment current to be delivered homogenously over the entire area of the electrode, where the dielectric coated surface of the electrode is in contact with the subject's skin or other target tissue surface.

This concept advantageously enables a larger volume of tissue to be heated at a depth, because power is not lost in the electrode. This can be seen in the slower cool down time of the tissue surface post treatment with the application of high frequency RF (e.g., 3-30 MHz, or 4 MHz) with the capacitive probe.

In some respects, concepts disclosed here generally concern electrosurgical handpieces having a housing for a temperature sensor. The housing defines a first patient-contact surface, an inner surface positioned opposite the first patient-contact surface, and an outer wall extending transversely relative to the first patient-contact surface. A temperature sensor is thermally coupled with the inner surface of the housing. An energizable electrode defines a second patient-contact surface extending outward of the outer wall of the housing. An insulator is positioned between the energizable electrode and the housing for the temperature sensor and inhibits thermal conduction between the energizable electrode and the housing for the temperature sensor. In one embodiment, a shaft can extend proximally from the energizable electrode and define an internal bore extending longitudinally of the shaft. The insulator can extend from a distal end positioned adjacent the first patient-contact surface and the second patient-contact surface to a proximal end positioned within the internal bore. The internal bore can define a first thread and the insulator can define a second thread. The first and second threads can be complementary and matingly engageable with each other.

The electrosurgical handpiece can further have an electrical conductor extending proximally within the handpiece from the temperature sensor.

The first patient-contact surface and the second patient-contact surface can be co-centrically aligned with each other.

The temperature sensor can be one or more of a thermocouple, a resistance-temperature detector, a thermistor, and a diode.

The housing for the temperature sensor can be a material having a thermal conductivity equal to or greater than about 200 W/mK.

The electrode can include a dielectric coating defining the second patient contact surface. The dielectric material can have a dielectric constant of between about 4 to about 12 at an operating frequency of the energizable electrode. The operating frequency of the energizable electrode can be between about 3-30 MHz. The dielectric material coating cam have a substantially even thickness of about 0.004 to about 0.020 inches.

The electrosurgical handpiece can further include a communication component configured to receive a temperature measured by the temperature sensor and to communicate the received temperature to a control system. The electrosurgical handpiece can be coupled to an electrosurgical generator comprising the control system. The control system can be configured to receive a temperature measurement from the temperature sensor via the communication component, compare the received temperature to a threshold temperature, and to modify the output RF waveform in response to the comparison.

The first patient-contact surface can have a larger surface area than a surface area of the temperature sensor that is coupled to the housing.

The energizeable electrode can be capacitively coupled.

The electrosurgical handpiece can be configured to output a radio frequency (RF) waveform received from an electrosurgical generator.

The electrosurgical handpiece can be coupled to an electrosurgical generator that includes a generator configured to combine a first current waveform having a corresponding first frequency, a first amplitude, and a first pulse-width with a second current waveform having a corresponding second frequency, a second amplitude, and a second pulse-width to define a blended waveform output; and a control system configured to control one or more of the first frequency, the first amplitude, the first pulse-width, the second frequency, the second amplitude and the second pulse-width responsive to a temperature received from the temperature sensor; where the energizable electrode is configured to output the blended waveform output received from the electrosurgical generator.

The electrosurgical generator can include a first power source configured to generate the first current waveform; a second power source configured to generate the second current waveform; and a radio-frequency amplifier configured to blend the first and second current waveforms to define a blended waveform and to output the blended waveform to the electrosurgical handpiece.

In other aspects, an electrosurgical handpiece has an energizable electrode comprising a metal foil enclosing a volume and defining a patient-contact surface and a temperature sensor disposed in the volume and thermally coupled with the patient contact surface. The volume can contain a gas or a low thermal mass solid. The low thermal mass solid can including one or more of a solid plastic, and/or a fiber insulation.

In other aspects, an electrosurgical system has a generator configured to combine a first current waveform having a corresponding first frequency, a first amplitude, and a first pulse-width with a second current waveform having a corresponding second frequency, a second amplitude, and a second pulse-width to define a blended waveform output. The electrosurgical system has a control system configured to control one or more of the first frequency, the first amplitude, the first pulse-width, the second frequency, the second amplitude and the second pulse-width responsive to a received temperature.

One or more of the first frequency, the first amplitude, the first pulse-width, the second frequency, the second amplitude and the second pulse-width can be user selectable.

The electrosurgical system can have a handpiece having an energizable electrode to deliver energy corresponding to the blended waveform output to a patient-treatment site. The handpiece can have a temperature sensor configured to output a temperature of the patient-treatment site. The received temperature can correspond to an output from the temperature sensor.

The handpiece can include a temperature sensor and an associated first patient-contact surface. The energizable electrode can define a second patient-contact surface positioned outward of the first patient-contact surface, wherein the second patient-contact surface can be configured to deliver the blended waveform output to a treatment site.

The handpiece can include a housing for the temperature sensor. The housing can define the first patient contact surface positioned relative to the second patient contact surface to observe a temperature of the treatment site. An insulator can be positioned between the energizable electrode and the housing for the temperature sensor to inhibit thermal conduction between the energizable electrode and the housing for the temperature sensor. The first patient contact surface can be positioned relative to the second patient contact surface to observe a temperature of the treatment site.

The electrosurgical system can further have a first adjustable power source configured to generate the first current waveform, a second adjustable power source configured to generate the second current waveform, and a radio-frequency amplifier configured to blend the first and second current waveforms.

The first adjustable power source can be a first adjustable buck and a first power switch. The second adjustable power source can be a second adjustable buck and a second power switch. Each adjustable buck can set an output voltage level for its respective adjustable power source.

The first current waveform can cause the energizeable electrode to deliver energy to cut tissue at a treatment site and the second current waveform can cause the energizeable electrode to deliver energy to coagulate tissue at a treatment site. The blended waveform can cause the energizeable electrode to deliver energy to combine cutting and coagulation at the treatment site.

In still other aspects, an electrosurgical system includes an electrosurgical generator configured to output a radio-frequency (RF) waveform and an electrosurgical handpiece. The electrosurgical handpiece can include a temperature sensor and an associated a first patient-contact surface. The electrosurgical handpiece can also include an energizable electrode defining a second patient-contact surface positioned outward of the first patient-contact surface and configured to output the RF waveform received from the electrosurgical generator.

The electrosurgical generator can further include a control system configured to receive a temperature measurement from the temperature sensor, compare the received temperature to a threshold temperature, and to modify the output waveform in response to the comparison.

The electrosurgical generator can further include a generator configured to combine a first current waveform having a corresponding first frequency, a first amplitude, and a first pulse-width with a second current waveform having a corresponding second frequency, a second amplitude, and a second pulse-width to define a blended waveform output. The electrosurgical generator can also include a control system configured to control one or more of the first frequency, the first amplitude, the first pulse-width, the second frequency, the second amplitude and the second pulse-width responsive to a temperature received from the temperature sensor. The electrosurgical generator can include a first power source configured to generate the first current waveform, a second power source configured to generate the second current waveform, and a radio-frequency amplifier configured to blend the first and second current waveforms to define a blended waveform and to output the blended waveform to the electrosurgical handpiece.

The electrosurgical handpiece can include an insulator positioned between the energizable electrode and the temperature sensor to inhibit thermal conduction between the energizable electrode and the temperature sensor.

In other aspects, a method of treatment includes placing an electrosurgical handpiece in contact with a treatment surface, causing the electrosurgical handpiece to emit a radio-frequency (RF) signal for a selected duration, and wherein the treatment surface is heated in correspondence with the RF signal and the selected duration. The method can include measuring, with the electrosurgical handpiece, a temperature of the treatment surface, communicating the measured temperature to a control system, and receiving, from the control system, a control signal responsive to the measured temperature.

The method can further include moving the electrosurgical handpiece over the treatment surface to contact different regions of the treatment surface, and in some cases, moving the electrosurgical handpiece over the treatment surface continuously for the selected duration.

In some embodiments, the method includes applying a topical solution (e.g., ultrasound gel) to the treatment surface before placing the electrosurgical handpiece in contact with the treatment surface.

The surface treated by the method can, for example, be human skin. One or more of a dermal layer, an epidermal layer, or a deep tissue layer or human skin is heated in accordance with the method.

The treatment surface can be heated to a range of about 39 C-46 C. The treatment time period can be between about 5 minutes to about 50 minutes.

In some cases, the control signal received from the control system can cause a termination of the RF signal.

In other cases, the control signal received from the control system can cause a re-engagement of the RF signal.

The method can further include causing the electrosurgical handpiece to emit a sinusoidal RF energy.

In still other aspects, a method includes causing an electrosurgical handpiece to emit a radio-frequency (RF) signal for a selected duration, receiving from the electrosurgical handpiece a temperature of a treatment surface in contact with the electrosurgical handpiece, comparing the received temperature to a threshold temperature, terminating the RF signal when the received temperature is equal to or higher than the threshold temperature, and re-engaging or continuing the RF signal emission when the received temperature is lower than the threshold temperature.

The method can further include receiving a user selection of a value for one or more of a first frequency, a first amplitude, a first pulse-width, a second frequency, a second amplitude, and a second pulse-width and causing the electrosurgical handpiece to emit a RF signal comprising a waveform blended from a first current waveform having the first frequency, the first amplitude, and the first pulse-width and a second current waveform having the second frequency, the second amplitude, and the second pulse-width.

In still other aspects, a method includes placing an electrosurgical handpiece in contact with a treatment surface, receiving a user selection of a value for one or more of a first frequency, a first amplitude, a first pulse-width, a second frequency, a second amplitude, and a second pulse-width, and causing the electrosurgical handpiece to emit a radio-frequency (RF) signal including a waveform blended from a first current waveform having the first frequency, the first amplitude, and the first pulse-width and a second current waveform having the second frequency, the second amplitude, and the second pulse-width.

In the method, the first current waveform can be configured to cause the electrosurgical handpiece to cut the treatment surface and the second current waveform can be configured to cause the electrosurgical handpiece to coagulate the treatment surface.

In the method, the blended waveform can be configured to cause the electrosurgical handpiece to combine cutting and coagulation on the treatment surface.

The method can further include receiving, at the electrosurgical handpiece, the blended waveform from an electrosurgical generator.

The method can further include measuring a temperature of the treatment surface with the electrosurgical handpiece and controlling one or more of the first frequency, the first amplitude, the first pulse-width, the second frequency, the second amplitude, and the second pulse-width responsive to the measured temperature.

The foregoing and other features and advantages will become more apparent from the following detailed description of disclosed embodiments, which proceeds with reference to the accompanying drawings.

BRIEF DESCRIPTION OF THE DRAWINGS

Unless specified otherwise, the accompanying drawings illustrate aspects of the innovations described herein. Referring to the drawings, wherein like numerals refer to like parts throughout the several views and this specification, several embodiments of presently disclosed principles are illustrated by way of example, and not by way of limitation. The drawings are not intended to be to scale.

DETAILED DESCRIPTION

The following describes various principles related to innovative electrosurgical systems, and components thereof, by way of reference to specific examples of electrosurgical systems, components and methods, including configurations for energizable electrodes, temperature sensors, electrosurgical generators, and associated controllers, as well as power and temperature control components and related methods. In some innovative embodiments, a handpiece can constitute an electrosurgical instrument or device having an energizable electrode configured to treat or otherwise manipulate a target site on or in a patient's body, as well as associated power and temperature components. Accordingly, the inventive subject matter may be directed to overall systems, isolated components, alone or in various combinations.

Overview

Figure 34:
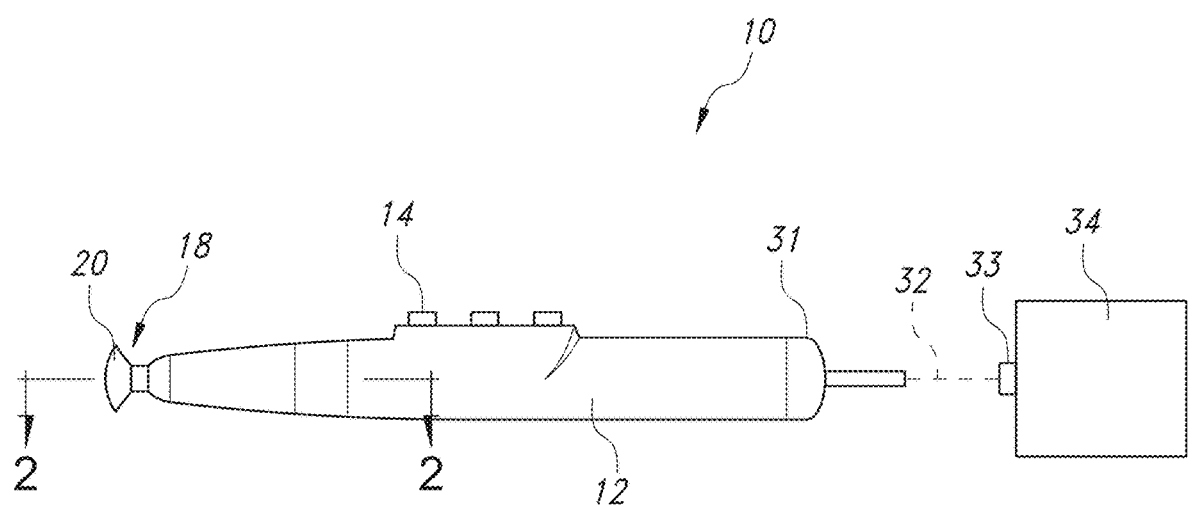
FIG. 34 schematically illustrates an electrosurgical handpiece.

U.S. Pat. No. 9,345,531 and U.S. Publication No. 2013/0006239, the disclosures of which are hereby incorporated herein, for all purposes, disclose electrosurgical handpieces similar to that shown in FIG. 34. During use of such an electrosurgical handpiece, a medical practitioner or other operator can apply an electrosurgical therapy to a treatment site by sweeping an energizable electrode across a region of a patient's skin along a generally circular, trochoidal, or other selected path.

Some electrosurgical devices and systems disclosed herein are configured for, and some disclosed methods provide, non-ablative electrosurgery therapies. Some disclosed electrosurgical devices and systems are configured to, and some disclosed methods can, prevent traumatic disruption to a tissue, as well as to keep any tissue disruption below a patient's pain threshold. Some disclosed electrosurgical systems, devices, and related techniques can provide ablative and/or non-ablative therapies to human tissue.

For example, some disclosed electrosurgical devices are configured to deliver energy to a patient's skin without the need for anesthetizing the patient. Although difficult to quantify the precise limits of such power thresholds, applying an energy flux of 4,000 Watts per square centimeter (W/cm$^2$) for about one second (1 s) probably would not ablate skin tissue, but might cause necrosis of some tissue. On the other hand, it is presently believed that an energy flux of about 2,000 W/cm$^2$ applied for between about 2 seconds (s) and about 3 s (e.g., between about 1.9 s and about 3.1 s, such as, for example, between about 2.1 s and about 2.9 s) can be applied to skin tissue to obtain desirable clinical outcomes. Lower flux levels can be applied for longer times, and higher flux levels might be applied for shorter times, without damaging tissues.

RF Generator System-Surgical Applications

A radio frequency (RF) generator system can include a circuit topology to provide a variety of output waveforms suitable for use in electro-surgical therapies. The output waveforms can arise from a combination of a plurality, e.g., two, constituent waveforms. In turn, one or more parameters of each constituent waveform can be user selectable or controllable. For example, an RF generator can operate on a fundamental frequency of about 4 MHz, or from about 400 kHz to about 13.56 MHz, or from about 500 kHz to about 8 MHz, or from about 3 MHz to about 5 MHz. An RF generator system disclosed herein typically can operate on a fundamental frequency of about 4 MHz.

Output waveforms produced by a monopolar output can include, for example, a continuous output and a variety of pulsed waveforms with, for example, the fundamental frequency of about 4 MHz. One or more of an amplitude, frequency, duty-cycle and pulse width of the output waveform can be user controllable or selectable, and can arise from a combination of constituent waveforms.

A continuous sine wave output produces a cutting tissue effect with little or minimized heating coagulation effect to the tissue adjacent the cut. A pulsed waveform with, for example, the fundamental frequency of about 4 MHz output produces a coagulation effect.

Figure 1:
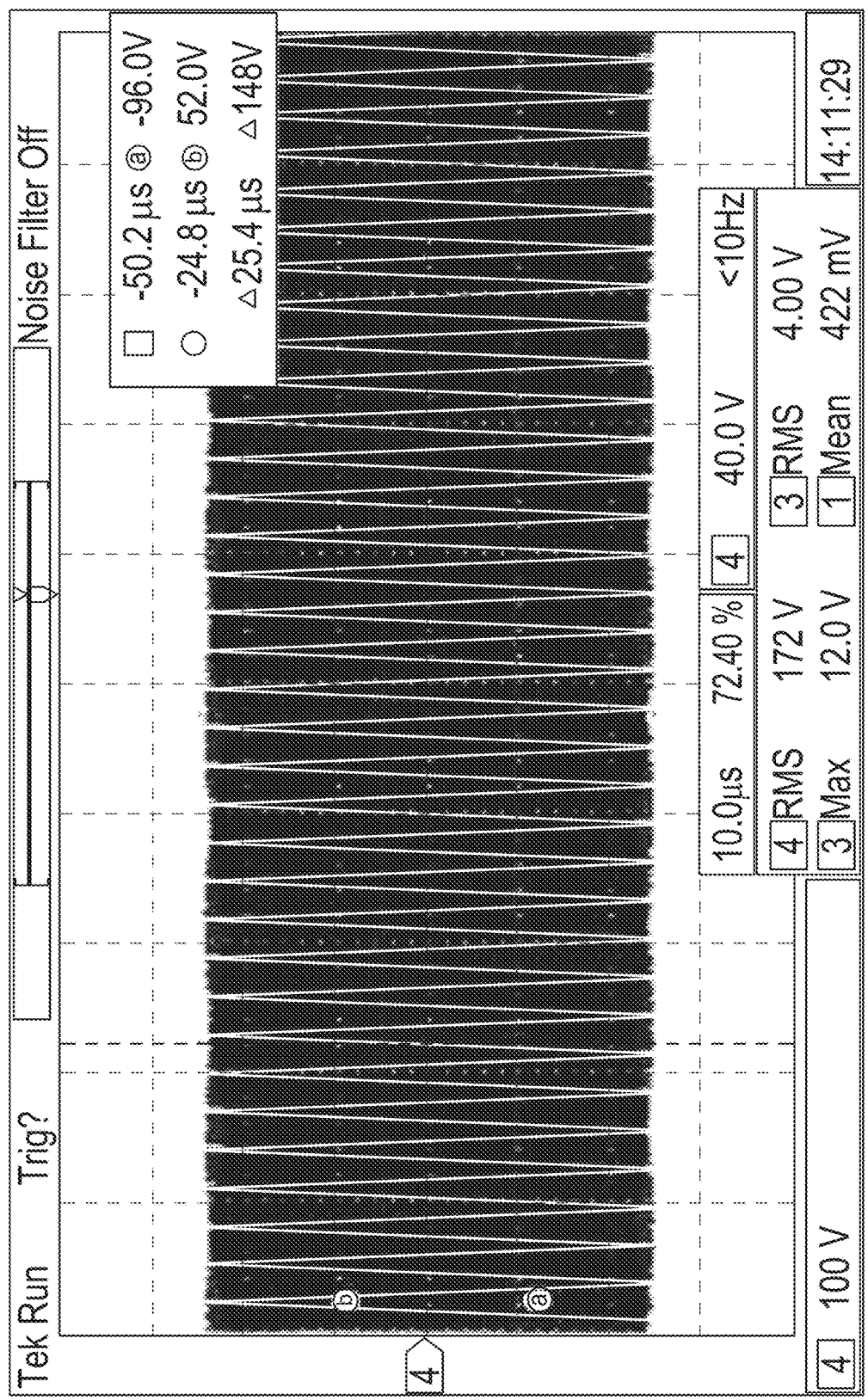
FIGS. 1 through 5 show examples of waveforms corresponding to different treatment modes available from an exemplary RF generator system.

Although a measure of average power applied to a treatment site, for example, may be approximately the same for different waveforms, the therapeutic effect corresponding to one waveform may substantially differ from the therapeutic effect corresponding to another waveform. FIGS. 1 through 5 show different waveforms that may correspond to different treatment modes available from an exemplary RF generator system. These different treatment modes may result in various tissue treatment effects and may be categorized, for example, as:

Cut only (CONTINUOUS WAVEFORM) shown in FIG. 1.

Figure 2:
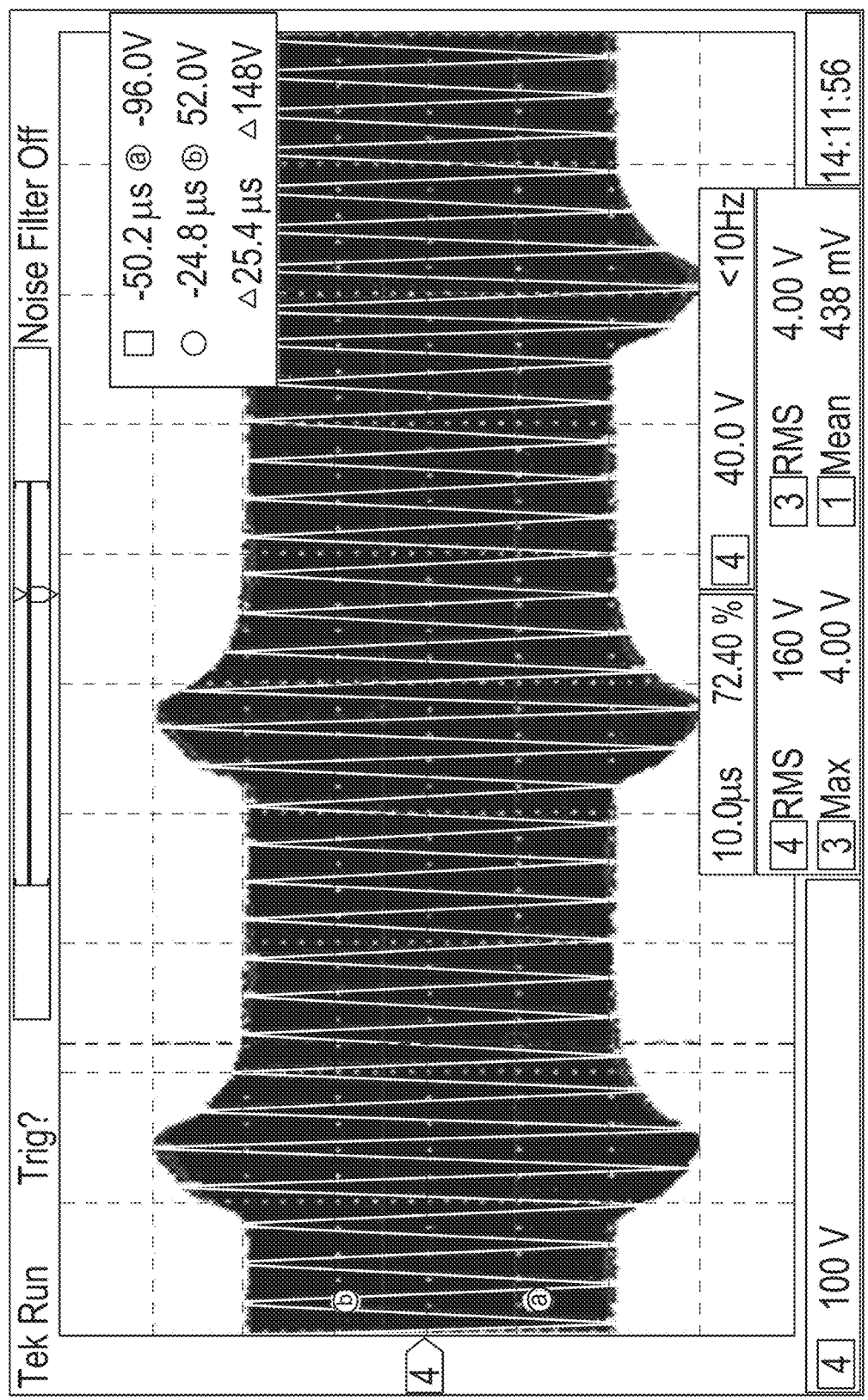

Lots of cut with little coagulation (CONTINUOUS WAVEFORM) shown in FIG. 2.

Figure 3:
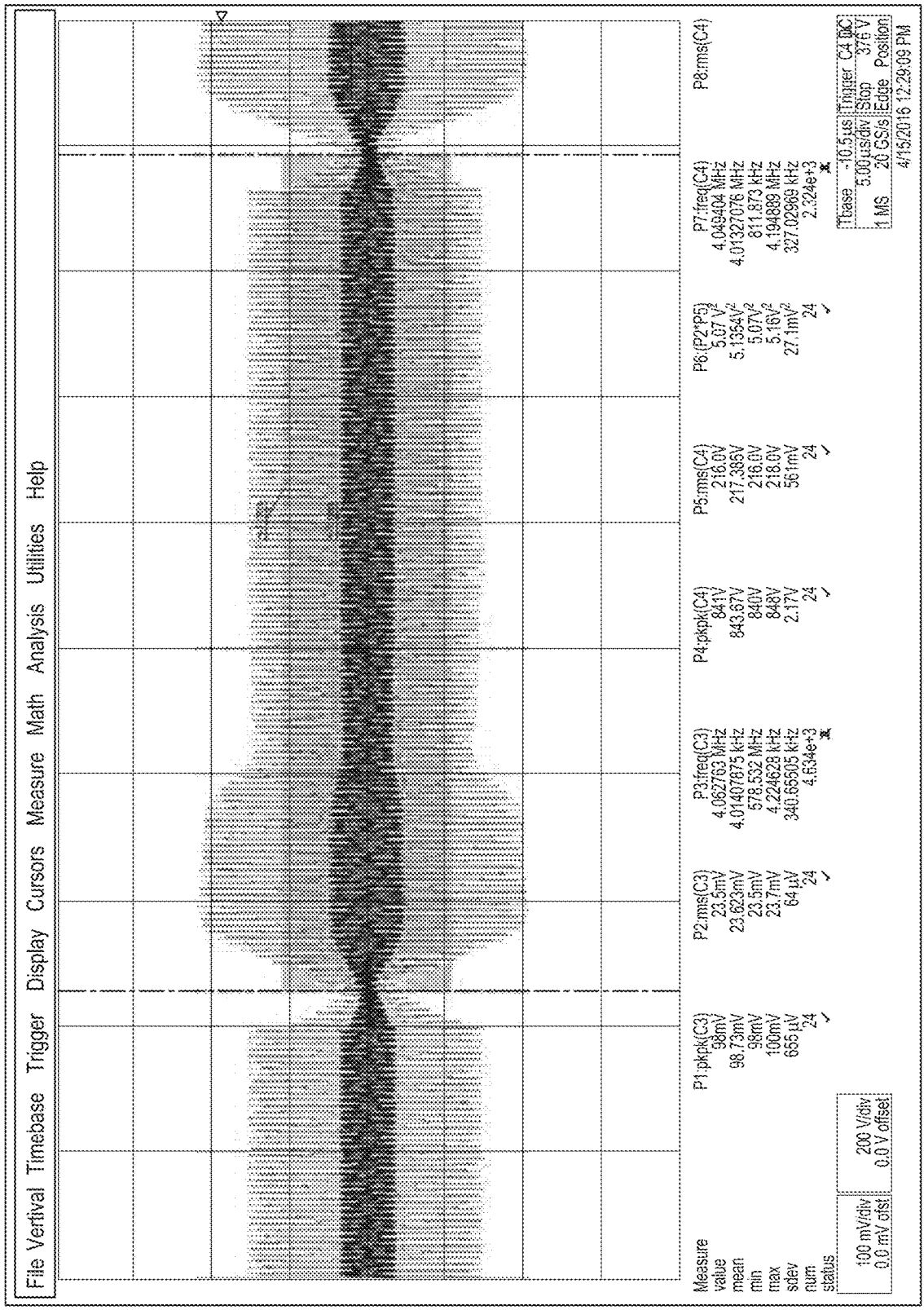

Moderate cut with moderate coagulation (DISCONTINUOUS WAVEFORM) shown in FIG. 3.

Figure 4:
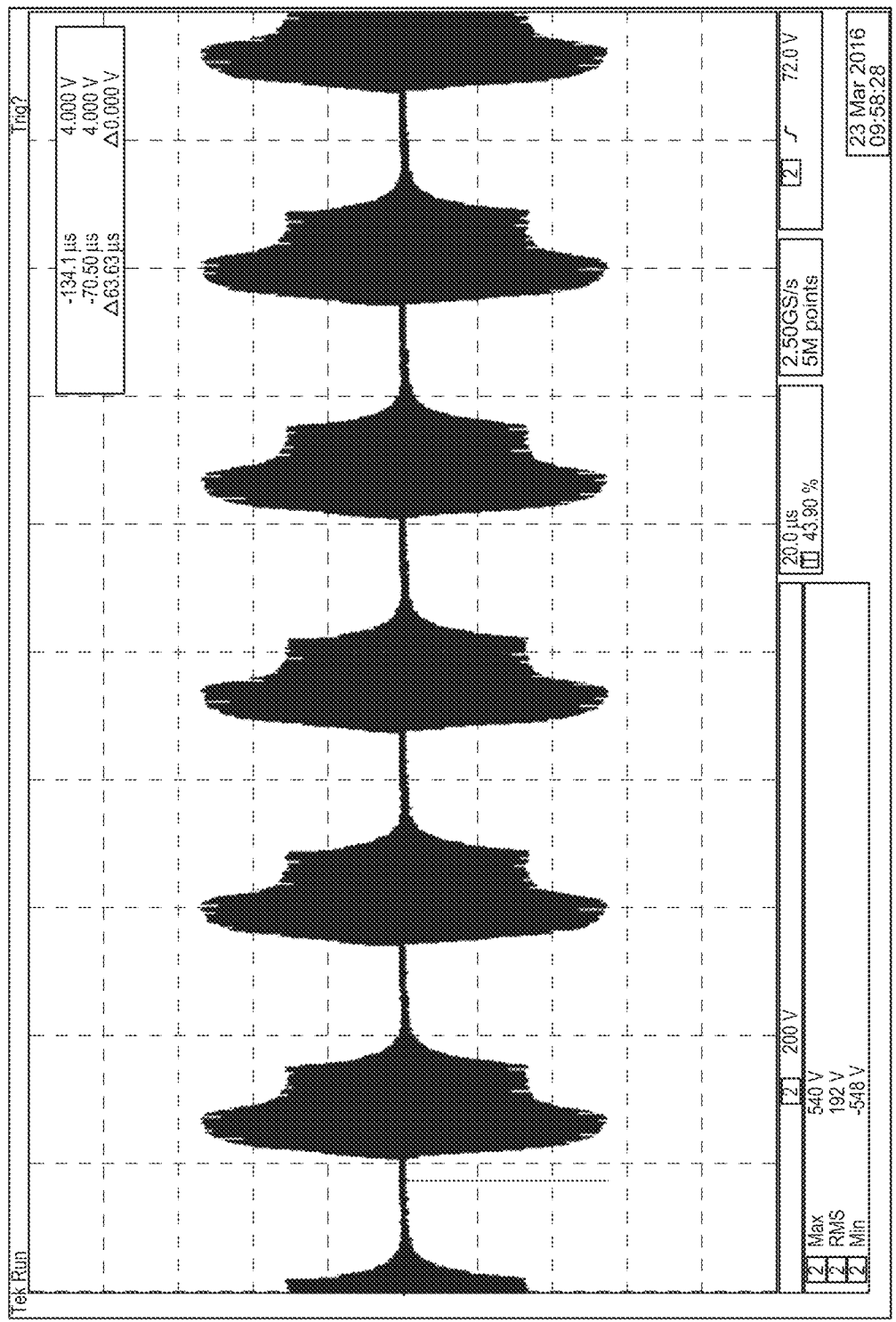

Lots of coagulation with little cut (DISCONTINUOUS WAVEFORM) shown in FIG. 4.

Figure 5:
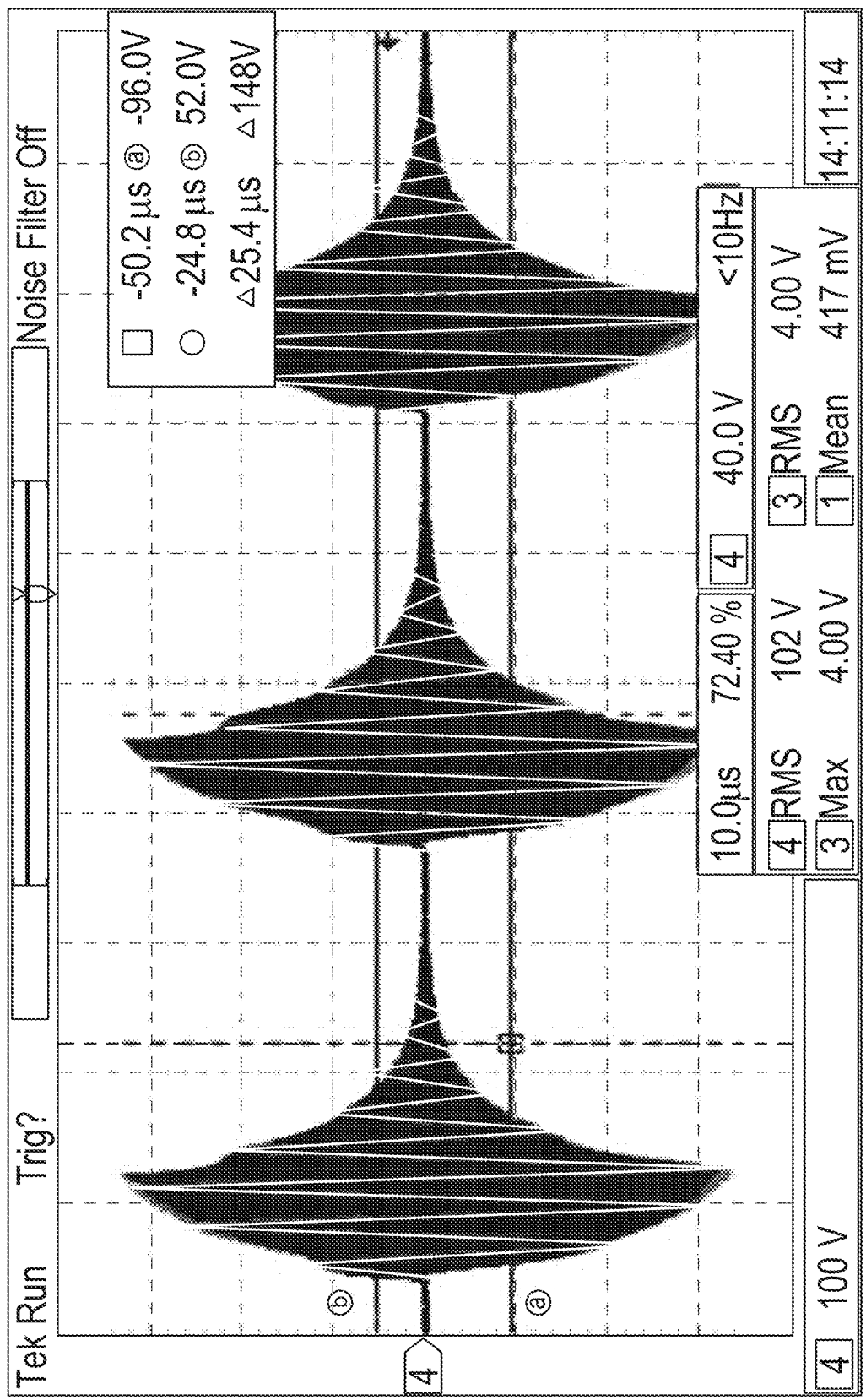

Coagulation only (DISCONTINUOUS WAVEFORM) shown in FIG. 5.

Figure 6:
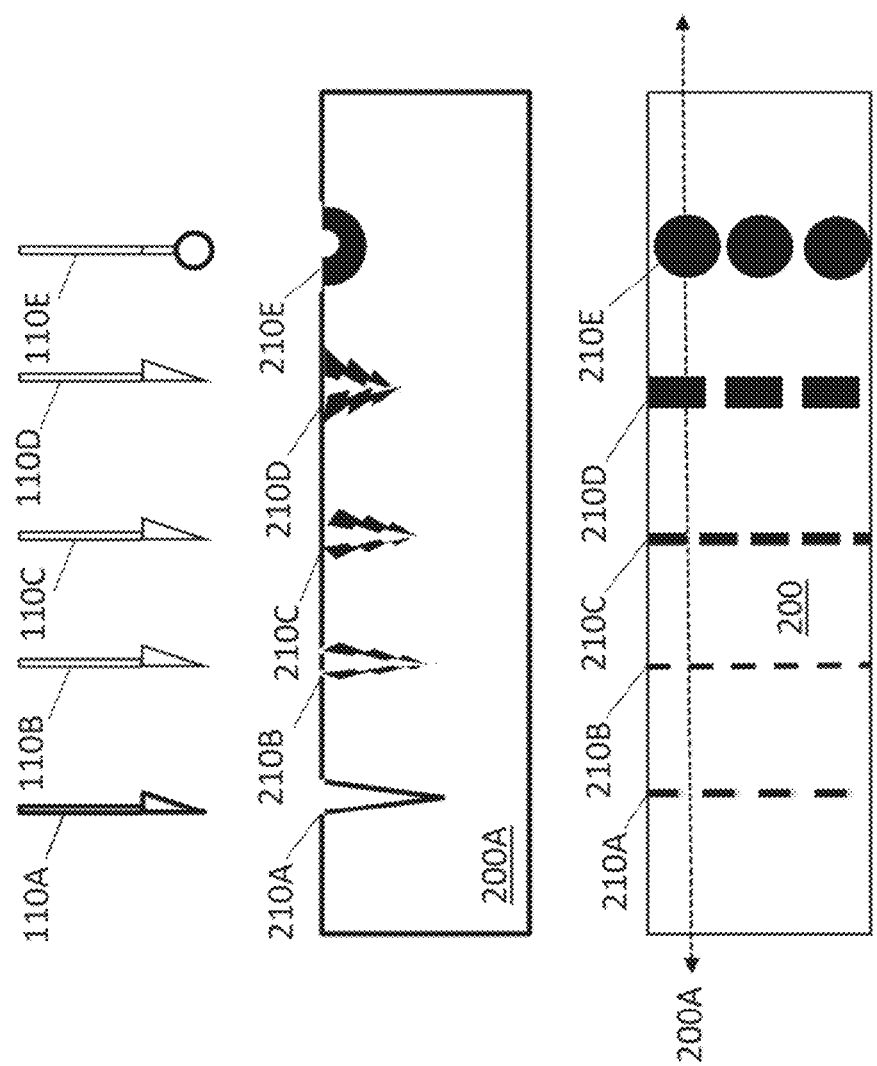
FIG. 6 schematically illustrates several RF-treatment implements and corresponding examples of therapeutic effects of each on a treatment site.

FIG. 6 shows examples of various RF treatment implements including an RF powered scalpel (110A-110D) and an RF powered ball (110E). FIG. 6 shows the surface of skin tissue 200 that was treated with RF powered treatment implements 110A-110E and also shows a cross section of tissue 200A after treatment with the RF powered treatment implements 110A-110E.

More specifically, referring still to FIG. 6, the continuous sine wave output as is shown in FIG. 1 cuts tissue 200 with little coagulation effect to tissue adjacent to the cut. The tissue effect of the continuous sine wave output shown in FIG. 1 with scalpel 110A is shown in the treatment region labeled 210A. The cross section of the tissue 200A about the tissue 210A that was cut by scalpel 110A shows that the cut is clean with a small amount of coagulation that results from RF energy applied to cut the tissue.

More specifically, referring still to FIG. 6, and in contrast, the solely pulsed output shown in FIG. 5 is designed to give a coagulation tissue effect and to not produce continuous plasma for cutting. The RF powered ball 110E is repeatedly pressed on the surface of the tissue 200 and coagulates the tissue in contact with the RF powered ball 110E with each press of the RF powered ball 110E on the tissue surface. The tissue effect of the pulsed output shown in FIG. 5 with ball 110E is shown in the treatment region labeled 210E. The cross section of the tissue 200A about the tissue 210E that was treated by ball 110E shows that the ball made an impression of coagulation in the tissue 200 surface and as seen in the cross section 200A.

According to certain embodiments, by combining the continuous sine waveform of cutting with the pulsed waveform of coagulation, the combination of the two waveforms enable a combined cut and coagulation tissue effect to be produced. Such a combination of continuous sine waveform and the pulsed waveform is referred to as the blend mode, because the cut and coagulation tissue effects are "blended." FIGS. 2 to 4 show three such blend mode waveforms. FIG. 2 depicts a continuous waveform with lots of cut and little coagulation. FIG. 3 depicts a discontinuous waveform with a middle amount of cut and a middle amount of coagulation. FIG. 4 depicts a discontinuous waveform with a lot of coagulation and small amount of cut. The unique circuit design of the disclosed RF generator system allows for a variety of output waveforms to be produced.

Exemplary blend waveforms are shown in association with FIGS. 2-4. For example, FIG. 2 provides a waveform that produces a continuous cutting effect with increased side heating, which generates a hemostasis effect on the sides of the incision. Other waveforms can be produced giving more or less hemostasis and more or less of an aggressive cutting effect, as shown in FIGS. 2-4.

Referring again to FIG. 6 a blended effect is achieved with the continuous waveform shown in FIG. 2, which has lots of cut and little coagulation, and which cuts tissue 200 with a small amount of coagulation effect to the tissue adjacent the cut. The tissue effect of the continuous waveform shown in FIG. 2 with scalpel 110B is shown in the treatment region labeled 210B. The cross section of the tissue 200A about the tissue region 210B that was cut by scalpel 110B shows that the cut has a small amount of coagulation.

Referring still to FIG. 6, a blended effect is also achieved with the discontinuous waveform shown in FIG. 3, which has a middle amount of cut and a middle amount of coagulation, and which cuts tissue 200 with a middle amount of coagulation effect to the tissue adjacent the cut. The tissue effect of the discontinuous waveform shown in FIG. 3 with scalpel 110C is shown in the treatment region labeled 210C. The cross section of the tissue 200A about the tissue region 210C that was cut by scalpel 110C shows that the cut has a middle amount of coagulation.

FIG. 6 shows another blended effect that is achieved with the discontinuous waveform shown in FIG. 4, which has a lot of coagulation and small amount of cut, and which cuts tissue 200 with a small amount of cut and a lot of coagulation effect on the tissue adjacent to the cut. The tissue effect of the discontinuous waveform shown in FIG. 4 with scalpel 110D is shown in the treatment region labeled 210D. The cross section of the tissue 200A about the tissue region 210D that was cut by scalpel 110D shows that the cut has a large amount of coagulation. In some embodiments, the amount of coagulation in region 210D is comparable to the coagulation effect in the tissue region 210E that was treated by a pulsed output shown in FIG. 5.

Figure 7:
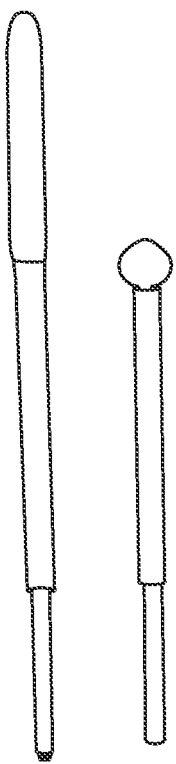
FIG. 7 shows working embodiments of two handpieces having RF-treatment electrodes.

FIG. 7 shows an image of a scalpel electrode on the left (e.g., a scalpel electrode having a shaft diameter of ¹⁄₁₆") and a ball electrode on the right (e.g., a 5 mm ball with a ¹⁄₁₆" shaft diameter) that were each used to cut a pork cutlet measuring ⁷⁄₁₆ inches thick (e.g., 11 mm thick) and discussed in association with FIGS. 8-12.

Figure 8:
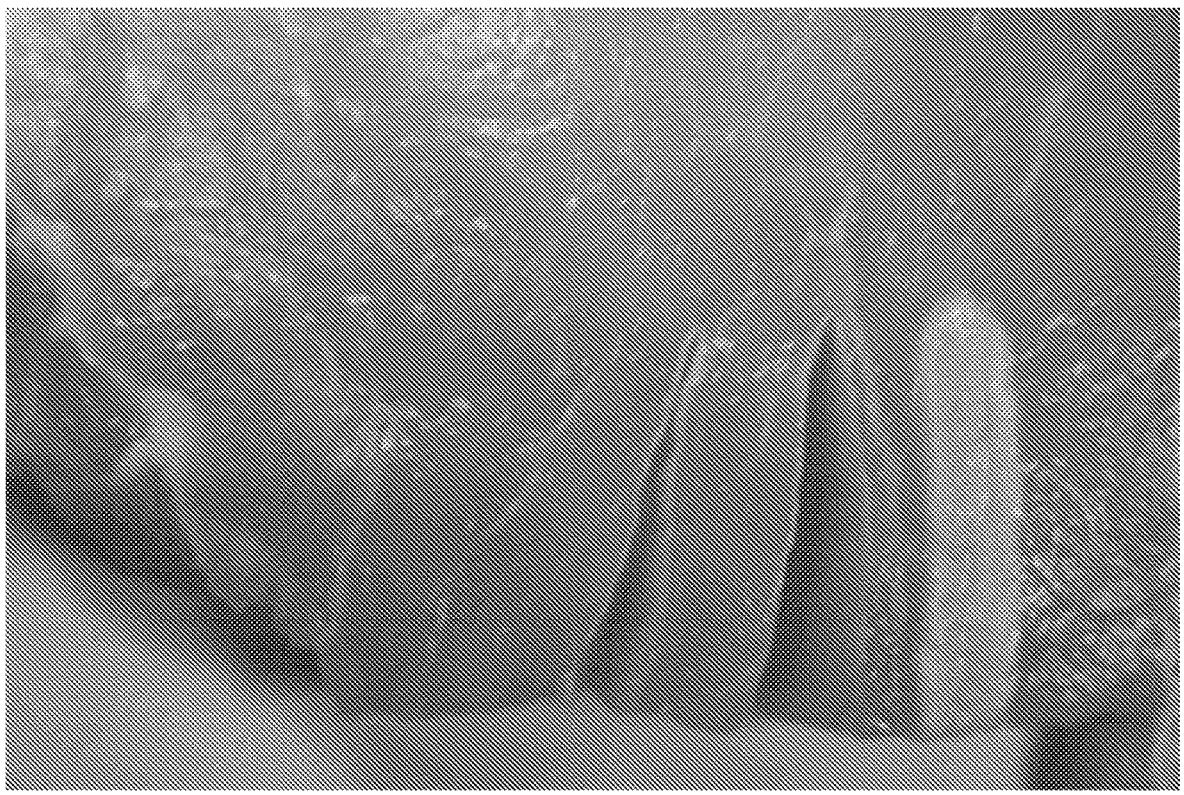
FIGS. 8-12 show surface and cross-section views of pork cutlet tissue treated with different waveforms to demonstrate corresponding therapeutic effects of the different waveforms.
Figure 10:
Figure 9:
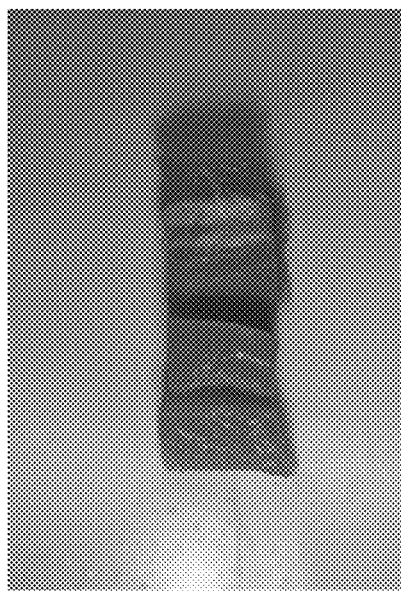

FIG. 8 shows a surface view pork cutlet tissue that was treated on the left in cut mode with a scalpel electrode using a waveform similar to that shown in association with FIG. 1 at a device output of 20 (on a scale from 0-100), in the center in cut mode with a scalpel electrode using a waveform similar to that shown in association with FIG. 1 at a device output of 60 (on a scale from 0-100), and on the right in coagulation mode with a ball electrode using a waveform similar to that shown in association with FIG. 5 at a device coagulation output of 100 (on a scale from 0-100). FIG. 9 shows another view of the pork cutlet tissue described in association with FIG. 8. This top view shows the three areas where the tissue was treated in cut mode on the left side, in cut mode in the middle, and in coagulation mode on the right side and enables a different view of the cuts. FIG. 10 shows a view of the cross section of the pork cutlet tissue described in association with FIG. 8, this cross-sectional view shows the depth of the tissue treated in cut mode on the left side, in cut mode in the middle, and in coagulation mode on the right-hand side.

Figure 11:
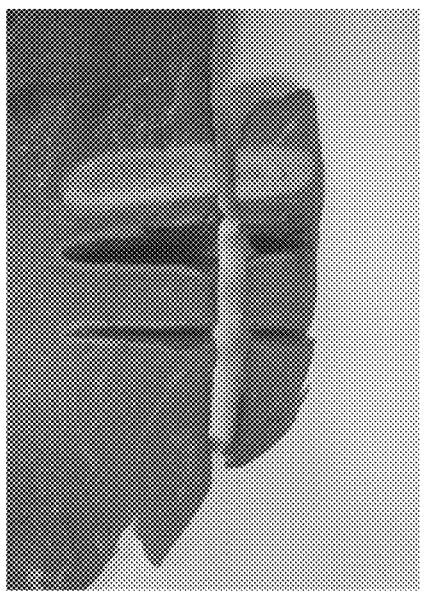

FIG. 11 shows a surface view (above) and a top view (below) of pork cutlet tissue that was treated: on the left in cut mode with a scalpel electrode using a waveform similar to that shown in association with FIG. 1 at a device output of 20 (on a scale from 0-100), in the center in blend mode with a scalpel electrode using a waveform similar to that shown in association with FIG. 3 at a device output of 60 (on a scale from 0-100), and on the right in coagulation mode with a ball electrode using a waveform similar to that shown in association with FIG. 5 at a device coagulation output of 100 (on a scale from 0-100).

Figure 12:
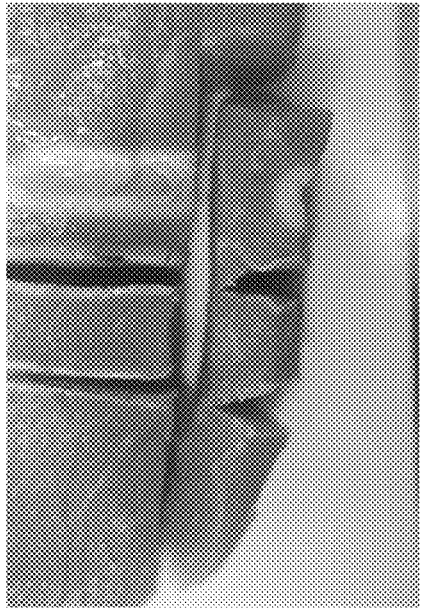

FIG. 12 shows a surface view (above) and a cross sectional view (below) of pork cutlet tissue that was treated: on the left in cut mode with a scalpel electrode using a waveform similar to that shown in association with FIG. 1 at a device output of 20 (on a scale from 0-100), in the center in blend mode with a scalpel electrode using a waveform similar to that shown in association with FIG. 3 at a device output of 60 (on a scale from 0-100), and on the right in coagulation mode with a ball electrode using a waveform similar to that shown in association with FIG. 5 at a device coagulation output of 100 (on a scale from 0-100). Referring still to FIG. 12, the cross-sectional view shows the depth of the tissue treated in cut mode on the left side, in blend mode in the middle, and in coagulation mode on the right-hand side.

Figure 13:
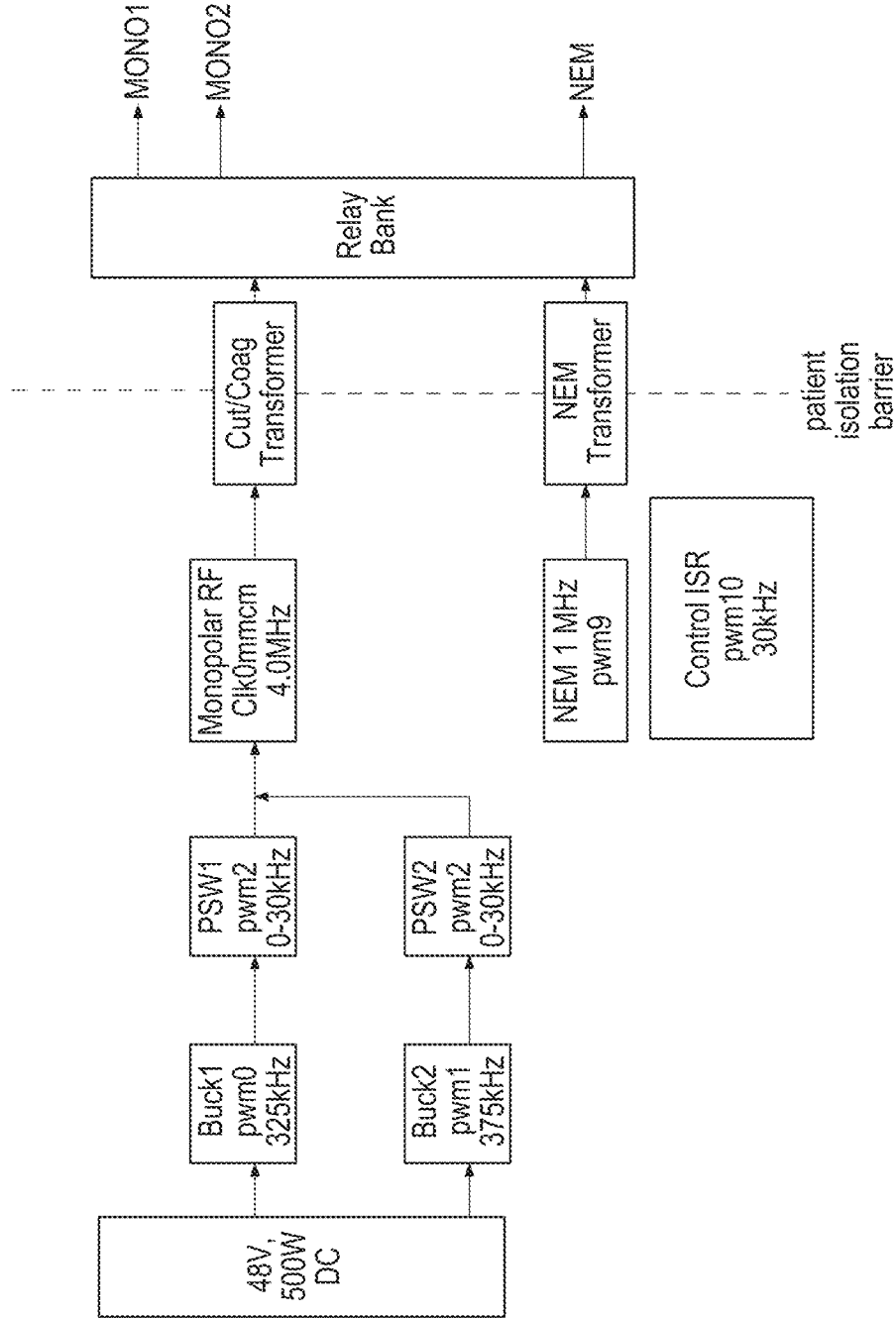
FIG. 13 schematically illustrates a circuit topology for a power switch that can produce a variety of blend output waveforms.
Figure 14:
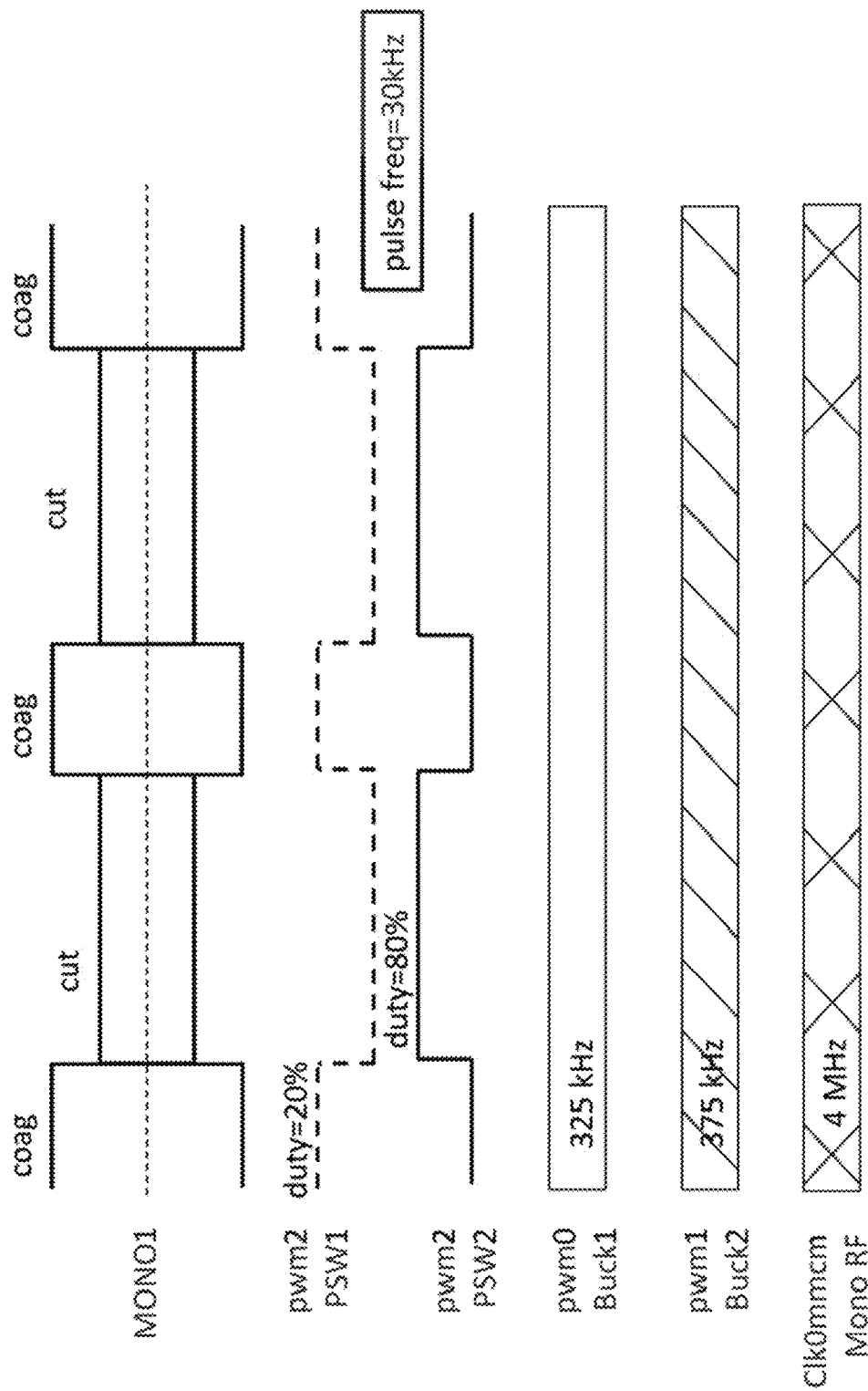
FIG. 14 schematically illustrates a "two-tiered," blended waveform output.

Implementation of the above-disclosed blended output waveform can be accomplished via a circuit design as follows. FIG. 13 shows one embodiment of power switch circuit topology that allows the above described variety of blend output waveforms to be produced. According to certain embodiments, the circuit may have two independently controllable DC circuits along with one monopolar RF circuit running at the fundamental frequency of about 4 MHz. The monopolar RF circuit continues to run at 4 MHz and two independent DC bucks are provided that controllably lessen the DC voltage that is supplied to two independent Power Switches (PSW). The two Power Switches are switched/connected to the output independently at a rate of approximately 30 kHz. This creates the "two-tiered" output waveform as shown in FIG. 14. The output voltages of the cut portion of the blend waveform and the coagulation portion of the blend waveform can be independently adjusted, with the choice and/or pattern of adjustment giving different tissue effects.

Figure 15:
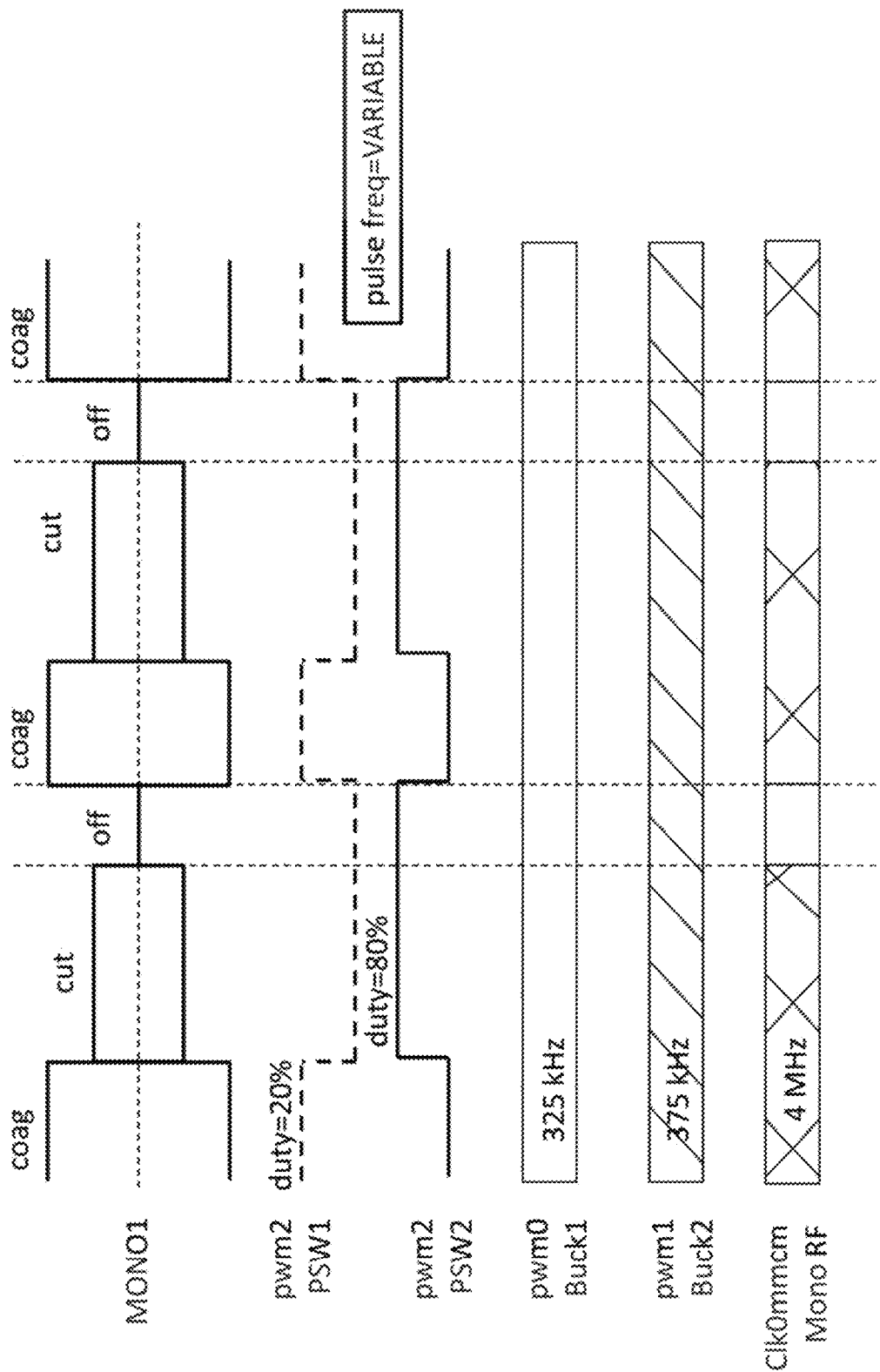
FIG. 15 schematically illustrates another "two-tiered," blended waveform output.

In addition, referring now to FIG. 15, the power switch circuit can be operated such that a dead time (e.g., off interval) between 30 kHz cycles may be selected. The dead time is present after the cut and prior to the next cycle coagulation. This dead time or off period duration can be adjusted to ensure the plasma from the previous "cut" period has time to fully extinguish before initiating the next cycle. This way, no undesired cutting between cycles occurs, and tissue only coagulates during the coagulation portion of the cycle.

Figure 16:
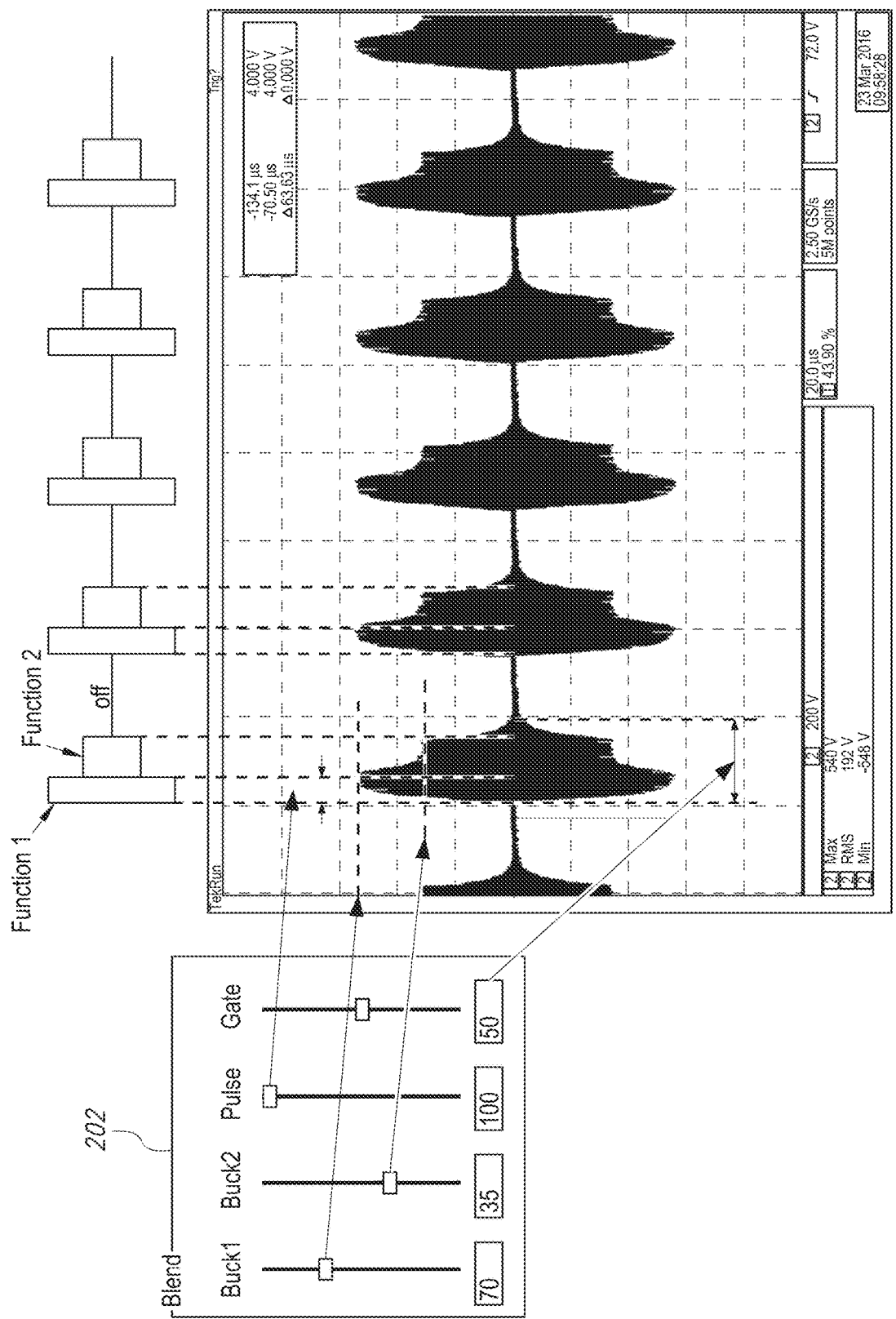
FIGS. 16 and 17 show additional examples of output blended waveforms according to embodiments.
Figure 17:
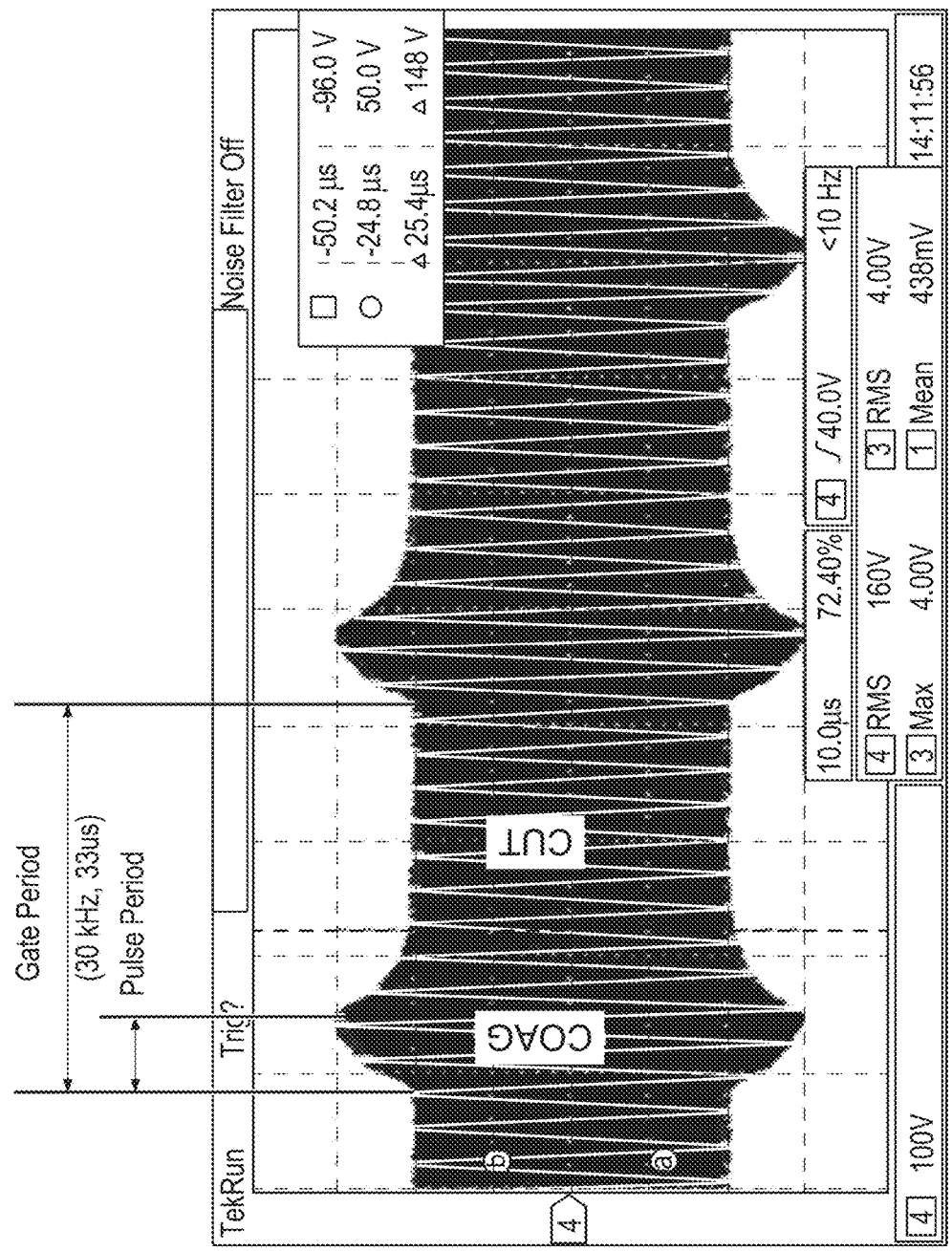

Referring now to an example shown in FIGS. 16 and 17, according to certain embodiments, the blend waveform is pulsed at 30 kHz (33 µs). Buck 1 sets the voltage level of a first function, e.g., a coagulation portion, of the output, and Buck 2 sets the voltage level of a second function, e.g., a cut portion, of the output. Here, as seen in a user interface element 202 that allows a user to adjust various aspects of the blend waveform, Buck 1 may be set at a higher voltage than Buck 2. Specifically, in FIG. 16, Buck 1 is set at 70 percent of its maximum voltage and Buck 2 is set at 35 percent of its maximum voltage, which is 50% of the voltage of Buck 1. The Pulse sets the duration of the coagulation portion for the output for one 30 kHz pulse, here the pulse is set at 100 percent. The Gate sets the overall duration of the output waveform for each 30 kHz pulse. For example, if the Gate is set to 100 then the composite pulse is on for the entire 30 kHz period (33 µs). If, as is shown in FIGS. 16 and 17, the Gate is set at 50 percent, then the composite pulse of the RF emission will have a duration of 50 percent of the period (16.5 µs). And here, because the Pulse is set at 100, the output pulse will be on for the entire 16.5 µs that the RF emission is on. Accordingly, by adjustably controlling the foregoing parameters, desired blended waveform profiles may be achieved.

In various embodiments, one or more of a waveform's frequency, amplitude, and pulse-width may be user-selectable, for example, via a user interface element 202 displayed by a software control application, or by physical switches or controls on an electrosurgical generator.

To illustrate, referring again to the pork cutlet tissue treated and disclosed in association with FIGS. 8-10, and the setting options disclosed in FIG. 16, the cut on the left side is accomplished by setting Buck 1 at 20 and there is no setting of Buck 2, Pulse, or Gate, because these are not applicable in Cut mode. The cut in the middle is accomplished by setting Buck 1 at 60 and there is no setting for Buck 2, Pulse, or Gate, because these are not applicable in Cut mode. The coagulation on the right-hand side is accomplished by setting Buck 1 at 100 and the Pulse at 100, there is no setting for Buck 2 or Gate, because these are not applicable in coagulation mode.

Referring again to the pork cutlet tissue treated and disclosed in association with FIGS. 11-12 and the setting options disclosed in FIG. 16, the cut on the left side is accomplished by setting Buck 1 at 20 and there is no setting of Buck 2, Pulse, or Gate, because these are not applicable in Cut mode. The blend of cut and coagulation in the middle is accomplished by setting Buck 1 at 60, Buck 2 at 54, Pulse at 100, or Gate at 100. The coagulation on the right-hand side is accomplished by setting Buck 1 at 100 and the Pulse at 100, there is no setting for Buck 2 or Gate, because these are not applicable in coagulation mode.

RF Generator System-Non-Invasive Aesthetic Treatments

According to certain embodiments, the RF generator system may include an improved response time temperature sensor that is well-suited for use in non-invasive aesthetic treatments employing an RF generator system. The improved response time temperature sensor responds more quickly than other temperature sensors and includes a temperature sensor/electrode assembly.

In an exemplary embodiment, the RF generator system provides RF energy (e.g., 4 MHz sinusoidal RF energy) that is applied to the tissue surface of a treatment subject (e.g., a patient) to cause heating of the subject's dermal, epidermal and/or deeper tissue layers. In one possible embodiment, a topical solution, such as gel (e.g., ultrasound gel), lotion, or another substance may be applied to the surface of the subject's tissue (e.g., skin) prior to non-invasive RF energy treatment in order to reduce friction between the electrode and the surface, and/or to improve thermal or electrical conductivity from the patient-contact surface to the tissue surface of the treatment site. The RF electrode is placed on a tissue surface (e.g., skin surface) of the treatment subject to which the topical solution has already been applied. The RF generator initiates an RF emission from an electrosurgical handpiece, and more particularly from the energizable electrode contacting the treatment site. The clinician moves the electrode tip of the electrosurgical handpiece in contact with the subject's tissue surface over a treatment area of the subject's tissue surface (e.g., skin surface). In some embodiments, the clinician moves the electrode tip over the subject's tissue surface continuously and without pausing or stopping. This treatment results in an area of elevated temperature, preferably a substantially uniform area of elevated temperature, with an elevated temperature that preferably measures around 42 C+/−1 C which is maintained for a given treatment time of from about 5 minutes to about 25 minutes, such as, for example, from about 7 minutes to about 10 minutes. The RF generator can achieve an elevated temperature range of from about 39 C to about 46 C, as from about 41 C to about 44 C. The temperature elevation that is targeted may vary from patient to patient depending on the size of the treatment area, the sensitivity of the treatment area, and the tolerance of the patient amongst other factors. Likewise, the selected duration of the treatment time may vary depending on the size of the treatment area, the targeted depth of the treatment area, etc. Depending on such factors, suitable treatment times may range from about 5 minutes to about 50 minutes, or about 30 minutes.

To achieve a substantially uniform temperature rise and/or a substantially homogeneous temperature rise throughout the treatment area with a continuously moving electrode, an improved response time temperature feedback sensor is required. The disclosed embodiments advantageously provide such an improved sensor. Preferably, the improved response time temperature feedback sensor has a response time constant of about 1 second or less.

Figure 18A:
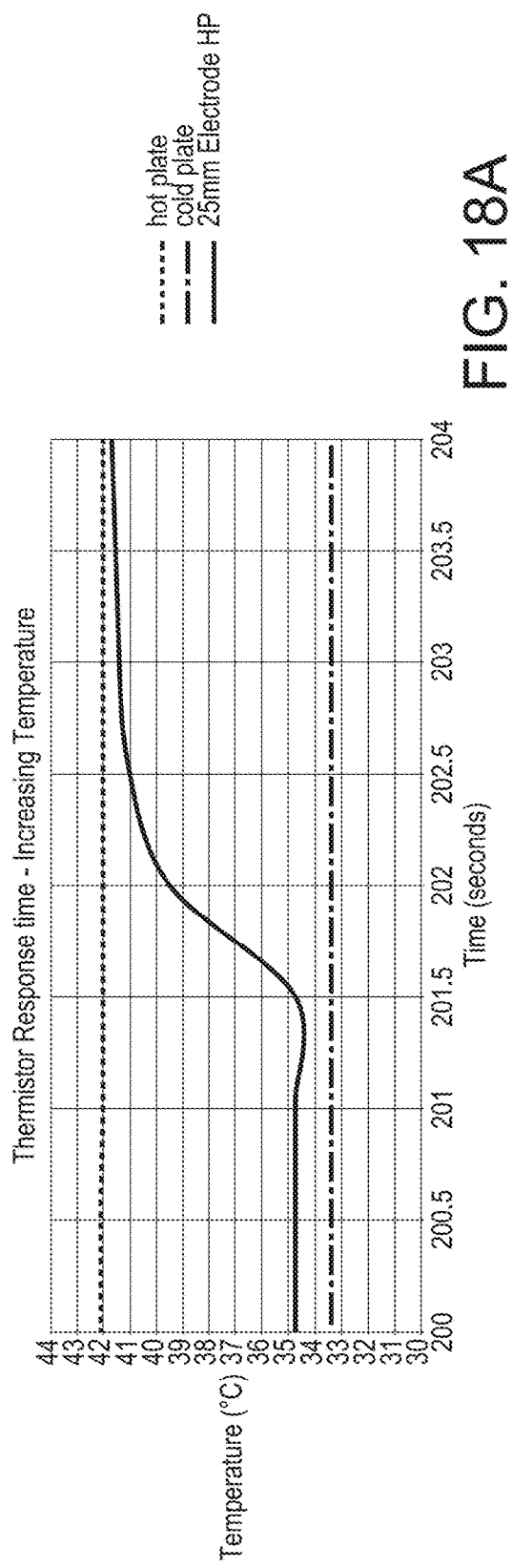
FIGS. 18A and 18B illustrate transient temperature responses of a thermistor assembly to a step-increase in power and a step decrease in power, respectively.
Figure 18B:
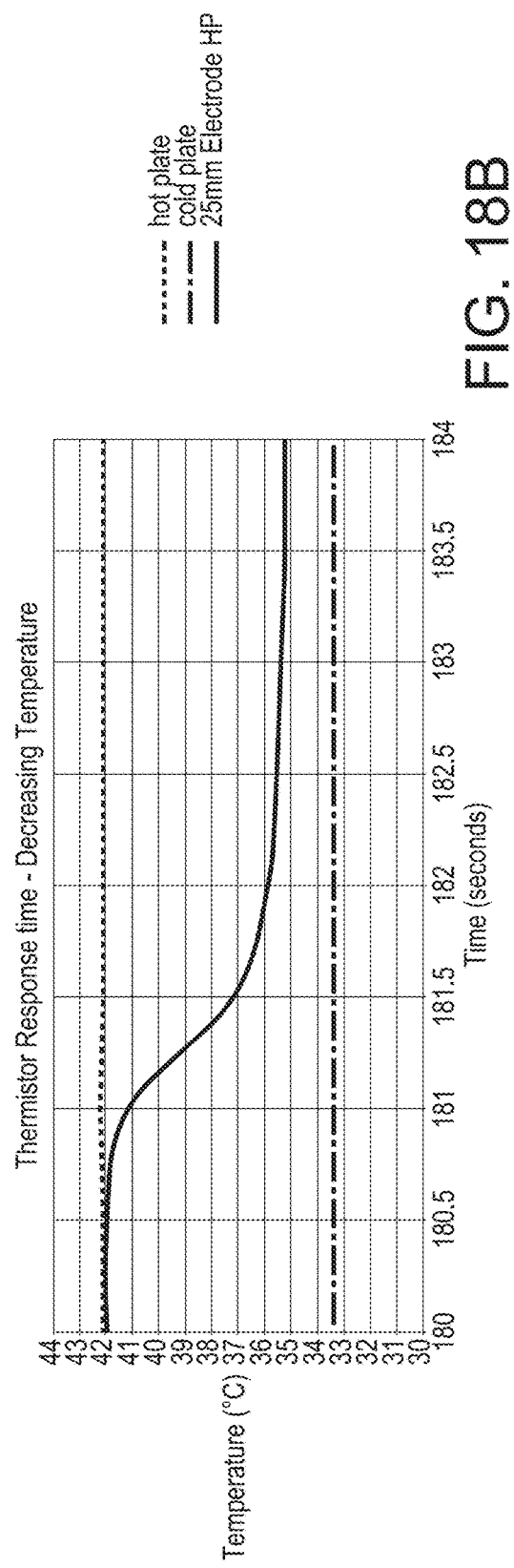

FIGS. 18A and 18B depict transient temperature responses to step changes in power for a working embodiment of a thermal sensor (e.g., a thermistor) in a 25 mm Tempsure™ electrode assembly, available from Cynosure, Inc, Westford, Mass. Specifically, FIG. 18A shows the transient response to an increase in temperature. FIG. 18B shows the thermistor assembly response time to a decrease in temperature.

Response Time

Looking at FIG. 18A, the temperature sensor as assembled in the Tempsure electrodes shows a measurement response time of 2 to 3 seconds when warming from skin temperature (35° C.) to a target treatment temperature 42° C., to within 1° C.

Looking at FIG. 18B, a similar response time occurs when cooling; from target treatment area at 42° C. down to typical skin temperature of 35° C.

Added note: Temperature reference cold and warm plates may be held constant with a heat exchanger to less than 0.5° C. of target temperatures Thermal Time Constant τ:

Thermal time constant τ of this 25 mm temperature sensing electrode is defined mathematically as the time it takes the temperature sensing electrode to reach 63.2% of the target temperature from its initial temperature, a difference of 7° C. 63.2% of 7° C. is 4.42° C. The thermal time constant of the assembled temperature sensor is therefore approximately 1 second for both graphs (add or subtract 4.42° C. from start of measurement on the curve and find elapsed time).

As generally understood and used herein, the "Thermal Time Constant", under zero conditions, is the time it takes a temperature sensor, e.g. a thermistor, to change 63.2% of the total difference between the initial and the final body temperature, when subjected to a step function change in temperature. In simple terms, it represents in time, how long it takes a temperature sensor to recover up to 50% of its initial resistance. When measuring for the thermal time constant, a temperature change needs to be applied. However, if that change is too slow, the measuring would be of the ambient rate of change; not the temperature sensor's response to the change. Therefore, it is preferable to use a temperature change as close to instantaneous as possible.

According to certain embodiments, the temperature sensor assembly's temperature sensor feedback is measured by a control system communicatively coupled to the RF amplifier. The control system compares the measured temperature of the temperature sensor to a user selected temperature. When the measured temperature feedback from the temperature sensor equals or exceeds the user selected temperature, the control system interrupts (e.g., diminishes or altogether stops) the RF emission. In some embodiments, a duty cycle of the RF emission can be adjusted (e.g., decreased) to maintain a temperature of a patient treatment site at or below an upper threshold temperature. When the electrode assembly moves to a cooler zone in the treatment area, the temperature sensor in the electrode assembly can detect a temperature below a user-selected temperature. As a result, the control system can re-engage or increase the RF emission from the electrode assembly. This process continues throughout a treatment session to maintain the desired temperature e.g., the user selected temperature, throughout the treatment area.

Figure 19:
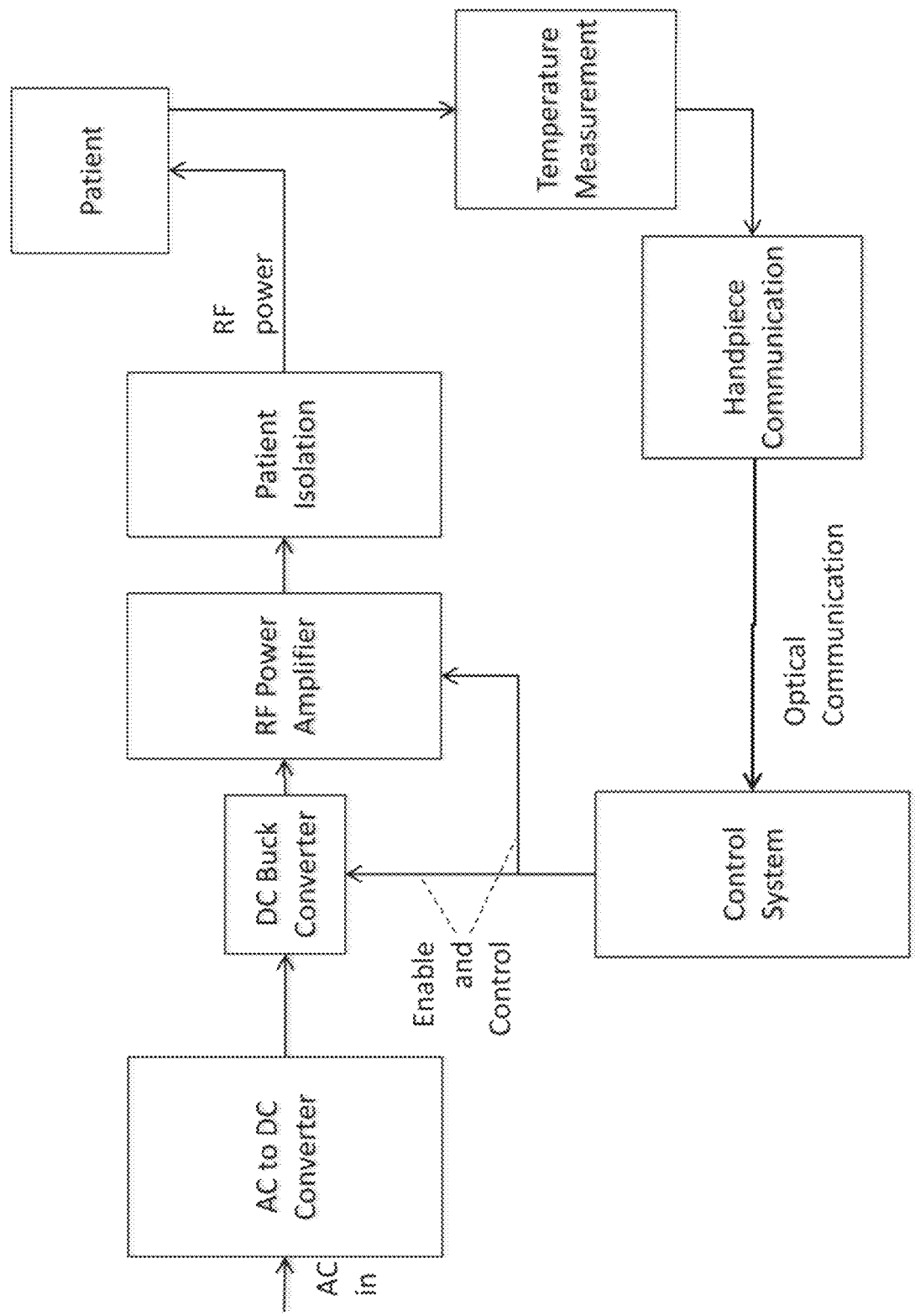
FIG. 19 schematically illustrates a block diagram of a temperature-controllable circuit topology for an electrosurgical system.

FIG. 19 is a block diagram that shows the control system interacting with the temperature sensor feedback around the treatment of a subject. Here, AC power is converted to DC voltage in the AC to DC converter. The DC voltage travels through the DC Buck Converter, which controllably lessens the supplied DC voltage. The supplied DC voltage is delivered to the RF Power Amplifier and then travels to patient isolation (e.g., a transformer). From patient isolation, the RF power is then delivered to the Patient. The Patient's skin surface is measured by the Temperature Measurement step, which utilizes a temperature sensor in the handpiece. The handpiece communication communicates the patient skin surface temperature measurement to the control system. In some embodiments, the handpiece communication optically communicates the temperature measurement to the control system. The control system compares the patient skin surface temperature to the desired patient skin surface temperature. The desired patient skin surface temperature may be defined as a threshold temperature and/or a threshold temperature within a range of temperatures, e.g. +/−2 C from the threshold. The control system enables and controls the DC Buck Converter and the RF Power Amplifier based on the how the patient skin surface measurement compares to the temperature threshold.

In one possible embodiment, the measured skin surface temperature measures at or higher than the temperature threshold or the top of the threshold range. When the message that the temperature exceeds the threshold is conveyed to the control system, the control system's enable and control shuts off the DC Buck Converter supply of DC voltage to the Amplifier, thereby disabling the RF power previously being delivered to the Patient. The temperature measurement feedback loop may optionally continue measuring the patient skin surface temperature in the Temperature Measurement step. When the measured patient skin surface temperature measures too low (e.g., lower than the temperature threshold, or below the bottom of the threshold range), the control system's enable and control will enable the DC Buck converter and the RF Amplifier to resume the supply of DC voltage, thereby enabling delivery of the RF power again. In this way, the temperature of the patient's skin surface temperature is closely monitored and controlled.

In one possible embodiment, the measured skin surface temperature measures at or higher than the temperature threshold or the top of the threshold range. When the message that the temperature exceeds the threshold is conveyed to the control system, the control system's enable and control inhibits or lessens the DC Buck Converter supply of DC voltage to the Amplifier, thereby lessening the RF power previously being delivered to the Patient. In some embodiments, the temperature measurement feedback loop will continue measuring the patient skin surface temperature in the Temperature Measurement step. When the measured patient skin surface temperature measures too low (e.g., lower than the threshold or the bottom of the threshold range), the control system's enable and control will enable the DC Buck converter supply of DC voltage to the Amplifier to increase the supply of DC voltage thereby enabling delivery of more RF power. In this way, the temperature of the patient's skin surface is closely monitored and controlled.

The improved response time temperature feedback sensor assembly has several notable requirements. The thermal conduction between the subject's tissue surface (e.g., skin surface) and the temperature sensor should be maximized. Or, stated differently, the thermal resistance between the patient and the temperature sensor should be minimized. Additionally, the temperature sensor thermal mass should be minimized to allow for detection of fast changes in temperature of the subject's tissue surface. Conversely, thermal conduction between the thermal mass of the electrode emitting the RF signal and the temperature sensor should be minimized. Or, stated differently, the thermal resistance should be maximized. In one possible embodiment, the thermal conduction between the electrode thermal mass and the temperature sensor is minimized by using a thermally insulated material that thermally insulates the temperature sensor assembly from the electrode assembly. Suitable thermally insulated materials include machinable plastic such as ULTEM™ available from SABIC (Riyadh, Saudi Arabia). Any of a number of thermally insulative materials are known and may be employed.

A goal of some electrosurgical treatment is to drive electricity into the tissue and uniformly heat the tissue under the electrode surface. With high frequency (e.g., 4 MHz) and an appropriate dielectric, the desired tissue depth may be achieved with surface uniformity. Lower frequency transmissions may dissipate too much energy in the dielectric material and can provide poor energy coupling between the energizable electrode and a treatment site. According to certain embodiments, capacitive coupling of electrodes helps achieve uniform distribution of electricity. With the disclosed, capacitively coupled approach, there is less thermal loss into the dielectric and relatively less power is lost. Therefore, more power is delivered into the tissue, compared with other devices that use a direct coupled approach and concomitantly cause electrode heating (akin to a hot rock). Such heating is undesirable and negatively impacts patient tolerance. The goal is to drive as much current into the body as is tolerable and to deliver more power to the deep tissue with minimal dielectric losses. A capacitive probe according to the embodiments can help fulfill these goals. If a selected electrode is purely resistive (as opposed to capacitive) then this limits the ability to achieve uniformity and opposes the goal of a higher amount of power delivered to tissue depth as uniformly as practicable.

In one embodiment, the electrode is made from an electrically conductive material (e.g., gold plated brass). Generally, materials employed to make electrodes may also be very thermally conductive (e.g., aluminum, gold, brass, etc.). In addition, most electrode constructions have a relatively large thermal mass. In an embodiment, the electrode has much more thermal mass than the temperature sensor (e.g., >100:1). One goal is to measure the subject's tissue surface temperature, rather than the temperature of the electrode itself, because a primary objective is to reach and maintain a target temperature of the subject's tissue surface (e.g., skin surface) throughout the treatment area. The electrode may have a large thermal mass, and may be at a different temperature than the subject's tissue surface (e.g., skin surface), therefore thermal conduction from the electrode to the temperature sensor risks causing a skew in the resulting temperature feedback. For example, when beginning the treatment with a room temperature electrode/ temperature sensor assembly, the large thermal mass of the room temperature electrode may saturate the temperature sensor with about 25° C. thermal conduction thus obscuring the subject's higher tissue surface temperature. In the case where the thermal mass of the room temperature electrode interferes with the temperature sensor, the temperature sensor would indicate a subject's tissue surface temperature lower than it is, which is a potential safety problem.

Thus, according to various embodiments, the temperature sensor thermal mass may be minimized to enable an improved speed of detection of changes in tissue surface temperature. Minimization may be achieved by controlling the amount of material (thermal mass) in contact with the temperature sensor (e.g., a thermistor). For example, the amount of material in contact with the temperature sensor may be minimized. Additionally, thermal conduction between the subject's tissue surface and the temperature sensor should be maximized (e.g., the thermal resistance between the tissue surface and the temperature sensor, $R_\theta$, should be minimized).

FIGS. 4-7 illustrate aspects of an electrosurgical handpiece including a temperature sensor assembly. The temperature sensor assembly includes a temperature sensor and housing to protect the temperature sensor. The housing can define a patient contact surface. For example, a patient contact surface of a temperature sensor assembly may be defined by a cylinder that surrounds all or a portion of the temperature sensor. The patient contact surface may extend longitudinally past (e.g., may be slightly "proud" relative to) a patient contact surface defined by the energizable electrode to ensure thermal contact between the housing and a treatment site.

In this way, the temperature sensor may be surrounded by a thermally conductive housing. A thermally conductive epoxy, paste, or other material suitable for reducing thermal contact resistance between the temperature sensor and the housing can enhance thermal contact between the temperature sensor and the housing. Such thermal contact can ensure that a temperature of the temperature sensor and a temperature of the housing remain approximately the same. Moreover, combining a low-mass housing and a low-mass temperature sensor can provide a rapid thermal response (e.g., a low thermal time constant) for the temperature sensor assembly.

Figure 20:
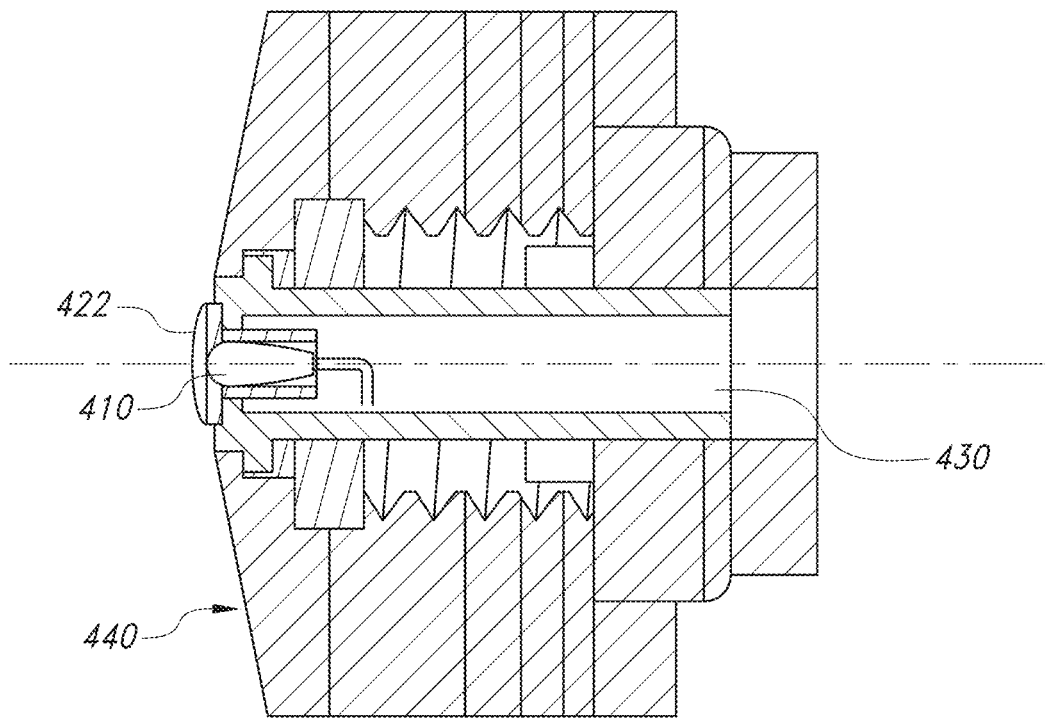
FIG. 20 shows a temperature sensor assembly incorporated in an electrosurgical handpiece of the type shown in FIG. 23.
Figure 21:
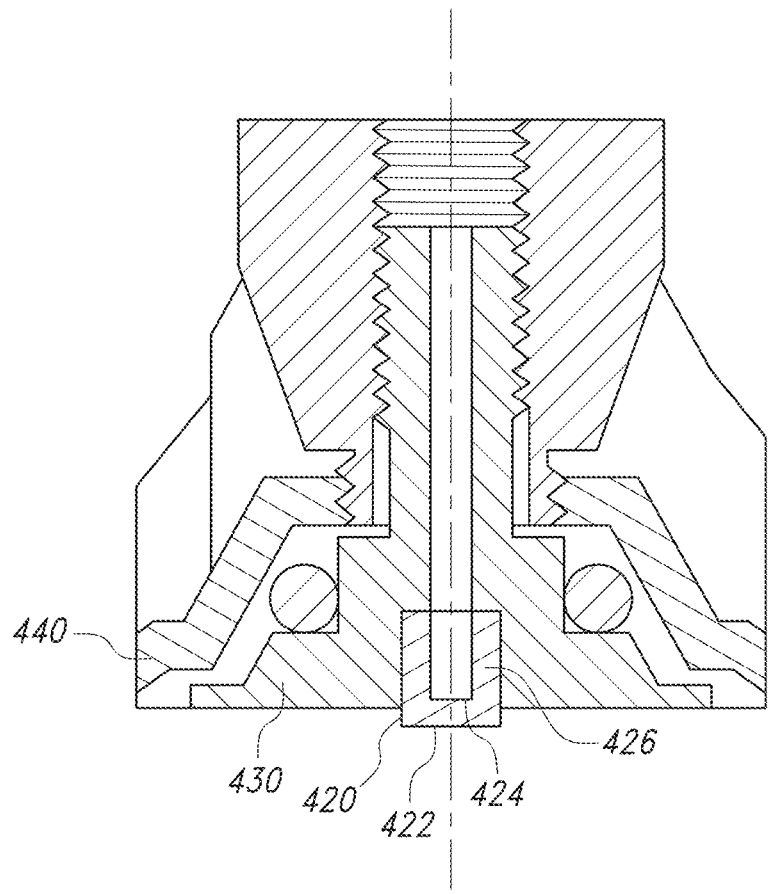
FIG. 21 shows another temperature sensor assembly incorporated in an electrosurgical handpiece of the type shown in FIG. 23.

FIGS. 20-21 show cross-sections of a temperature sensor assembly 402 that may be used in an electrosurgical handpiece. In the illustrated example, a temperature sensor 410 may be disposed inside a thermally conductive housing 420 (e.g., a thermally conductive cylinder, a thermally conductive sheath, a thermally conductive envelope). The temperature sensor 410 may be thermally coupled to the housing 420 such that the entire surface area of the temperature sensor 410 is in direct contact with the thermally conductive housing 420 and/or with a thermal epoxy or other coupling that is also in contact with the housing 420. By using the entire surface area of the temperature sensor 410, the thermal flux can be maximized, which can be conducted into the temperature sensor 410.

The thermally conductive housing 420 may include a first patient contact surface 422, an inner surface 424 that is positioned opposite the first patient contact surface 422, and an outer wall 426 that extends transversely relative to the first patient contact surface 422.

The thermally conductive housing 420 may be made from a relatively small amount of material (e.g., as small an amount of material as is possible) to limit the thermal mass and thereby improve the response time (e.g., quicken the response time). Generally, the housing 420 may be made from a thermally conductive material, e.g., having a thermal conductivity of about 200 Watts/meter-Kelvin (W/m-k), or about 400 W/m–K. In some instances, however, a thermally conductive and electrically non-conductive material, such as, for example, AlN (aluminum nitride) or other ceramic material, may be desirable.

Additionally, the portion of the temperature sensor assembly in contact with the patient or subject, e.g. a first patient contact surface 422, may be exaggerated to increase surface area in contact with the patient (or subject) and to increase thermal conduction to the temperature sensor 410 therethrough. The portion of the temperature sensor assembly 402 in contact with the patient has a larger surface area than the portion of the temperature sensor 410 that it contacts. The exaggerated surface area of the point of contact of the temperature sensor assembly with the tissue surface is desirable because the tissue is a relatively poor thermal conductor and exaggerating the area in contact with the tissue, compensates for the relatively poor conductivity of the tissue relative material in contact therewith (e.g., metal point of contact of the temperature sensor assembly).

Any number of shapes of the portion of the temperature sensor assembly in contact with the tissue, e.g., the first patient contact surface 422, may be selected, for example, a disk (e.g., like a hockey puck), a rectangle, a sphere, or a mushroom cap shape. The first patient contact surface 422 may flare out radially from a shaft or body of the sensor. The flared portion may have a radial extension that is a multiple of the general diameter of the shaft or body of a temperature sensor. For example, the diameter of a mushroom or disk tissue contacting portion, e.g., the first patient contact surface 422, may be at least 2, 3, 4 5, 6, 7, 8, 9, 10, 15, 25, 30, or more times the diameter of the temperature sensor body, as the mushroom contact portion and associated temperature sensor are oriented in FIG. 20, for example. The first patient contact surface 422 may be tailored (e.g., smoothed such that what contacts the tissue surface lacks sharp or pronounced edges) to comfortably contact the patient's tissue surface when the device is moved across the subject's tissue surface (e.g., skin surface).

The temperature sensor assembly 402 may also include an insulator 430. The insulator 430 may be outside of the housing 420 and between the housing 420 and an energizable electrode 450 (of which only a portion is depicted), and may span a gap between the outer wall of the housing 420 and the electrode 450. The insulator 430 may completely fill the gap in an embodiment. Alternatively, the insulator 430 may only partly fill the gap while the remaining volume in the gap is filled with a gas and/or another dielectric material.

In one possible embodiment, the insulator 430 may minimize the thermal conduction between the thermal mass of the electrode 450 and housing 420 (and the temperature sensor 410). The insulator 430 may be or use a material that thermally insulates the temperature sensor assembly 402 from the electrode assembly. Suitable thermally insulated materials include machinable plastic such as ULTEM™ available from SABIC (Riyadh, Saudi Arabia). Any of a number of thermally insulative materials are known and may be employed. In one possible embodiment, the edges of the temperature sensor assembly portion in contact with the patient, e.g. the first patient contact surface 440, are rounded off such that it is mushroom shaped, which provides patient comfort as the sensor assembly is swept along the patient's skin surface. This mushroom tip surface and the adjacent cylinder, e.g. housing 420, act as a housing around the temperature sensor 410, making the assembly well suited for fast response temperature feedback. The mushroom shape may protrude in part past a surface of the electrode, and may provide a larger surface area compared to a flat tip for greater contact with the treatment surface.

Also, as stated above, thermal conduction between the electrode thermal mass and the temperature sensor should be diminished or minimized (max Re) to prevent errors or a skew in the temperature sensor feedback accuracy. Thermal conduction between the electrode thermal mass and the temperature sensor assembly can be minimized by means of a thermal insulating barrier (e.g., a thermal insulator sleeve) inserted between the large thermal mass of the electrode and the temperature sensor assembly.

Figure 22:
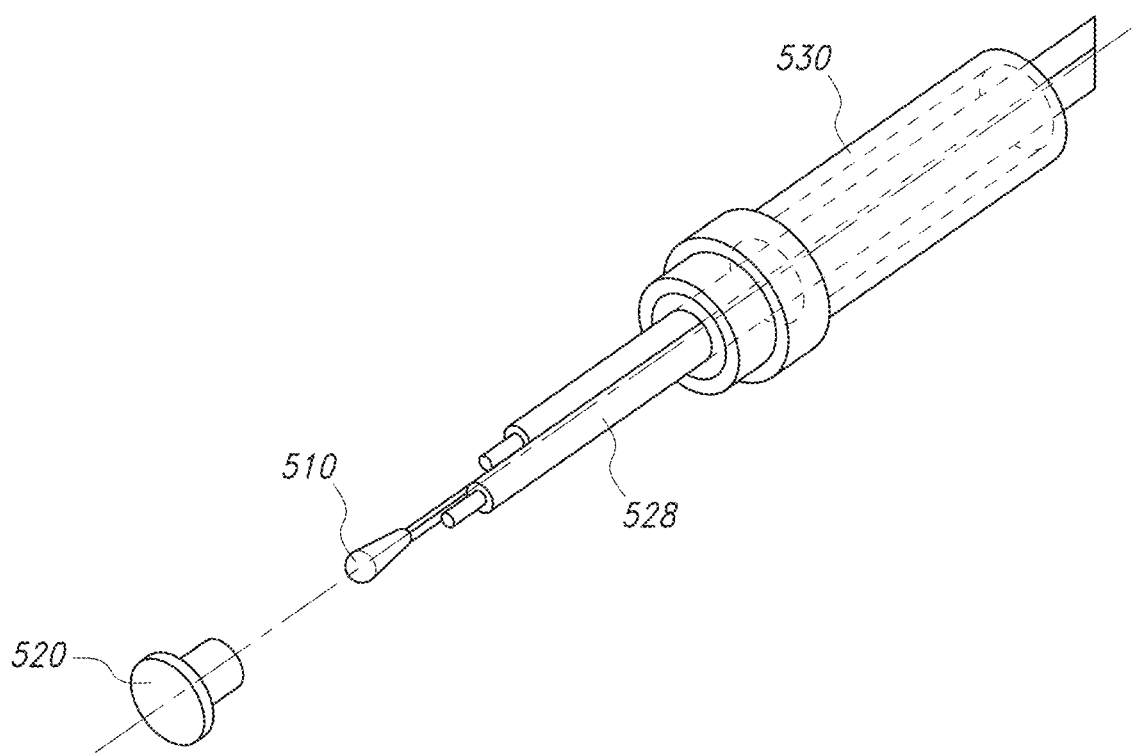
FIG. 22 shows an exploded view of a temperature sensor assembly incorporating a thermistor.

In one embodiment, as shown in the exploded view in FIG. 22, the temperature sensor assembly may be a thermistor assembly 502, which includes a thermistor 510, a thermally conductive container 520 (e.g., a mushroom shaped tip with an adjacent cylinder) and thermal epoxy to couple the thermistor 510 to the container 520. Additionally, a thermal insulator 530, thermal resistance, or $R_\Theta$, is selected to be as high as possible while still meeting practical requirements such as strength, rigidity or machinability. Electrical conductor 528 may conduct temperature sensing information to a control system directly or indirectly via a transmitter (not shown).

A temperature sensor assembly that uses a thermocouple instead of a thermistor may be similar to the assembly shown in FIG. 22, albeit with a thermocouple instead of a thermistor. The housing used for a thermocouple may have a shorter outer wall compared to the outer wall of the housing 520, as described, for example, with respect to FIGS. 28A-B. That reduction in material used for the housing can reduce the mass of the housing, and thus a thermal time constant for the temperature sensor assembly. Further, a thermocouple may have less mass than a thermistor, which can further enhance transient response times. However, these advantages may not outweigh disadvantages of many thermocouples, including inaccuracy arising from, for example, calibration drift, signal cross-talk with other electrical circuits, etc.

Figure 23:
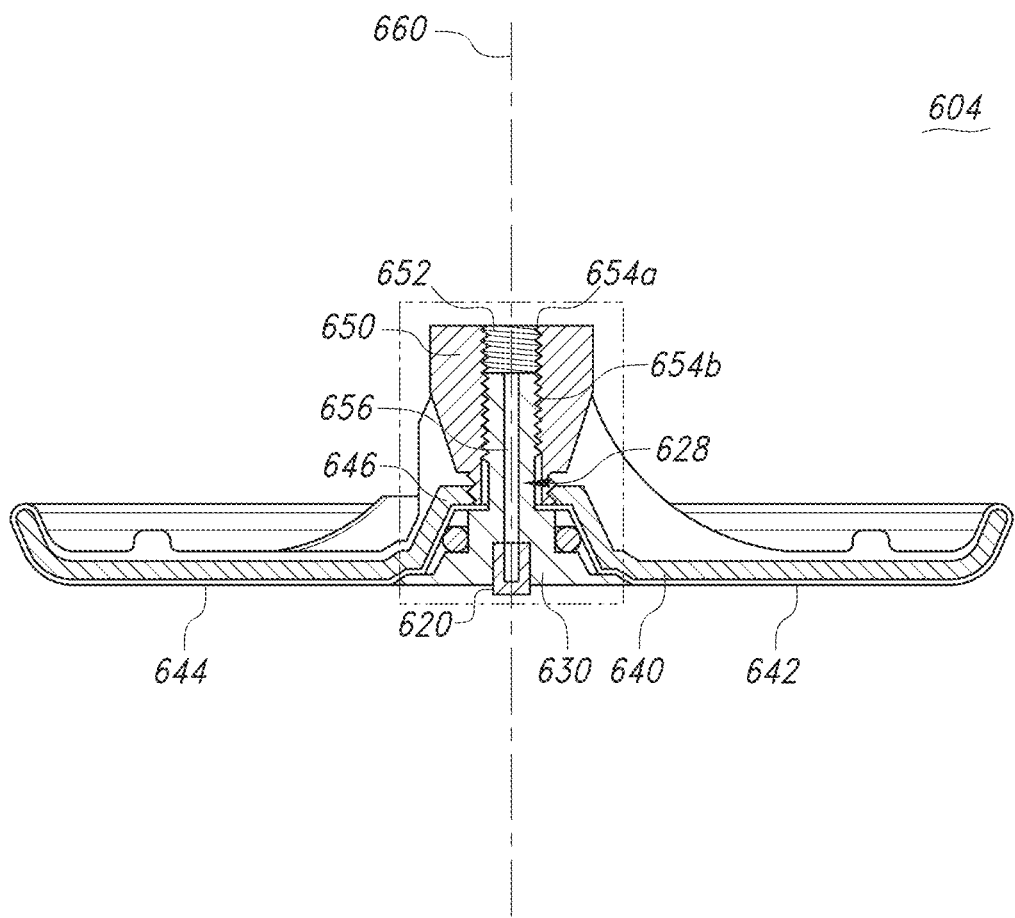
FIG. 23 shows a cross-sectional view of a portion of an electrosurgical handpiece that includes a temperature sensing assembly.

FIG. 23 depicts an example of a portion of an electrosurgical handpiece 604 in cross-section that includes a temperature sensing assembly. The temperature sensing assembly may be the same or similar to the temperature sensing assembly 402 or 502. For example, the housing 620 and the insulator 630 may be analogous to housing 420, 520 and to insulator 430, 530, respectively. The portion of the figure within the dotted line box may represent the view as shown in FIG. 21.

In addition to the temperature sensing assembly, the handpiece 604 may include an energizable electrode 640 defining a second patient-contact surface 642 extending outward of the outer wall of the housing 620. In various embodiments, a low thermal mass material, e.g., a material having a lower thermal mass that the tissue being contacted, may be used for the electrode 640 to offer further improvement in temperature measurement accuracy of the temperature sensor, because it avoids cross talk between a thermal mass of the electrode 640 and the temperature sensor in the temperature sensing assembly. Stated differently, an electrode that has a low thermal time constant can readily change temperature with its environment, improving a temporal response of the temperature sensing assembly relative to an electrode/temperature sensing assembly in which the electrode as a relatively higher thermal time constant. Accordingly, the temperature of the subject's skin surface is measured rather than the temperature of the electrode 640 itself.

In an ideal case, the thermal mass of the electrode 640 surrounding the temperature sensor is as close to zero as is possible. In this way, interference of any thermal mass of the electrode might be avoided.

For example, in one embodiment the electrode 640 may be a metal foil that surrounds a void and has a temperature sensor disposed inside the void and in contact with the subject's tissue surface. Here, any gas such as air in the void acts as the insulator and has minimized mass to cross talk with the temperature sensor. In another embodiment, the electrode 640 may be a metal foil that surrounds a low thermal mass solid such as fiber insulation (e.g., plastic, pulp, paper, glass, etc.) or solid plastic and has a temperature sensor disposed inside the metal foil and in contact with the subject's tissue surface and likewise this low thermal mass material minimizes cross talk with the temperature sensor thereby improving accuracy of the temperature sensing of the subject's skin surface. In still another alternative embodiment, the electrode 640 may be made of solid plastic (having a high thermal resistance) and coated with a thin layer of conductive material such as a gold foil. The thin foil layer ensures RF energy conducts via the thin foil layer. An electrode made from a thin foil layer around a void filled with gas, an electrode made from a thin foil layer around a low thermal mass solid such as plastic, and the electrode made from metal surrounding an insulative cylinder that separates the thermal mass of the electrode from the temperature sensor all provide RF energy to the subject in a similar way, by means of a skin effect about the outside surface of the electrode.

The electrosurgical handpiece 604 may be used as a capacitive heating probe to provide a tuned uniform deep tissue heating system. A metal inner probe body, e.g., the energizable electrode 640, has an exterior surface, e.g., second patient contact surface 642, that may be covered with a dielectric coating 644. Absent the dielectric coating 644, the second patient contact surface 642 may be the surface of the electrode itself. When present, the dielectric coating 644 becomes the second patient contact surface 642, as it, and not the electrode, will come in contact with the treatment surface. The dielectric coating 644 may be employed to enable the treatment current to be delivered homogenously over the entire area where the dielectric coated surface of the electrode is in contact with the subject's skin surface. The constraints on the dielectric may include: the material property, thickness of coating, and applied voltage.

Embodiments of the handpiece 604 as a capacitive heating probe provide several benefits: uniform tissue heating over the probe area in contact with the skin surface, a relatively large active tissue heating treatment area on the skin (e.g., greater than 30 mm in diameter, from about 40 mm to about 100 mm, or from about 40 mm to about 60 mm), and relatively deep tissue heating caused by Joule (or resistance) heating.

Additional aspects of this system include a high frequency energy source ("HF", defined by the International Telecommunications Union (ITU) as greater than 3-30 MHz) combined with a capacitive tissue heating probe with a specially-formulated dielectric coating 644. The coating 644 may have a high dielectric constant, e.g., between about 4 to about 8, e.g., between about 5 and about 7, at the operating frequency, e.g., at 4 MHz. Dielectric constants of about 2, e.g., between about 1.9 and about 2.1 may be considered low in this context. In addition, dielectric coatings that may be employed desirably have properties that include the ability to be applied with a controllably even thickness, e.g., at a uniform thickness over the second patient contact surface.

Additionally, the dielectric coating may desirably be rugged enough for multiple uses and may be resistant to chipping and cracking. The dielectric coating may be biocompatible with human tissue; impervious to fluids; and non-absorptive to moisture. The dielectric coating may also have a low coefficient of friction against human tissue. The dielectric coating may have a relatively high loss tangent for a polymer at 4 MHz, e.g. a loss tangent of at or above 0.5. Low loss tangents, e.g., for other materials, may be in the range of 0.0004 to 0.001. The high dielectric constant, relatively low thickness (e.g. about 0.01 inches) of the dielectric applied to the surface, and the frequency range of the RF disclosed herein can work in combination to inhibit or prevent arcing to the tissue.

The tissue may be protected from arcing damage due to the system design that controls voltage, dielectric material thickness, frequency, and material dielectric constant. Previous capacitive tissue heating systems have used medium frequency energy sources ("MF" defined by the ITU as 300 kHz-3 MHz), which are not as effective at driving deep Joule tissue heating with capacitive probes due to dielectric losses and corresponding reduction of current to deep tissue. In one embodiment, the RF energy source operates at 4 MHz and conveys a waveform to the electrode having a frequency of 4 MHz, i.e. the operating frequency. The capacitive energy probe may have a diameter that is greater than 40 mm. The dielectric coating has less impedance to high frequencies and the 4 MHz system is a relatively high frequency system and therefore presents lower dielectric loss. As a result, less RF energy is lost to heating the electrode and instead is available to penetrate as a homogenous current into the depths of the tissue of the subject. Accordingly, the subject, treated at 4 MHz with the provided dielectric coated electrode capacitively coupled current, may experience a larger bulk of tissue being treated than would the same tissue would experience with the same dielectrically coated electrode capacitively coupled current at 400 kHz. With 4 MHz a 5% dielectric loss would approach 50% dielectric loss at 400 kHz. Thus, a 400 kHz system is capable of delivering substantially less current to deep tissue than the 4 MHz system when using a capacitive heating probe as described.

Additionally, the capacitive probe design features a direct, fast measurement of tissue surface temperature and also provides electrical isolation of the temperature measurement interface from the metal probe body as discussed herein. Thus, the undesirable skew in temperature feedback caused by thermal conduction to the temperature sensor is avoided due to the electrical and thermal isolation of the temperature measurement interface form the metal probe body.

The handpiece 604 may further include a shaft 650 extending proximally from the energizable electrode 640 and defining a first internal bore 652 extending longitudinally of the shaft 650. In an embodiment, the insulator 630 may extend through an opening (see opening 744 in FIG. 24) in the energizeable electrode 640 and into the first internal bore 652 of the shaft 650. The shaft 650 may be in contact with the energizeable electrode 640 at a shoulder 646 of the electrode. The energizeable electrode 640 is energized by an RF generator (not shown). The insulator 630 may extend from a distal end positioned adjacent the first patient-contact surface of the housing 620, and the second patient-contact surface 642 to a proximal end positioned within the first internal bore 652. The insulator 630 may have a second internal bore 656. In an embodiment, the internal bore 652 may have one or more first threads 654a, and the insulator 630 may have one or more second threads 654b. The first and second threads 654 may be complementary and matingly engageable with each other. When mated together, via the threads 654 or by other coupling means, the shaft 650 and the insulator 630 may capture the energizeable electrode 640 between them. When captured, the energizeable electrode 640 may be generally fixed such that it cannot move longitudinally with respect to the shaft 650 or the insulator 630. In some embodiments, the energizeable electrode 640 may be free to rotate about the longitudinal axis 660, and in other embodiments, the energizeable electrode 640 may be rotationally fixed. The energizeable electrode 640 may, in some embodiments, be able to pivot with respect to the shaft such that the axis of the shaft is at an angle to the longitudinal axis 660 to allow the energizeable electrode 640 to follow contours on the treatment surface and provide greater comfort for the human operator.

The handpiece 604 may further include an electrical conductor 628 extending proximally within the handpiece 604 from the temperature sensor in the housing 620 and through the second internal bore 656. The electrical conductor 628 may conduct a signal from the temperature sensor to a control system, or to a communication component (not shown) in the handpiece that can transmit the temperature sensor signal to a control system wirelessly or via a wire.

In an embodiment, the first patient-contact surface and the second patient-contact surface 642 may be co-centrically aligned with each other. As used herein, the phrase "co-centrically aligned" means each respective centroid in a plurality of centroids overlaps with or is coextensive with one of the other centroids, or a line joining two of the centroids is substantially parallel with a longitudinal axis of related structure. For example, the centroids of the first and the second patient-contact surfaces may be spaced apart from each other, but they are aligned substantially axially relative to a longitudinal axis 660 of the housing and/or the electrode.

Figure 24:
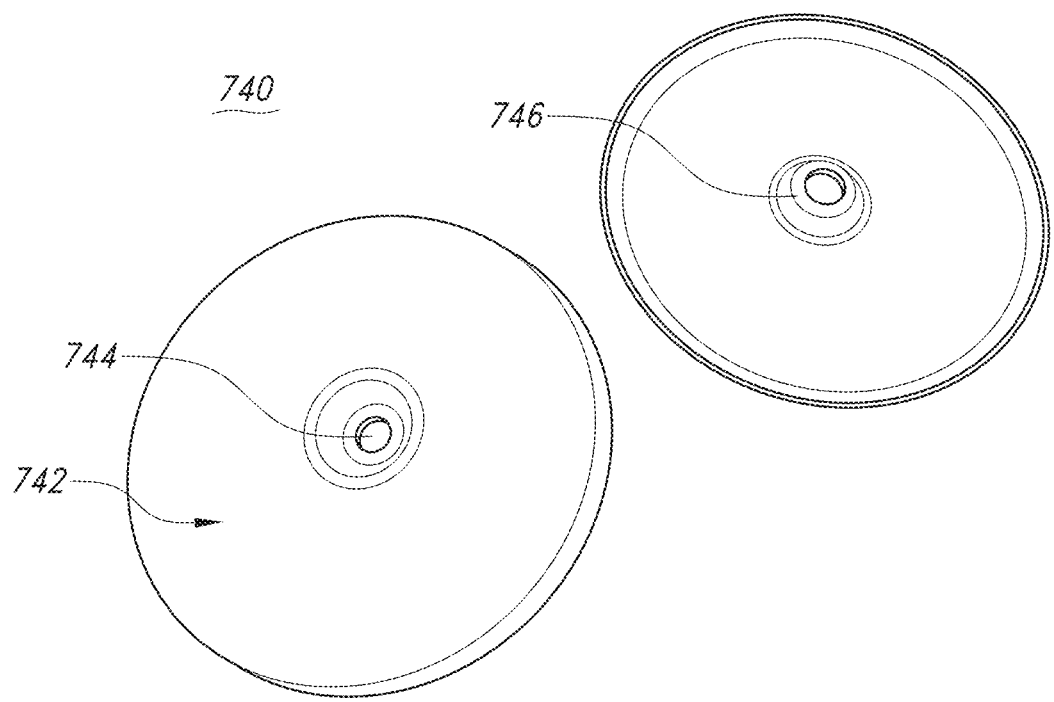
FIG. 24 shows a working example of an energizable electrode having a dielectric coating.
Figure 25:
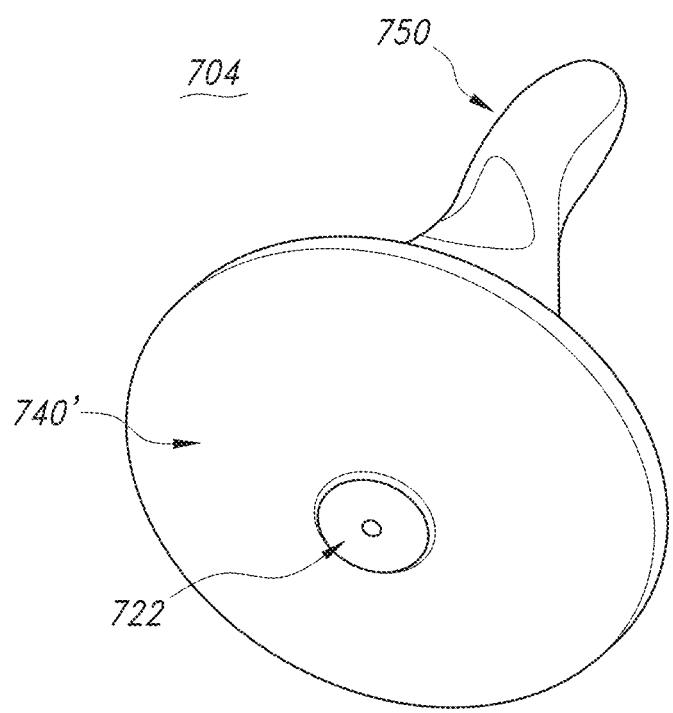
FIG. 25 shows a working example of an electrosurgical handpiece having an energizable electrode as in FIG. 24.

FIGS. 24 and 25 show examples of electrodes and capacitive probes according to various embodiments. FIG. 24 shows a proximal view (right) and a distal view (left) of an embodiment of an energizable electrode 740. The second patient contact surface 742 is visible on the electrode on the left. The electrode 740 may be coated with a dielectric material. The energizeable electrode 740 defines an opening 744 in which a temperature sensing assembly may be positioned. A shoulder 746 may surround the opening 744 and extend distally.

FIG. 25 shows an embodiment of an electrosurgical handpiece 704, that may be used, for example, as a capacitive probe. The electrosurgical handpiece 704 may be an embodiment of the handpiece 604, and may use the energizeable electrode 740, or an energizeable electrode 740' that may be similar to the energizeable electrode 740. The electrosurgical handpiece 704, as shown, has a temperature sensing assembly positioned at its center such that the first patient contact surface 722 is visible on the distal side. Also visible is a shaft 750 which may be graspable by a human or robotic operator of the handpiece 704.

Figure 26:
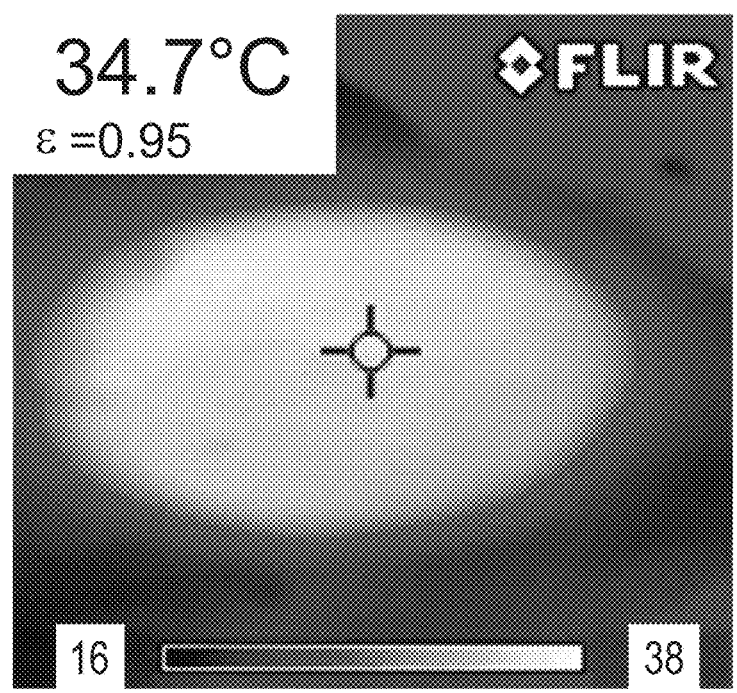
FIG. 26 shows surface temperatures of a treatment site based on an infrared (IR) scan of the treatment site.

FIG. 26 shows treatment results using probes such as those shown in FIGS. 24 and 25. The treatment results demonstrate uniform tissue heating or substantially uniform tissue heating on the body of a subject as measured by skin surface temperature using an IR camera. Here, referring to FIG. 26, the probes shown in FIGS. 24 and 25 were attached to an RF generator providing continuous sinusoidal RF energy at a fundamental frequency of about 4 MHz. In an exemplary treatment the probe was applied to the surface of a subject's skin and was moved by the clinician over the subject's skin surface to provide an increase in temperature with a treatment temperature measured at the skin surface of 34.7 C. The surface of the treatment area shown in FIG. 26 has uniform/homogenized heating such that once the temperature threshold for 34.7 C is reached, the whole homogenized area is at the 34.7 C temperature threshold. The temperature sensor was set to a temperature of 34.7 C and the sensed temperature sensor feedback is measured by the control system for the RF amplifier (discussed above). The control system for the RF amplifier compares the temperature measured by the temperature sensor to the user selected temperature and when the measured temperature feedback from the temperature sensor equals or exceeds the user selected temperature, the control system interrupts the RF emission. When the temperature sensor on the electrode assembly senses a temperature that is less than the user selected temperature, for example, when the probe has moved to a cooler area, the control system re-enables the RF amplifier and the RF emission resumes. As a result, the probe must be moved over the surface of the skin substantially continuously so that the temperature sensor functions without interruption. This avoids over- and under-treatment. Thus, the described probe should not be used in stamping mode, because there would be interruption in RF energy due to exceeding the user selected temperature.

Figure 27:
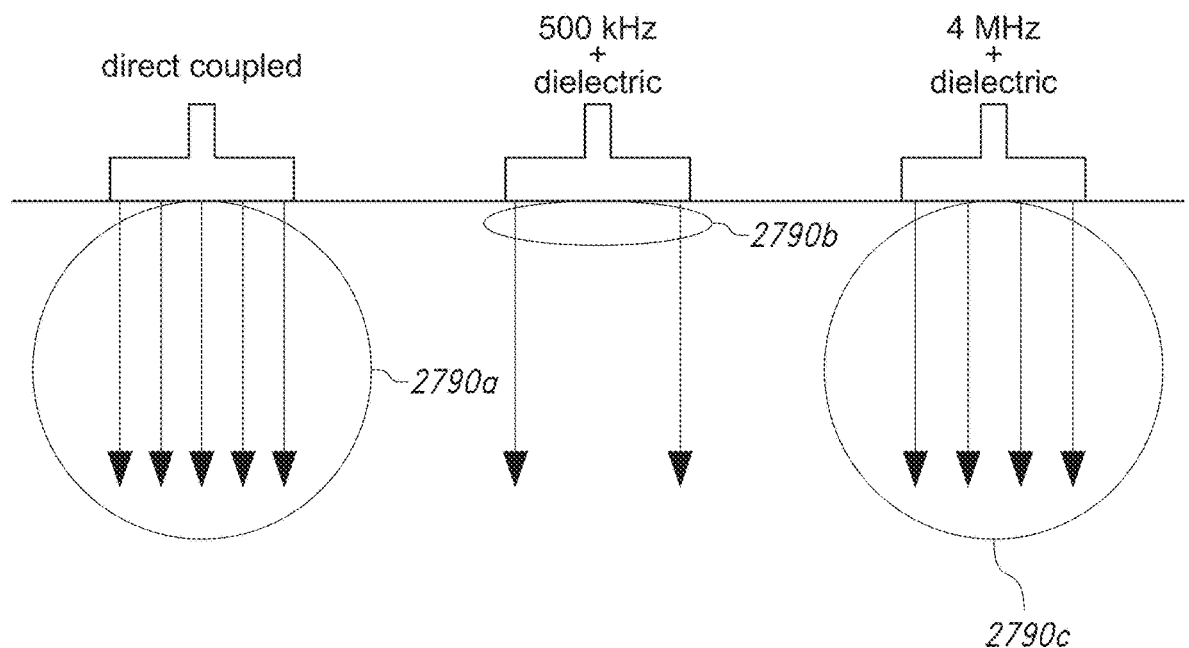
FIG. 27 schematically illustrates differences in tissue heating among different combinations of fundamental frequency and electrode configurations.

FIG. 27 is a depiction of the differences in surface heating of the skin that occur with three different embodiments of probes. The left side in FIG. 27 shows a direct coupled probe having dimensions similar to the probe shown in FIGS. 24 and 25. The middle of FIG. 27 shows a capacitively coupled probe having dimensions similar to the probe shown in FIGS. 24 and 25, but operating at an RF frequency of 500 kHz and with a dielectric. The right side in FIG. 27 shows a capacitively coupled probe operating at an RF frequency of 4 MHz and with a dielectric similar to the probe shown and described in association with FIGS. 24 and 25. As shown, the directly coupled probe and the probe operating at an RF frequency of 4 MHz provide relatively deep heating of tissue. The probe operating at an RF frequency of 500 kHz provides relatively shallow heating of tissue due to power losses in the electrode dielectric coating and subsequent electrode heating.

Figure 28A:
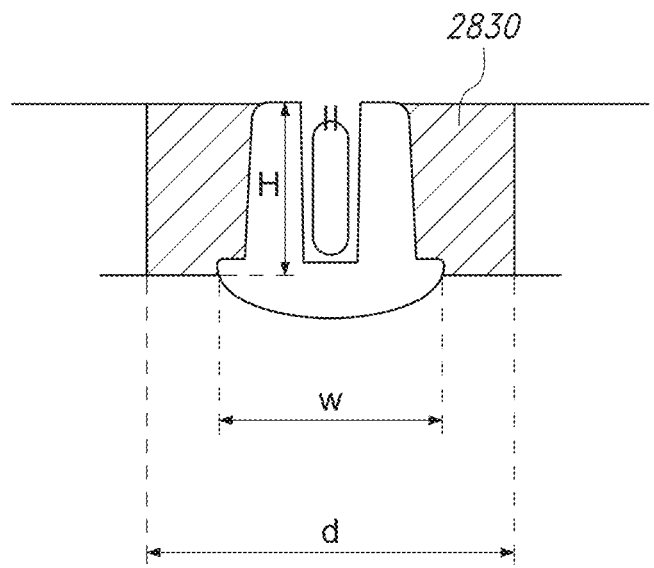
FIG. 28A schematically illustrates representative dimensions of a portion of an energizable electrode having a temperature-sensor assembly incorporating a thermistor.
Figure 28B:
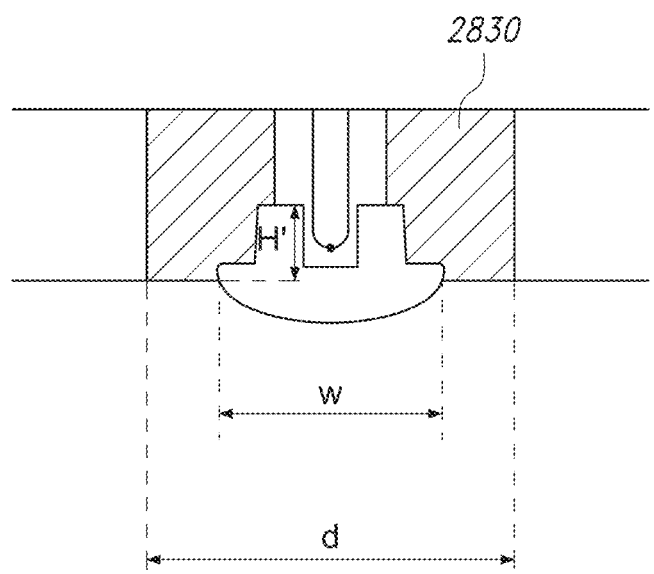
FIG. 28B schematically illustrates representative dimensions of a portion of an energizable electrode having a temperature-sensor assembly incorporating a thermocouple.
Figure 29:
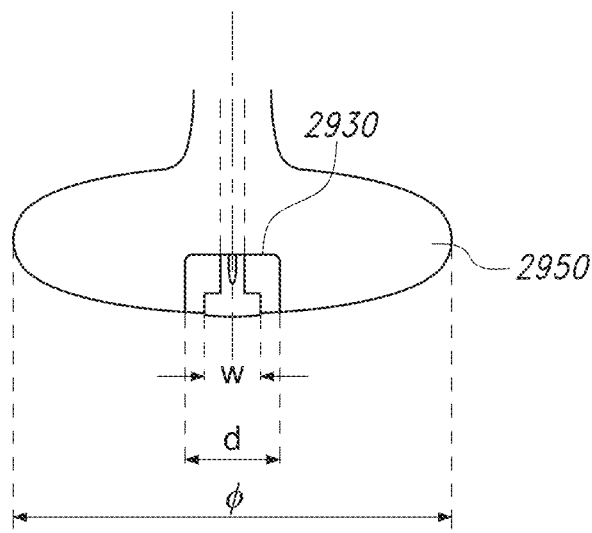
FIG. 29 schematically illustrates representative dimensions of an energizable electrode incorporating a temperature-sensor assembly.

FIGS. 28A-B, 29 and 30 illustrate various possible dimensions that be used in embodiments of the temperature sensing assembly and the electrosurgical handpiece. For example, as seen in FIGS. 28A-B, 29, the housing may have a width w at the first patient contact surface that may be less than or equal to about 5 mm. The insulator 2830 may have a diameter d (or width, if not circular) that may be between about 10 mm and about 90 mm.

As shown in FIG. 28A, in an embodiment that uses a thermistor as a temperature sensor, the height of the outer wall of the housing may extend upward to a height H in order to maintain a thermally isolated and insulated space around the entire temperature-sensitive body of the thermistor. As shown in FIG. 28B, in an embodiment that uses a thermocouple, the outer wall may only extend to a shorter height H', because only the tip end of the thermocouple is temperature-sensitive.

As shown in FIG. 29, the conductive annulus of the electrode 2950 may have a width greater than or equal to about 5 mm, as defined between an outer diameter of the electrode that is proximal to the perimeter of the handpiece and an inner diameter of the electrode that is proximal to an outer diameter of the insulator 2930. The handpiece may have an overall diameter (or width) phi, for example, of about 100 mm. The insulator may have a diameter d that is large, relative to the width of the electrode annulus, e.g., d between about 34 and 90 mm. The insulator may have a diameter d that is smaller than the width of the electrode annulus, e.g., d between about 10 and about 33 mm. In a purely resistive electrode, a larger and/or more thermally resistant insulator may be desirable to minimize or reduce effects of a heated electrode on the thermal sensor. Thermal resistance of an insulator can be based on a combination of material and thickness along heat-transfer direction. For example, an insulator with a high thermal resistance placed between the electrode and the housing can inhibit heat-transfer between the two and improve measurement accuracy relative to skin temperature. In a capacitive or dielectric-coated electrode, a larger electrode relative to the insulator may be desirable to provide a larger treatment surface.

The first patient contact surface of the housing may generally be in the same plane as the surface of the electrode, or may protrude past the surface of the electrode, for example, in a rounded manner as shown in FIGS. 28A, B. The protruding embodiment may increase the surface area and therefore the thermal contact area of the first patient contact surface relative to a non-protruding embodiment, and may therefore provide a more accurate or stable temperature measurement.

Figure 30:
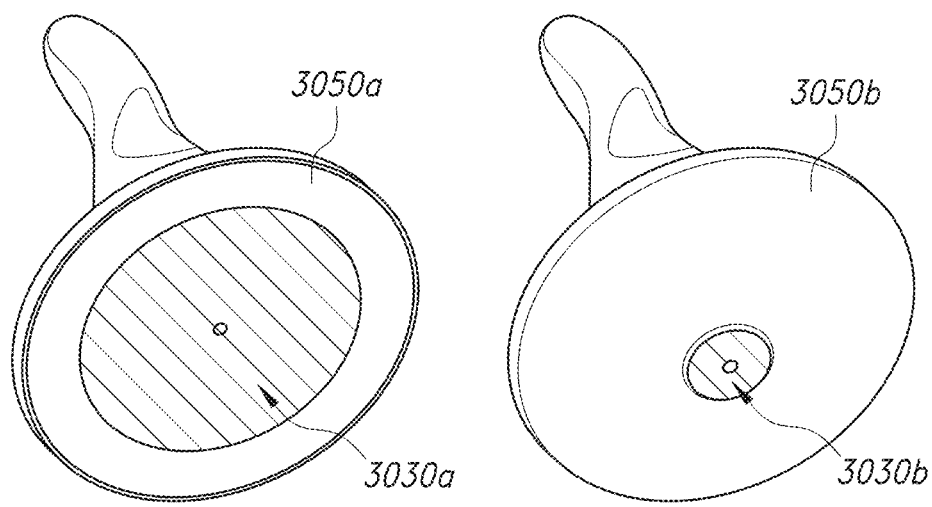
FIG. 30 schematically illustrates possible variations in relative dimensions of an insulator relative to an energizable electrode.

FIG. 30 shows two possible embodiments having different diameters d of the insulator. In the embodiment on the left, the insulator 3030a has a large diameter relative to the width of the electrode 3050a, and reduces the overall surface area of the electrode. In contrast, in the embodiment on the right, the insulator 3030b has a small diameter relative to the width of the electrode 3050b, such that the electrode has a relatively larger surface area. Other possible embodiments with different relative widths of the insulator may be used without departing from the disclosed concepts.

Figure 31:
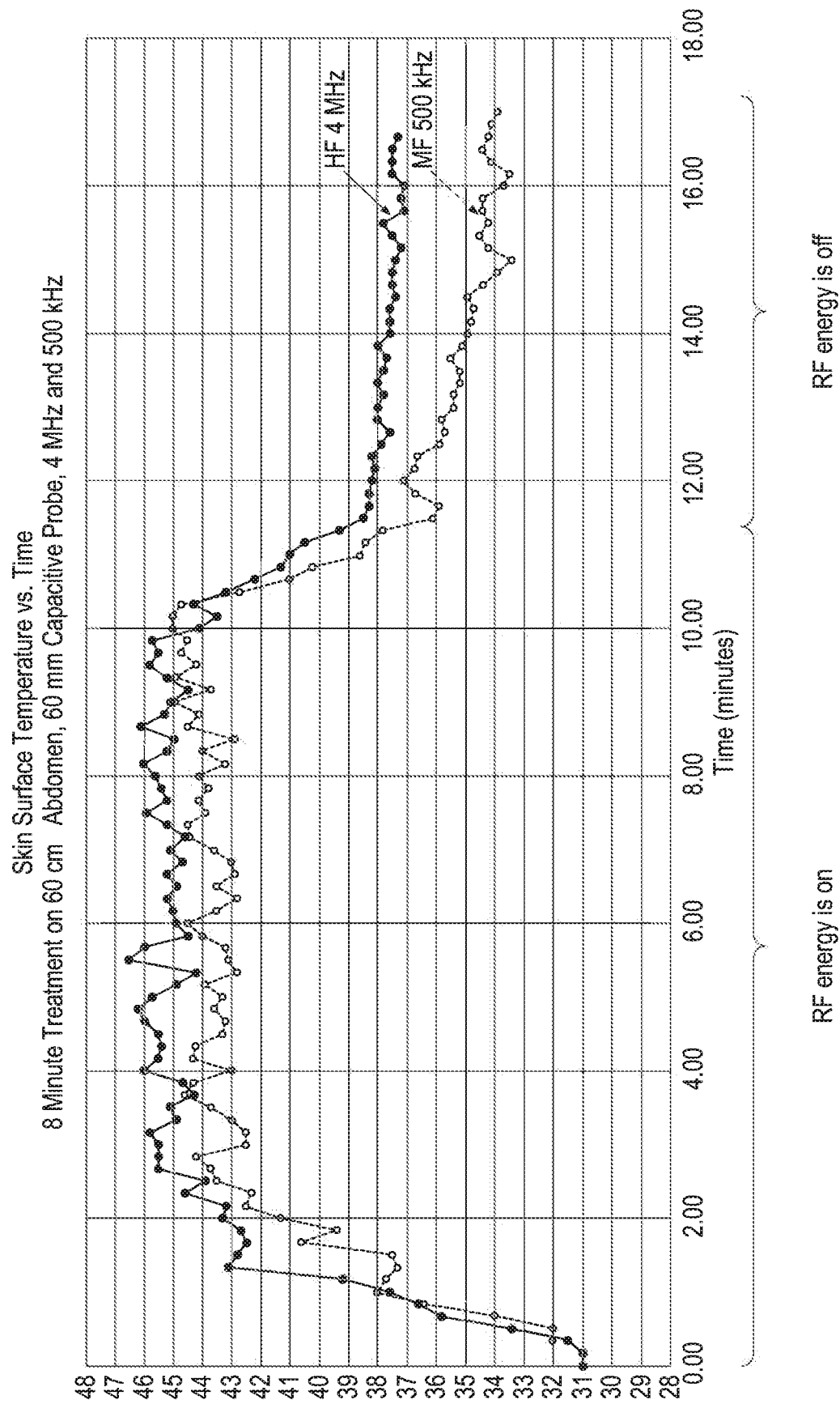
FIG. 31 schematically illustrates transient temperature response of a treatment site exposed to different electrosurgical waveforms.

FIG. 31 is a graph of skin surface temperature vs. time for a probe, as described in association with FIG. 27 and FIGS. 24 and 25, operating at 500 kHz, and a probe operating at 4 MHz. In this graph, two capacitive treatments are given to the same subject and the same anatomical area for the same amount of time using two different energy sources with different frequencies. Surface temperature is measured using an infrared (IR) camera. The MF 500 kHz energy source heats the surface of the tissue for about 8 minutes (here heating is judged to begin when the surface temperature reaches 39° C.) at the desired temperature, but when the energy is removed, at about the time of 10.5 minutes on the X-axis, the surface of the skin quickly cools down, which is indicative of skin and shallow tissue heating only (the deeper tissues have not been heated). Conversely, when the same test is run with the HF 4 MHz energy source that heats the surface and the depths of the tissue for about 8 minutes (heating is judged to being when the surface temperature reaches 39° C.), and the energy is removed at about the time of 10.5 minutes on the X-axis, the skin temperature remains significantly higher for a longer period, which is indicative of deeper tissue heating with the 4 MHz device than with the 500 kHz device.

Figure 32A:
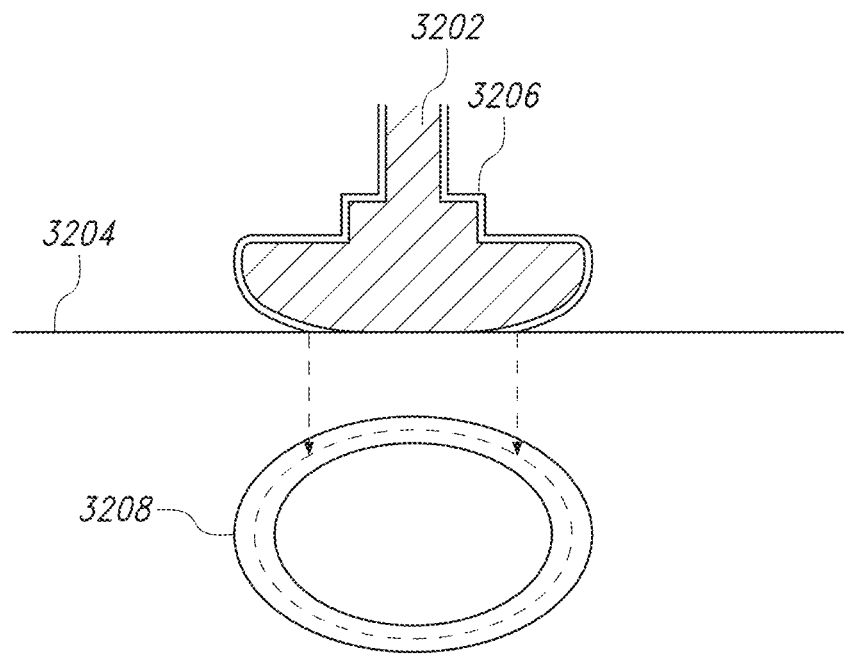
FIG. 32A schematically illustrates a typical, annular heated region of a treatment site arising from a direct-coupled electrode in contact with a patient's skin surface.

FIG. 32A shows a direct-coupled electrode 3202 having a relatively small surface area in contact with a patient's skin surface. Exemplary direct coupled electrodes include the Glidesafe 15 mm electrode sold with the Penevé® Wrinkle Reduction System, which is available from Cynosure, Inc. The active area of the directly coupled electrode and the skin effect limits the depth of the electrical current that travels from the direct coupled electrode to the patient's tissue. The current path 3206 travels only on the surface of the electrode 3202 until it encounters resistance, e.g. the skin surface 3204. The path of the electrical discharge results in a ring of current 3208 being delivered to the subject's surface tissue.

Figure 32B:
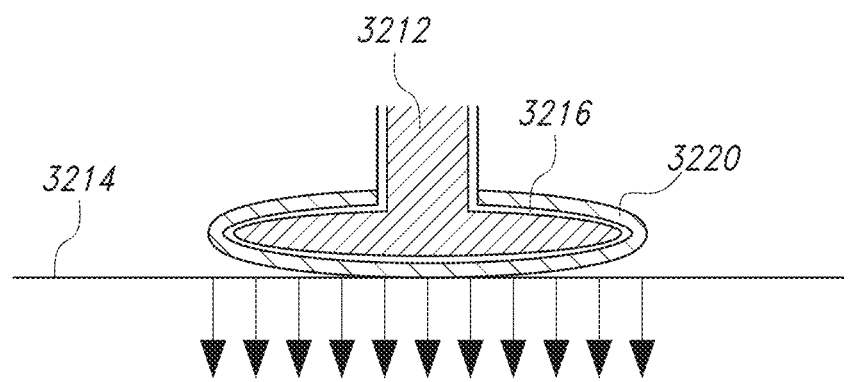
FIG. 32B schematically illustrates a typical, circular heated region of a treatment site arising from a capacitively coupled, dielectrically coated electrode in contact with a patient's skin surface.
Figure 32B:
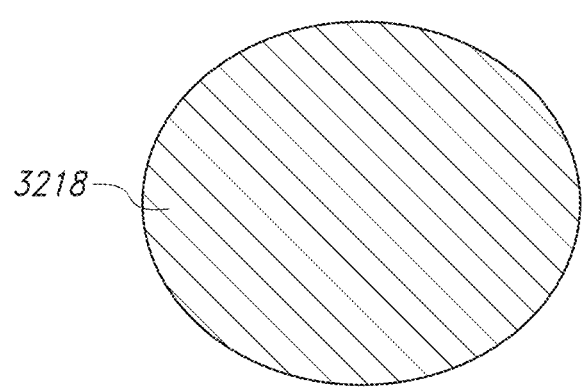

FIG. 32B shows a capacitively coupled electrode 3212 according to various embodiments having a relatively large surface area (e.g., at 60 mm) having a dielectric coating 3220 in contact with the patient's skin surface. The electrode 3212 may be similar to the electrode described in association with FIGS. 24 and 25. The electrode 3212 is in contact with the patient's skin surface 3214 via the dielectric coating 3220. The current path 3216 provides a uniform and homogenous discharge of electrical current over the entire surface of the coated electrode. The path of the capacitively coupled electrical current discharge results in a uniform/homogeneous region of treatment 3218. In one embodiment, this homogenous region of treated tissue is like a cylinder of tissue in which the interior of the sphere of tissue was uniformly or homogenously treated with electrical current. More specifically, the surface of the treated tissue is like a circle 3218 having uniform treatment at and inside the circumference of the circle. The tissue beneath uniformly treated circle is treated to a depth, but, due to anatomical variation in the tissue, the shape of the treated area at depth may vary. However, in an ideal case of uniform tissue from surface to depth, the treated area at the depth is in the shape of a uniformly treated cylinder. The capacitively coupled probe discussed here is circular, but such a probe may have any number of shapes suited to use on tissue, such as square, rectangular, rhombus, or another ellipse, etc.

Computing Environments

Figure 33:
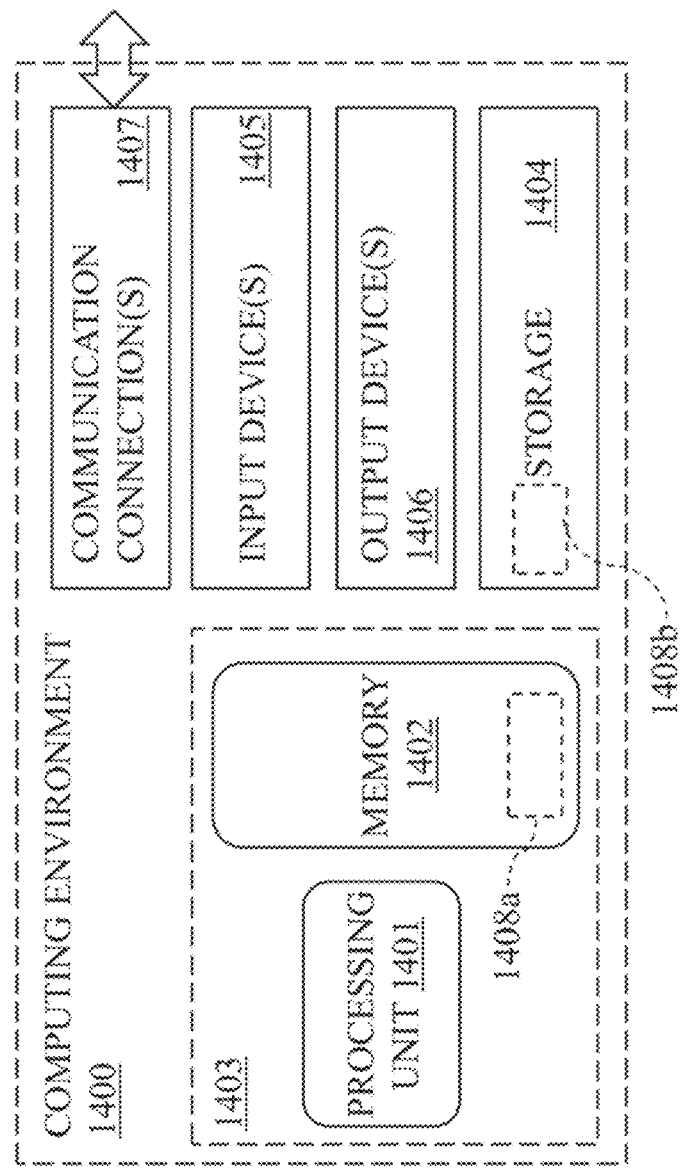
FIG. 33 schematically illustrates an example of a computing environment suitable for implementing one or more disclosed technologies.

FIG. 33 illustrates a generalized example of a suitable computing environment 1400 in which described methods, embodiments, techniques, and technologies relating, for example, to the control systems of electrosurgical generators discussed herein may be implemented. A control system of an electrosurgical generator may be implemented by a computing system. The computing environment 1400 is not intended to suggest any limitation as to scope of use or functionality of the technologies disclosed herein, as each technology may be implemented in diverse general-purpose or special-purpose computing environments. For example, each disclosed technology may be implemented with other computer system configurations, including wearable and handheld devices, multiprocessor systems, microprocessor-based or programmable consumer electronics, embedded platforms, network computers, minicomputers, mainframe computers, smartphones, tablet computers, data centers, audio devices, and the like. Each disclosed technology may also be practiced in distributed computing environments where tasks are performed by remote processing devices that are linked through a communications connection or network. In a distributed computing environment, program modules may be located in both local and remote memory storage devices.

The computing environment 1400 includes at least one central processing unit 1401 and memory 1402. In FIG. 33, this most basic configuration 1403 is included within a dashed line. The central processing unit 1401 executes computer-executable instructions and may be a real or a virtual processor. In a multi-processing system, multiple processing units execute computer-executable instructions to increase processing power and as such, multiple processors can run simultaneously. The memory 1402 may be volatile memory (e.g., registers, cache, RAM), non-volatile memory (e.g., ROM, EEPROM, flash memory, etc.), or some combination of the two. The memory 1402 stores software 1408a that can, for example, implement one or more of the technologies described herein, when executed by a processor. For example, a control system may use software that causes the control system to control the output of the RF waveform according to user-selectable parameters, sensed temperatures, or both.

A computing environment may have additional features. For example, the computing environment 1400 includes storage 1404, one or more input devices 1405, one or more output devices 1406, and one or more communication connections 1407. An interconnection mechanism (not shown) such as a bus, a controller, or a network, interconnects the components of the computing environment 1400. Typically, operating system software (not shown) provides an operating environment for other software executing in the computing environment 1400, and coordinates activities of the components of the computing environment 1400.

The store 1404 may be removable or non-removable, and can include selected forms of machine-readable media. In general, machine-readable media includes magnetic disks, magnetic tapes or cassettes, non-volatile solid-state memory, CD-ROMs, CD-RWs, DVDs, magnetic tape, optical data storage devices, and carrier waves, or any other machine-readable medium which can be used to store information, and which can be accessed within the computing environment 1400. The storage 1404 stores instructions for the software 1408, which can implement technologies described herein.

The store 1404 can also be distributed over a network so that software instructions are stored and executed in a distributed fashion. In other embodiments, some of these operations might be performed by specific hardware components that contain hardwired logic. Those operations might alternatively be performed by any combination of programmed data processing components and fixed hardwired circuit components.

The input device(s) 1405 may be a touch input device, such as a keyboard, keypad, mouse, pen, touchscreen, touch pad, or trackball, a voice input device, a scanning device, or another device, that provides input to the computing environment 1400. For audio, the input device(s) 1405 may include a microphone or other transducer (e.g., a sound card or similar device that accepts audio input in analog or digital form), or a computer-readable media reader that provides audio samples to the computing environment 1400.

The output device(s) 1406 may be a display, printer, speaker transducer, DVD-writer, or another device that provides output from the computing environment 1400.

The communication connection(s) 1407 enable communication over a communication medium (e.g., a connecting network) to another computing entity. The communication medium conveys information such as computer-executable instructions, compressed graphics information, processed signal information (including processed audio signals), or other data in a modulated data signal.

Thus, disclosed computing environments are suitable for performing disclosed orientation estimation and audio rendering processes as disclosed herein.

Machine-readable media are any available media that can be accessed within a computing environment 1400. By way of example, and not limitation, with the computing environment 1400, machine-readable media include memory 1402, storage 1404, communication media (not shown), and combinations of any of the above. Tangible machine-readable (or computer-readable) media exclude transitory signals.

As explained above, some disclosed principles can be embodied in a tangible, non-transitory machine-readable medium (such as microelectronic memory) having stored thereon instructions, which program one or more data processing components (generically referred to here as a "processor") to perform the digital signal processing operations described above including estimating, computing, calculating, measuring, adjusting, sensing, measuring, filtering, addition, subtraction, inversion, comparisons, and decision making. In other embodiments, some of these operations (of a machine process) might be performed by specific electronic hardware components that contain hardwired logic. Those operations might alternatively be performed by any combination of programmed data processing components and fixed hardwired circuit components.

One or more of the principles of the disclosed embodiments can be incorporated in various system configurations to achieve any of a variety of system characteristics. Systems described in relation to particular applications, or uses, are merely examples of systems incorporating the principles disclosed herein and are used to illustrate one or more aspects of the disclosed principles. Accordingly, electrosurgical systems having attributes that are different from those specific examples discussed herein can embody one or more of the principles, and/or can be used in applications not described herein in detail, for example in ablative surgical applications. Accordingly, such alternative embodiments also fall within the scope of this disclosure.

Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" or "or," as well as "and" and "or."

Moreover, nothing disclosed herein is intended to be dedicated to the public regardless of whether such disclosure is explicitly recited in the claims. To aid the Patent Office and any readers of any patent issued on this application in interpreting the claims appended hereto or otherwise presented throughout prosecution of this or any continuing patent application, applicants wish to note that they do not intend any claimed feature to be construed under or otherwise to invoke the provisions of 35 USC 112(f), unless the phrase "means for" or "step for" is explicitly used in the particular claim.

The technologies from any example can be combined with the technologies described in any one or more of the other examples. Accordingly, this detailed description shall not be construed in a limiting sense, and following a review of this disclosure, those of ordinary skill in the art will appreciate the wide variety of electrosurgical systems that can be devised using the various concepts described herein. Moreover, those of ordinary skill in the art will appreciate that the exemplary embodiments disclosed herein can be adapted to various configurations without departing from the disclosed principles. Thus, in view of the many possible embodiments to which the disclosed principles can be applied, it should be recognized that the above-described embodiments are only examples and should not be taken as limiting in scope. We therefore reserve all rights to claim the subject matter disclosed herein, as well as all combinations of each aspect of all embodiments shown or described herein.

The invention claimed is:

1. An electrosurgical handpiece for non-invasive aesthetic treatments, the handpiece comprising:
    a housing for a temperature sensor, wherein the housing defines a first patient-contact surface, an inner surface positioned opposite the first patient-contact surface, and an outer wall extending transversely relative to the first patient-contact surface;
    a temperature sensor thermally coupled with the inner surface of the housing;
    an energizable electrode defining a second patient-contact surface positioned outward of the first patient contact surface, wherein the energizable electrode comprises an inner first layer and a second layer coating the inner first layer and defining the second patient contact surface, and wherein the second patient contact surface has a diameter of at least 15 mm;
    an insulator positioned between the energizable electrode and the housing for the temperature sensor to inhibit thermal conduction between the energizable electrode and the housing for the temperature sensor; and
    wherein the first layer of the energizable electrode comprises a material having a higher thermal mass than the temperature sensor, and the second layer comprises a conductive coating.

2. An electrosurgical handpiece according to claim 1, further comprising a shaft extending proximally from the energizable electrode and defining an internal bore extending longitudinally of the shaft, wherein the insulator extends from a distal end positioned adjacent the first patient-contact surface and the second patient-contact surface to a proximal end positioned within the internal bore.

3. An electrosurgical handpiece according to claim 2, wherein the internal bore defines a first thread and the insulator defines a second thread, wherein the first and second threads are complementary and matingly engageable with each other.

4. An electrosurgical handpiece according to claim 1, further comprising an electrical conductor extending proximally within the handpiece from the temperature sensor.

5. An electrosurgical handpiece according to claim 1, wherein the first patient-contact surface and the second patient-contact surface are co-centrically aligned with each other.

6. An electrosurgical handpiece according to claim 1, wherein the temperature sensor comprises one or more of a thermocouple, a resistance-temperature detector, a thermistor, and a diode.

7. An electrosurgical handpiece according to claim 1, wherein the housing for the temperature sensor comprises a material having a thermal conductivity equal to or greater than about 200 W/mK.

8. An electrosurgical handpiece according to claim 1, wherein the second layer comprises a dielectric coating defining the second patient contact surface.

9. An electrosurgical handpiece according to claim 8, the dielectric material having a dielectric constant of between about 4 to about 12 at an operating frequency of the energizable electrode.

10. An electrosurgical handpiece according to claim 9, wherein the operating frequency of the energizable electrode is between about 3-30 MHz.

11. An electrosurgical handpiece according to claim 8, the dielectric material coating having a substantially even thickness of about 0.004 to about 0.020 inches.

12. An electrosurgical handpiece according to claim 1, wherein the first patient-contact surface has a larger surface area than a surface area of the temperature sensor that is coupled to the housing.

13. An electrosurgical handpiece according to claim 1, wherein the energizeable electrode is capacitively couplable with a treatment surface.

14. An electrosurgical handpiece according to claim 1, further comprising:
a communication component configured to receive a temperature measured by the temperature sensor and to communicate the received temperature to a control system.

15. An electrosurgical handpiece according to claim 14, wherein the energizable electrode is configured to output a radio frequency (RF) waveform received from an electrosurgical generator.

16. An electrosurgical handpiece according to claim 1, wherein the second patient contact surface comprises a continuous solid surface.

17. An electrosurgical handpiece according to claim 1, wherein the first layer of the energizable electrode comprises a first electrically conductive material and the second layer comprises a second electrically conductive material.

18. An electrosurgical handpiece according to claim 1, wherein the ratio of the thermal mass of the electrode to the thermal mass of the temperature sensor is greater than 100:1.

19. An electrosurgical handpiece according to claim 1, wherein the first layer of the energizable electrode comprises a material having a thermal mass lower than a thermal mass of a dermal layer of human skin, and the second layer comprises a conductive coating.

20. An electrosurgical system, comprising:
an electrosurgical generator configured to output a radio-frequency (RF) waveform and the electrosurgical handpiece of claim 1.

21. An electrosurgical system according to claim 20, wherein the electrosurgical generator further comprises:
a control system configured to receive a temperature measurement from the temperature sensor, compare the received temperature to a threshold temperature, and to modify the output waveform in response to the comparison.

22. An electrosurgical system according to claim 20, wherein the electrosurgical generator further comprises:
a generator configured to combine a first current waveform having a corresponding first frequency, a first amplitude, and a first pulse-width with a second current waveform having a corresponding second frequency, a second amplitude, and a second pulse-width to define a blended waveform output; and
a control system configured to control one or more of the first frequency, the first amplitude, the first pulse-width, the second frequency, the second amplitude and the second pulse-width responsive to a temperature received from the temperature sensor.

23. An electrosurgical system according to claim 22, wherein the electrosurgical generator further comprises:
a first power source configured to generate the first current waveform;
a second power source configured to generate the second current waveform; and
a radio-frequency amplifier configured to blend the first and second current waveforms to define a blended waveform and to output the blended waveform to the electrosurgical handpiece.

24. An electrosurgical system according to claim 20, wherein the electrosurgical handpiece comprises an insulator positioned between the energizable electrode and the temperature sensor to inhibit thermal conduction between the energizable electrode and the temperature sensor.

25. An electrosurgical system according to claim 20, wherein the second patient contact surface comprises a continuous solid surface.

26. An electrosurgical handpiece for non-invasive aesthetic treatments, the handpiece comprising:
a housing for a temperature sensor, wherein the housing defines a first patient-contact surface, an inner surface positioned opposite the first patient-contact surface, and an outer wall extending transversely relative to the first patient-contact surface;
a temperature sensor thermally coupled with the inner surface of the housing;
an energizable electrode defining a second patient-contact surface positioned outward of the first patient contact surface, wherein the energizable electrode comprises an inner first layer and a second layer coating the inner first layer and defining the second patient contact surface, and wherein the second patient contact surface has a diameter of at least 15 mm;
an insulator positioned between the energizable electrode and the housing for the temperature sensor to inhibit thermal conduction between the energizable electrode and the housing for the temperature sensor; and
wherein the ratio of the thermal mass of the electrode to the thermal mass of the temperature sensor is greater than 100:1.

* * * * *